(12) United States Patent
Hirai et al.

(10) Patent No.: US 9,344,691 B2
(45) Date of Patent: May 17, 2016

(54) IMAGING DEVICE, OBJECT DETECTING APPARATUS, OPTICAL FILTER, AND MANUFACTURING METHOD OF OPTICAL FILTER

(75) Inventors: Hideaki Hirai, Kanagawa (JP); Yasuhiro Sato, Kanagawa (JP)

(73) Assignee: RICOH COMPANY, LTD., Tokyo (JP)

(*) Notice: Subject to any disclaimer, the term of this patent is extended or adjusted under 35 U.S.C. 154(b) by 295 days.

(21) Appl. No.: 14/235,613

(22) PCT Filed: Jul. 24, 2012

(86) PCT No.: PCT/JP2012/069270
§ 371 (c)(1),
(2), (4) Date: Jan. 28, 2014

(87) PCT Pub. No.: WO2013/018743
PCT Pub. Date: Feb. 7, 2013

(65) Prior Publication Data
US 2014/0184800 A1    Jul. 3, 2014

(30) Foreign Application Priority Data

Jul. 29, 2011 (JP) ................................. 2011-166618

(51) Int. Cl.
*H04N 7/12* (2006.01)
*H04N 11/02* (2006.01)
*H04N 11/04* (2006.01)
(Continued)

(52) U.S. Cl.
CPC *H04N 9/045* (2013.01); *B60R 1/00* (2013.01); *G01N 21/958* (2013.01); *G02B 5/201* (2013.01); *G02B 5/3025* (2013.01); *G06K 9/00791* (2013.01); *G06K 9/00798* (2013.01); *G06K 9/00825* (2013.01); *H01L 27/14621* (2013.01); *G01N 2021/9586* (2013.01); *Y10T 156/10* (2015.01)

(58) Field of Classification Search
None
See application file for complete search history.

(56) References Cited

U.S. PATENT DOCUMENTS

| 2004/0004779 A1 | 1/2004 | Kochergin et al. |
| 2005/0195485 A1 | 9/2005 | Hirai et al. |

(Continued)

FOREIGN PATENT DOCUMENTS

| CN | 1584635 A | 2/2005 |
| CN | 101887900 A | 11/2010 |

(Continued)

OTHER PUBLICATIONS

Combined Office Action and Search Report issued Mar. 30, 2015 in Chinese Patent Application No. 201280036739.7 (with English language translation).

(Continued)

*Primary Examiner* — Frederick Bailey
*Assistant Examiner* — Talha M Nawaz
(74) *Attorney, Agent, or Firm* — Oblon, McClelland, Maier & Neustadt, L.L.P.

(57) ABSTRACT

An imaging device includes an optical filter. The optical filter has a configuration in which a polarization filter layer and a spectral filter layer are laminated in light transmission direction. Of the polarization filter layer and the spectral filter layer, the layer on the lower side in lamination direction has an uneven top face in the lamination direction. The optical filter is formed by filling the uneven top face with a predetermined filling material so as to even out the top face and then forming other layer.

10 Claims, 27 Drawing Sheets

(51) Int. Cl.
*H04N 9/04* (2006.01)
*G01N 21/958* (2006.01)
*G06K 9/00* (2006.01)
*H01L 27/146* (2006.01)
*G02B 5/20* (2006.01)
*G02B 5/30* (2006.01)
*B60R 1/00* (2006.01)

(56) References Cited

U.S. PATENT DOCUMENTS

| | | |
|---|---|---|
| 2007/0109648 A1 | 5/2007 | Wada et al. |
| 2007/0127111 A1 | 6/2007 | Hashiguchi et al. |
| 2007/0217011 A1 | 9/2007 | Kiyosawa et al. |
| 2008/0106789 A1 | 5/2008 | Hirai et al. |
| 2009/0290039 A1 | 11/2009 | Kanamori et al. |
| 2009/0315993 A1 | 12/2009 | Hirai |
| 2010/0014073 A1 | 1/2010 | Hashiguchi et al. |
| 2010/0020401 A1 | 1/2010 | Fujimoto et al. |
| 2010/0073753 A1* | 3/2010 | Kimura ............... G02F 1/1396 359/246 |
| 2010/0118366 A1 | 5/2010 | Tokita et al. |
| 2010/0155977 A1 | 6/2010 | Hirai et al. |
| 2010/0282945 A1 | 11/2010 | Yokogawa |
| 2011/0255390 A1 | 10/2011 | Hirai |
| 2011/0285898 A1 | 11/2011 | Kasahara et al. |
| 2012/0002280 A1 | 1/2012 | Hirai et al. |
| 2013/0027557 A1* | 1/2013 | Hirai ................... B60S 1/0844 348/148 |
| 2013/0063569 A1 | 3/2013 | Sato et al. |
| 2014/0253756 A1 | 9/2014 | Yokogawa |
| 2014/0303853 A1* | 10/2014 | Itoh ................... B60R 11/04 701/49 |

FOREIGN PATENT DOCUMENTS

| | | |
|---|---|---|
| EP | 2 579 568 A1 | 4/2013 |
| JP | 63-146590 | 6/1988 |
| JP | 2006-351800 | 12/2006 |
| JP | 2007-86720 | 4/2007 |
| JP | 2009-55624 | 3/2009 |
| JP | 2009-157043 A | 7/2009 |
| JP | 2010-186818 | 8/2010 |
| JP | 2010-263158 A | 11/2010 |
| JP | 2012-117872 | 6/2012 |
| JP | 2012-230341 A | 11/2012 |

OTHER PUBLICATIONS

Extended European Search Report issued on Dec. 8, 2014 in Patent Application No. 12820659.6.
International Search Report issued Oct. 9, 2012 in PCT/JP2012/069270 filed Jul. 24, 2012.
Written Opinion of the International Searching Authority issued Oct. 9, 2012 in PCT/JP2012/069270 filed Jul. 24, 2012.
Office Action issued on Apr. 24, 2015 in Japanese Patent Application No. 2011-166618.
Combined Office Action and Search Report issued on Dec. 11, 2015 in Chinese Patent Application No. 201280036739.7 with English translation.
Japanese Office Action issued in Application No. 2011-166618 on Dec. 11, 2015.

* cited by examiner

203

WIRE GRID STRUCTURE AREA

LIGHT INTERCEPTING AREA (ALUMINUM BETA FILM)

WIRE GRID STRUCTURE AREA

LIGHT INTERCEPTING AREA (ALUMINUM BETA FILM)

APERTURE (WITHOUT WIRE GRID STRUCTURE)

LIGHT INTERCEPTING AREA (ALUMINUM BETA FILM)

APERTURE (WITHOUT WIRE GRID STRUCTURE)

LIGHT INTERCEPTING AREA (ALUMINUM BETA FILM)

APERTURE (WITHOUT WIRE GRID STRUCTURE)

LIGHT INTERCEPTING AREA (ALUMINUM BETA FILM)

WIRE GRID STRUCTURE AREA

LIGHT INTERCEPTING AREA (ALUMINUM BETA FILM)

⟶ HORIZONTAL POLARIZATION COMPONENT (Is)
---⟶ VERTICAL POLARIZATION COMPONENT (IP)

(a) WET          (b) DRY

FIG.34
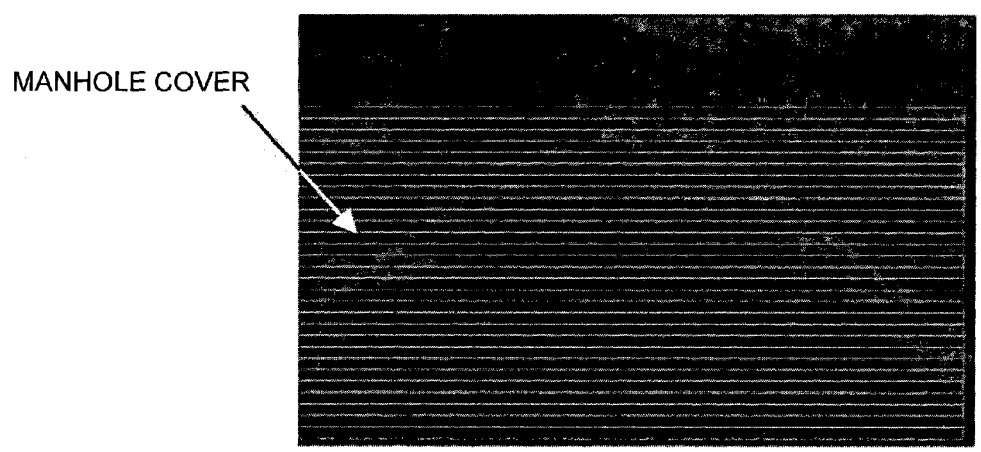
FIG.35A FIG.35B
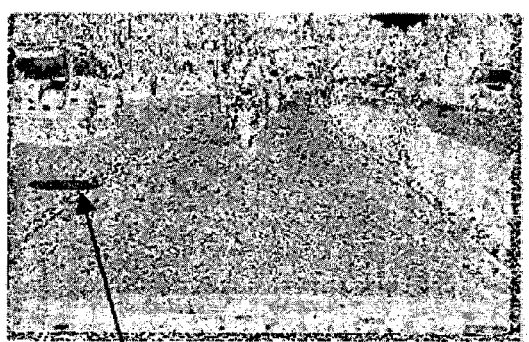

FIG.36
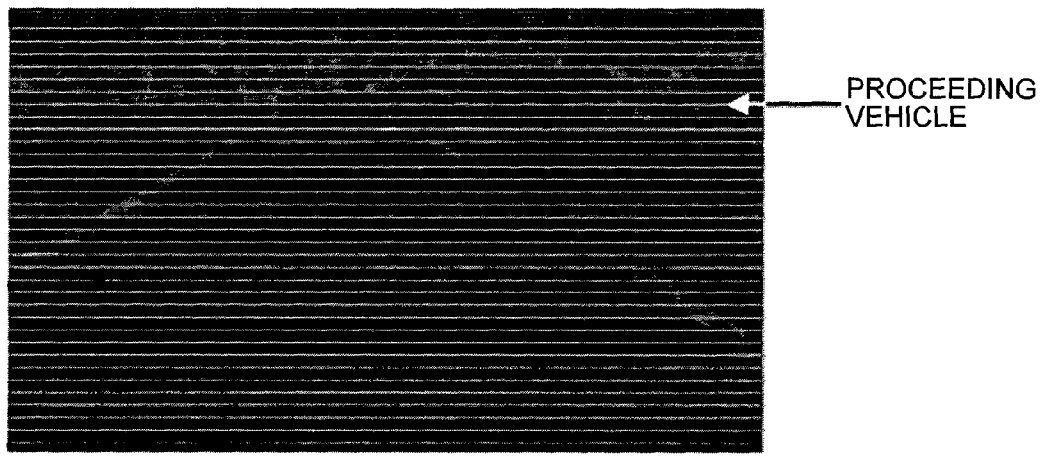
FIG.37A  FIG.37B
 

IMAGING DEVICE, OBJECT DETECTING APPARATUS, OPTICAL FILTER, AND MANUFACTURING METHOD OF OPTICAL FILTER

TECHNICAL FIELD

The present invention relates to an imaging device that captures images within an imaging area by means of receiving light, via an optical filter, from an object present in the imaging area using an image sensor that is configured with a pixel array having a two-dimensional arrangement of light receiving elements; relates to an object detecting apparatus including the imaging device; and relates to the optical filter and a manufacturing method of the optical filter.

BACKGROUND ART

In Patent Literature 1 (Japanese Patent Application Laid-open No. 2007-86720) is disclosed a polarized imaging apparatus that includes: a polarizer array divided in two or more types of polarizer areas each having a different transmission axis (i.e., a different polarization direction); a light receiving element array that independently receives the light that has passed through each polarizer area; and an image processing unit that processes polarization components received from the light receiving element array. In this polarized imaging apparatus, the polarizer array is configured either with polarizers made of photonic crystals or with wire grid polarizers.

In Patent Literature 2 (Japanese Patent Application Laid-open No. 2009-55624) is disclosed an image processing method in which an imaging apparatus including a color polarization obtaining unit, which has a color filter and a patterned polarizer arranged in a superposed manner on the front face thereof, is used so that color images and polarization information can be obtained in a concurrent manner. In this imaging apparatus, as the color filter, a Bayer color mosaic filter is used in which color filter units of different colors (RGB) are formed each corresponding to a set of four adjacent pixels of an imaging element. With the set of four adjacent pixels corresponding to each color filter unit, a patterned polarizer having a different principal polarization axis adheres closely. In this imaging apparatus, four pixels of an imaging element form a single set, and four types of polarization information can be obtained for each color of RGB.

In the imaging apparatus disclosed in Patent Literature 2 mentioned above, spectroscopic information (wavelength-band-specific information) and polarization information (polarization-direction-specific information) for each color of RGB can be obtained by capturing images only once. However, in Patent Literature 2, no concrete explanation is given regarding the method of manufacturing the color polarization obtaining unit, which has a color filter and a patterned polarizer arranged thereon in a superposed manner. Meanwhile, in recent years, pixel spacing in imaging elements (light receiving elements) has decreased to extremely narrow levels. Irrespective of that, in Patent Literature 2, no concrete explanation is given whatsoever regarding the method of forming the color filter units each having a different color (RGB) for a miniscule area of a set of four adjacent pixels of a light receiving element; or regarding the method of forming the patterned polarizer having a different principal polarization axis for each miniscule area such as a single pixel of a light receiving element; or regarding the method of arranging the color filter and the patterned polarizer in a superposed manner.

Meanwhile, in Patent Literature 1, there is an explanation in concrete terms of the method of manufacturing the polarizer array (polarization filter) that is divided in two or more types of polarizer areas each having a different transmission axis (i.e., a different polarization direction) for each miniscule area. Besides, regarding a color filter (spectral filter) in which the color filter units each having a different color for a miniscule area are formed, the microfabrication technology of recent years can be used to make such an arrangement feasible. However, a diligent research by the inventor(s) of the present invention found that following issues arise when a spectral filter and a polarization filter are arranged in a superposed manner.

In the case of arranging a spectral filter and a polarization filter in a superposed manner in a microscopic structure, a common manufacturing method is to form a laminate structure in which spectral filter layers and polarization filter layers are sequentially formed on a transparent filter substrate. Moreover, in order to obtain a polarization filter layer that is segmented into areas each having a different polarization direction for each miniscule area of a single pixel or a few pixels of a light receiving element; it is desirable to use a polarizer structure that is configured either with polarizers made of photonic crystals or has wire grid polarizers as described in Patent Literature 1 mentioned above and that is suitable for a microscopic structure. However, a polarization filter layer with such a polarizer structure happens to have an uneven top face. For that reason, if an attempt is made to form a spectral filter layer on that polarization filter layer, then the spectral filter layer also gets formed along the uneven top face of the polarization filter layer. That causes irregularity in the layer thickness of the spectral filter layer, thereby resulting in non-uniformity in the spectral performance of the spectral filter layer in the direction of light receiving element surfaces in the image sensor.

Furthermore, as far as a spectral filter layer is concerned on which filter areas are formed with each filter area having a different color (i.e., a different wavelength band) for each miniscule area; in connection to the fact that the filter area of each color needs to be formed from a different material, it is difficult to have identical layer thickness among the filter areas. For that reason, the top face of a spectral filter layer also becomes uneven. As a result, in the case of forming a polarization filter layer on a spectral filter layer, irregularity occurs in the layer thickness of the polarization filter layer. That causes non-uniformity in the polarization performance of the polarization filter layer in the direction of light receiving element surfaces in the image sensor.

The present invention has been made in view of the above-mentioned issues, and it is an object of the present invention to provide an imaging device that, in a structure in which polarization filter layers, each segmented into areas on the basis of miniscule areas equivalent to a single pixel or a few pixels of a light receiving element, and spectral filter layers are arranged in a laminated manner, enables achieving curbing of irregularity in the layer thickness of those layers and enables fulfillment of the original functions of each layer; as well as to provide an object detecting apparatus including the imaging device, and to provide optical filters and a manufacturing method of the optical filters.

DISCLOSURE OF INVENTION

The present invention provides an imaging device for capturing images within an imaging area by means of receiving light, via an optical filter, from an object present in the imaging area using an image sensor that is configured with a pixel array having a two-dimensional arrangement of light receiving elements. The optical filter has a configuration in which a polarization filter layer and a spectral filter layer are laminated in light transmission direction. The polarization filter layer includes a first type area, which selectively transmits a polarization component of light in only a particular direction, and a second type area, which either transmits light without selecting a polarization component or selectively transmits a polarization component of light in a different direction than the particular direction. The first and second type areas are segmented into areas each corresponding to a unit area formed with one or more light receiving elements of the image sensor. The spectral filter layer includes a third type area, which selectively transmits light of only a specific wavelength band included in used wavelength bands that can pass through the polarization filter layer, and a fourth type area, which either transmits light without selecting a wavelength or transmits light of a wavelength band that is different than the specific wavelength band and that is included in the used wavelength bands. The third and fourth type areas are segmented into areas each corresponding to a unit area formed with one or more light receiving elements of the image sensor. Of the polarization filter layer and the spectral filter layer, the layer on the lower side in lamination direction has an uneven top face in the lamination direction. The optical filter is formed by filling the uneven top face with a predetermined filling material so as to even out the top face and then forming other layer.

According to the present invention, of a polarization filter layer and a spectral filter layer that constitute an optical filter, the layer on the lower side in the lamination direction has an uneven top face in the lamination direction. In the present invention, before forming the other layer on the top face of the layer on the lower side in the lamination direction, a predetermined filling material is filled on the uneven top face so that the uneven top face is evened out. With such a configuration, even if the other layer is formed on the layer being on the lower side in the lamination direction and having an uneven top face, irregularity in the layer thickness of the other layer along the uneven face is prevented from occurring. That allows the other layer to fulfill its primary function. Meanwhile, as long as the filling material that fills the top face of the layer on the lower side in the lamination direction does not interfere in the functions of the polarization filter layer and the spectral filter layer, any type of filling material can be used.

BRIEF DESCRIPTION OF DRAWINGS

FIG. 34 is an explanatory diagram for explaining an example of setting processing lines with respect to a captured image at the time of detecting on-road metal bodies;

FIG. 35A is an exemplary image illustrating a monochrome luminance image (non-dispersive type/non-polarized type) in which an imaging area containing on-road metal bodies is captured;

FIG. 35B is an exemplary image illustrating a difference polarization degree image of non-dispersive type in which the same imaging area is captured;

FIG. 36 is an explanatory diagram for explaining an example of setting processing lines with respect to a captured image at the time of detecting three-dimensional objects;

FIG. 37A is an exemplary image illustrating a monochrome luminance image (non-dispersive type/non-polarized type) in which an imaging area containing three-dimensional objects is captured;

FIG. 37B is an exemplary image illustrating a difference polarization degree image of non-dispersive type in which the same imaging area is captured;

BEST MODE(S) FOR CARRYING OUT THE INVENTION

Explained below is an exemplary embodiment in which an imaging device according to the present invention is implemented in an in-vehicle device control system.

Meanwhile, the imaging device according to the present invention is not limited to be implemented in the in-vehicle device control system, but can also be implemented in any other system in which, for example, an object detecting apparatus is installed to perform object detection based on captured images.

Figure 1:
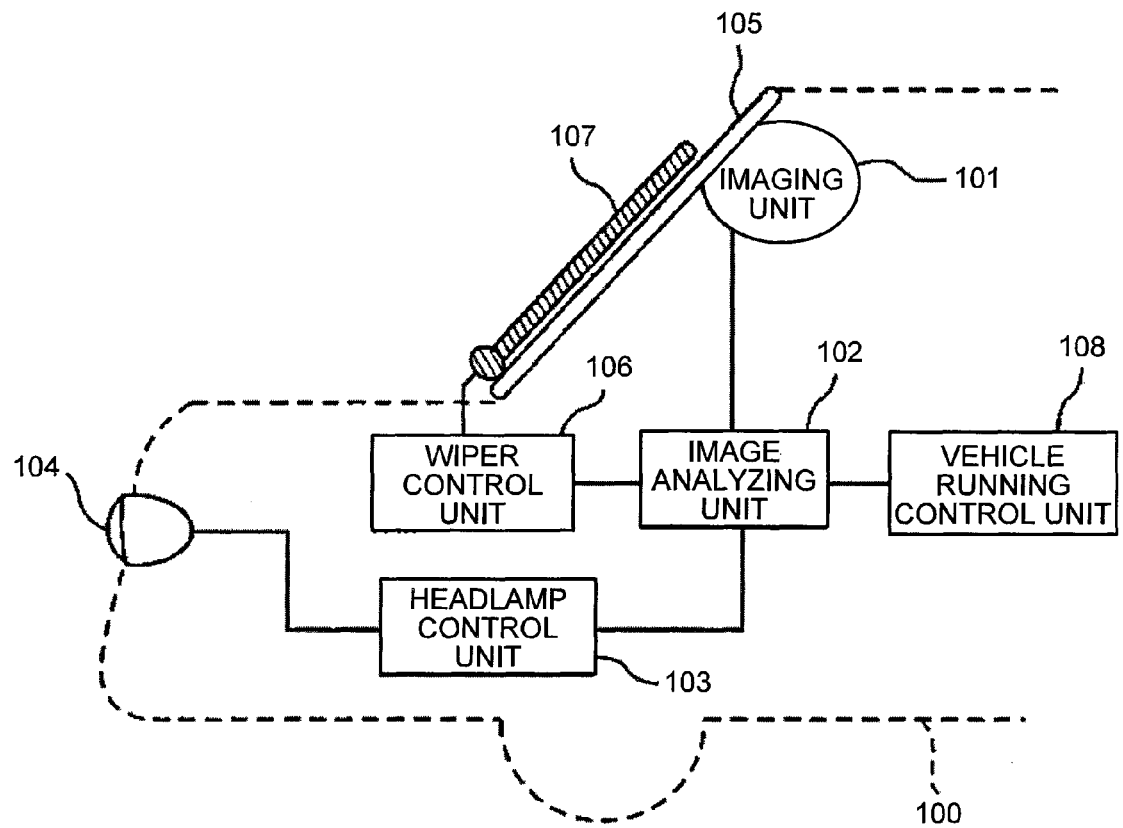
FIG. 1 is a schematic diagram illustrating an overall configuration of an in-vehicle device control system according to an embodiment.

FIG. 1 is a schematic diagram illustrating an overall configuration of an in-vehicle device control system according to the present embodiment.

The in-vehicle device control system makes use of captured-image data of images of a vehicle-travelling direction front area (imaging area) that are captured by an imaging device installed in a motor vehicle such as an own motor vehicle 100, and accordingly performs light distribution control for headlamps, drive control for wipers, and control of other in-vehicle devices.

The imaging device that is installed in the in-vehicle device control system according to the present embodiment is installed in an imaging unit 101. The imaging device captures images of the vehicle-travelling direction front area as the imaging area. Meanwhile, the imaging device is disposed, for example, in the vicinity of a rearview mirror (not illustrated) of a windshield 105 of the own motor vehicle 100. The captured-image data, which is obtained by capturing images by the imaging device of the imaging unit 101, is input to an image analyzing unit 102. Then, the image analyzing unit 102 analyzes the captured-image data sent by the imaging device; calculates locations, orientations, and distances of other motor vehicles present in front of the own motor vehicle 100; detects any attached substances such as raindrops or foreign substances on the windshield 105; and detects target objects for detection such as the white lines (demarcation lines) drawn on the road surface within the imaging area. Regarding the detection of other motor vehicles, a proceeding motor vehicle that is travelling in the same direction as the own motor vehicle 100 is detected by identifying the tail lamp of that motor vehicle; and an oncoming motor vehicle that is travelling in the opposite direction of the own motor vehicle 100 is detected by identifying the headlamp of the oncoming motor vehicle.

The result of calculations performed by the image analyzing unit 102 is sent to a headlamp control unit 103. Then, for example, by referring to distance data calculated by the image analyzing unit 102, the headlamp control unit 103 generates control signals for controlling a headlamp 104. More particularly, for example, the headlamp control unit 103 performs control to switch between a high beam and a low beam of the headlamp 104 as well as performs partial light interception control of the headlamp 104 with the aim of securing visibility for the driver of the own motor vehicle 100 while preventing the intense light of the headlamp of the own motor vehicle 100 from getting in the eyes of the drivers of other motor vehicles so that those drivers of other motor vehicles do not get distracted.

The result of calculations performed by the image analyzing unit 102 is sent to a wiper control unit 106. Then, the wiper control unit 106 controls a wiper 107 so as to remove any attached substances such as raindrops or foreign substances from the windshield 105 of the own motor vehicle 100. The wiper control unit 106 receives a result of foreign substance detection performed by the image analyzing unit 102 and generates control signals for controlling the wiper 107. The control signals generated by the wiper control unit 106 are sent to the wiper 107 as a trigger to start operations to secure visibility for the driver of the own motor vehicle 100.

Meanwhile, the result of calculations performed by the image analyzing unit 102 is also sent to a vehicle running control unit 108. Then, based on the result of white line detection performed by the image analyzing unit 102, the vehicle running control unit 108 performs running support control such as issuing a warning to the driver of the own motor vehicle 100 when the own motor vehicle 100 is straying off the traffic lane area demarcated by white lines or controlling the steering wheel or brakes of the own motor vehicle 100.

Figure 2:
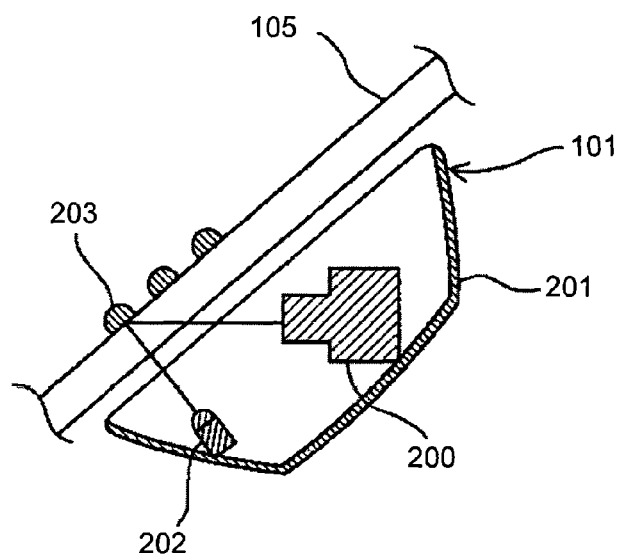
FIG. 2 is a schematic diagram illustrating an overall configuration of an imaging unit installed in the in-vehicle device control system.

FIG. 2 is a schematic diagram illustrating an overall configuration of the imaging unit 101.

Figure 3:
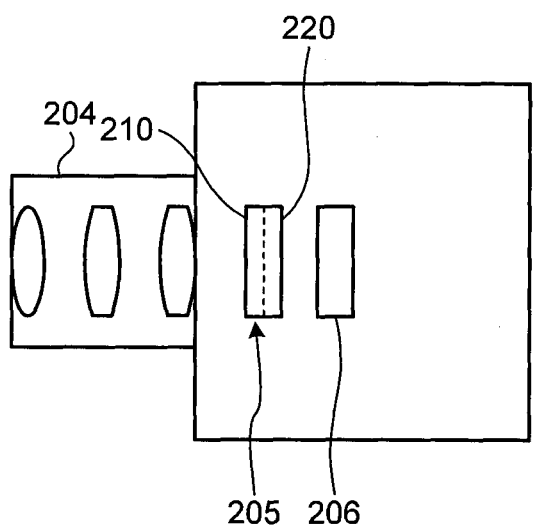
FIG. 3 is an explanatory diagram for explaining an overall configuration of an imaging device installed in the imaging unit.

FIG. 3 is an explanatory diagram for explaining an overall configuration of an imaging device 200 that is installed in the imaging unit 101.

The imaging unit 101 includes the imaging device 200, a light source 202, and an imaging casing 201 that houses the imaging device 200 and the light source 202. The imaging unit 101 is installed at the inner wall surface of the windshield 105 of the own motor vehicle 100. As illustrated in FIG. 3, the imaging device 200 includes an imaging lens 204, an optical filter 205, and an image sensor 206. The light source 202 is disposed to emit light toward the windshield 105 in such a way that, when the emitted light reflects from the outer wall surface of the windshield 105, the reflected light falls on the imaging device 200.

In the present embodiment, the light source 202 is used to detect any attached substance (hereinafter, the explanation is given for an example when the attached substance is raindrops) on the outer wall surface of the windshield 105. When raindrops 203 are not attached to the outer wall surface of the windshield 105, the light emitted by the light source 202 reflects from the interface between the outer wall surface of the windshield 105 and the outside air, and the reflected light falls on the imaging device 200. On the other hand, when the raindrops 203 are attached to the outer wall surface of the windshield 105 as illustrated in FIG. 2, the refractive index difference between the outer wall surface of the windshield 105 and the raindrops 203 becomes smaller than the refractive index difference between the outer wall surface of the windshield 105 and the outside air. As a result, the light emitted by the light source 202 passes through the interface and does not fall on the imaging device 200. By making use of such a difference, the raindrops 203 attached to the outer wall surface of the windshield 105 are detected from the captured-image data of the imaging device 200.

Moreover, in the present embodiment, as illustrated in FIG. 2, the imaging device 200 and the light source 202 are covered by the windshield 105 as well as the imaging casing 201. By using the imaging casing 201 as a cover in this fashion, even if a situation arises when the inner wall surface of the windshield 105 becomes clouded, the imaging unit 101 covered by the windshield 105 is prevented from getting clouded. As a result, it becomes possible to prevent a situation in which clouding of the windshield 105 causes the image analyzing unit 102 to perform incorrect analysis. Hence, various control operations based on the analysis result of the image analyzing unit 102 can be performed in a proper manner.

However, when the clouding of the windshield 105 is detected from the captured-image data of the imaging device 200 for the purpose of, for example, controlling the air conditioner of the own motor vehicle 100; an air passageway may be secured in some part of the imaging casing 201 so as to ensure that the portion of the windshield 105 facing the imaging device 200 is in the same condition as the remaining portion.

In the present embodiment, the focal position of the imaging lens 204 is either set to infinity or set to be in between infinity and the windshield 105. With that, not only in the case of detecting the raindrops 203 attached to the windshield 105 but also in the cases of detecting proceeding motor vehicles, detecting oncoming motor vehicles, and detecting white lines; it becomes possible to obtain appropriate information from the captured-image data of the imaging device 200.

For example, regarding the detection of the raindrops 203 attached to the windshield 105, since raindrop images in the captured-image data are often round in shape, a shape recognition operation is performed with the aim of determining whether or not raindrop candidate images in the captured-image data are round in shape and identifying raindrop candidate images in round shape as raindrop images. While performing such a shape recognition operation, rather than having the focal point of the imaging lens 204 set to the raindrops 203 attached to the outer wall surface of the windshield 105, having the focal point either set to infinity or set to be in between infinity and the windshield 105 results in blurring to some extent. Such blurring enhances the shape recognition rate of raindrops (round shapes) and enhances the raindrop detection performance.

Figure 4:
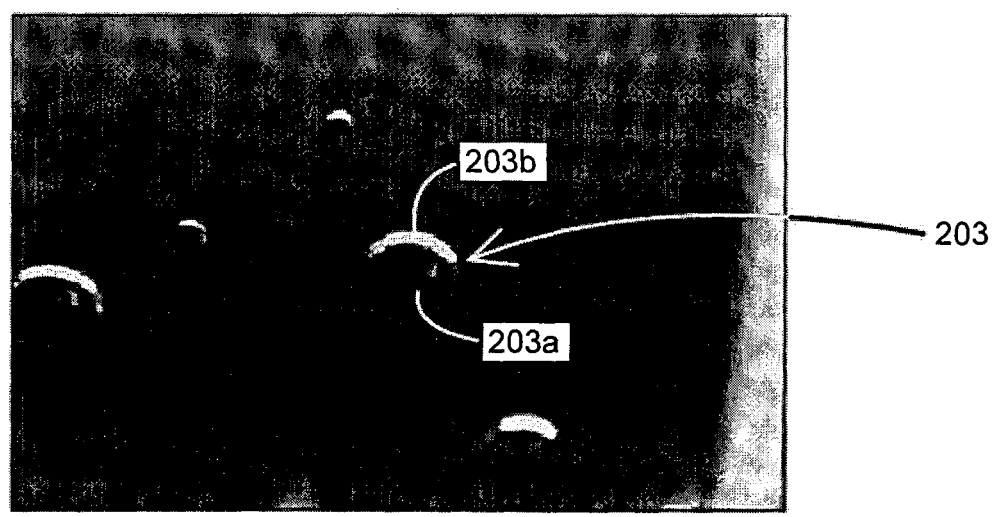
FIG. 4 is an explanatory diagram for explaining infrared color image data that represents captured-image data for raindrop detection when the focal point of an imaging lens is set to raindrops that are attached to the outer wall surface of the windshield of an own motor vehicle.

FIG. 4 is an explanatory diagram for explaining infrared color image data that represents captured-image data for raindrop detection when the focal point of the imaging lens 204 is set to the raindrops 203 that are attached to the outer wall surface of the windshield 105.

Figure 5:
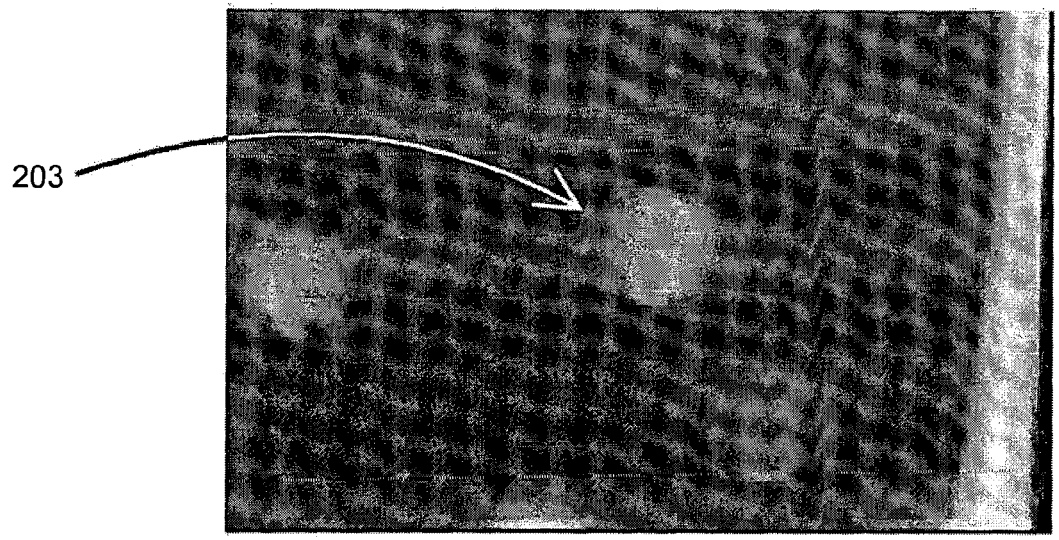
FIG. 5 is an explanatory diagram for explaining infrared color image data that represents captured-image data for raindrop detection when the focal point is set to infinity.

FIG. 5 is an explanatory diagram for explaining infrared color image data that represents captured-image data for raindrop detection when the focal point is set to infinity.

When the focal point of the imaging lens 204 is set to the raindrops 203 attached to the outer wall surface of the windshield 105, a background image 203a reflected in raindrops also gets captured as illustrated in FIG. 4. Such background image 203a is responsible for false detection of the raindrops 203. Moreover, as illustrated in FIG. 4, there are times when only portions 203b of raindrops appear brighter in a bow-like manner. The shapes of such bright portions, that is, the shapes of the raindrop images change according to the direction of sunlight or according to the positions of street lamps. During the shape recognition operation, dealing with such raindrop images that change to various shapes leads to an increase in the processing load and a decline in the recognition accuracy.

In contrast, when the focal point is set to infinity, blurring occurs to some extent as illustrated in FIG. 5. Because of that, the background image 203a is not reflected in the captured-image data, thereby lessening false detection of the raindrops 203. Moreover, because of the blurring that occurs to some extent, there is a decrease in the extent to which the shapes of raindrop images change according to the direction of sunlight or according to the positions of street lamps. Thus, the raindrop images always remain substantially round in shape. As a result, the shape recognition operation can be performed with respect to the raindrops 203 with a smaller processing load and with high recognition accuracy.

However, when the focal point is set to infinity, while identifying the tail lamp of a proceeding motor vehicle that is running in the distance, there are times when only about a single light receiving element in the image sensor 206 receives the light from the tail lamp. In that case, although described later in detail, there is a possibility that the light from the tail lamp is not received by a red-light receiving element, which is supposed to receive the light of the color of the tail lamp (red color). In such a case, the tail lamp cannot be recognized and the proceeding motor vehicle cannot be detected. In order to avoid such malfunctioning, it is desirable to set the focal point of the imaging lens 204 to short of infinity. With that, the tail lamp of the proceeding motor vehicle that is running in the distance gets blurred, so that the number of light receiving elements that receive the light from the tail lamp can be increased. As a result, the accuracy of recognizing the tail lamp improves, thereby enabling achieving enhancement in the detection accuracy of the proceeding motor vehicle.

In the light source 202 of the imaging unit 101, it is possible to use light emitting diodes (LEDs) or laser diodes (LD). Moreover, as far as the emission wavelength of the light source 202 is concerned, it is possible to use, for example, the visible light or the infrared light. However, in order to avoid a situation in which the drivers of oncoming motor vehicles or the pedestrians are distracted by the light emitted by the light source 202, it is desirable that a wavelength in the infrared light area, such as a wavelength from 800 nm to 1000 nm, is selected that is longer than the wavelength of the visible light and that falls within the range of light receiving sensitivity of the image sensor 206. According to the present embodiment, the light source 202 emits light having a wavelength in the infrared light area.

Herein, when the imaging device 200 captures images with infrared wavelength light emitted by the light source 202 and reflected from the windshield 105, the image sensor 206 of the imaging device 200 receives not only the infrared wavelength light emitted by the light source 202 but also a large amount of ambient light such as the sunlight that includes the infrared wavelength light. Therefore, in order to distinguish the infrared wavelength light emitted by the light source 202 from a large amount of ambient light; the amount of luminescence of the light source 202 needs to be sufficiently greater than the ambient light. However, it is often the case that the light source 202 having a large amount of luminescence is difficult to use.

Figure 6:
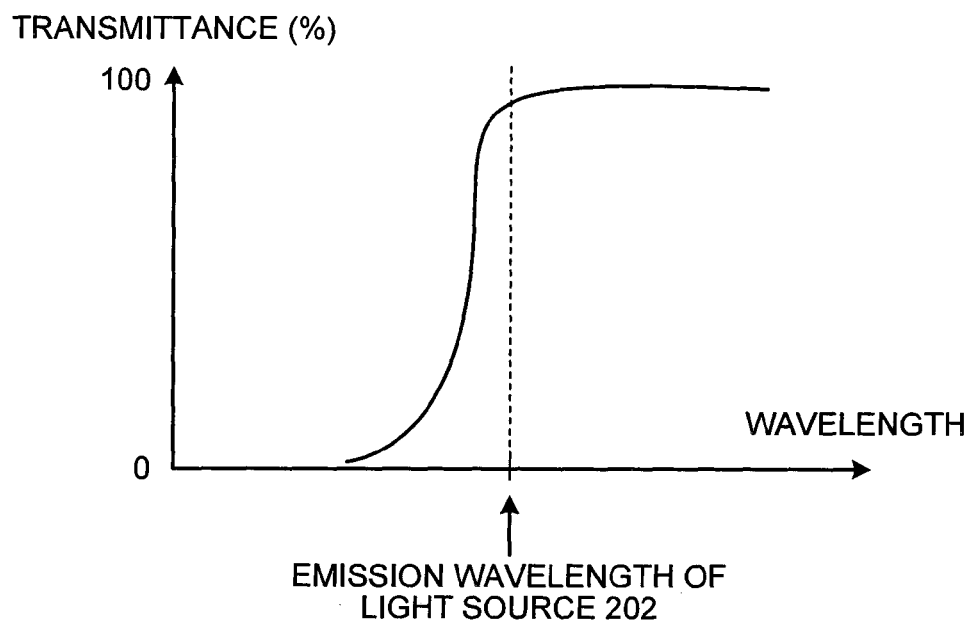
FIG. 6 is a graph illustrating the filter characteristics of a cutoff filter that is applicable for captured-image data for raindrop detection.
Figure 7:
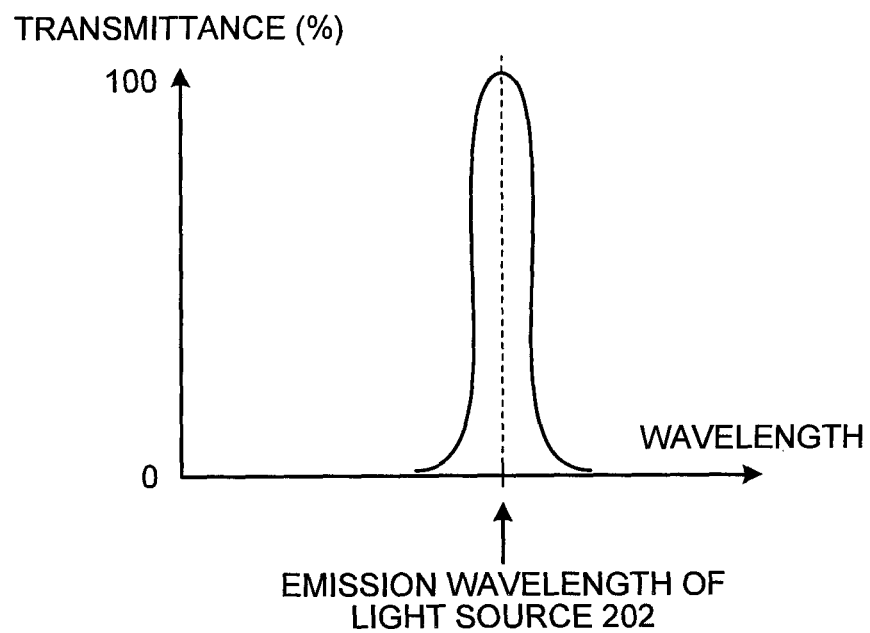
FIG. 7 is a graph illustrating the filter characteristics of a bandpass filter that is applicable for captured-image data for raindrop detection.

In that regard, in the present embodiment, the configuration is such that the light emitted by the light source 202 is received by the image sensor 206 via, for example, either a cutoff filter, which cuts of the light having shorter wavelengths than the emission wavelength of the light source 202 as illustrated in FIG. 6, or a bandpass filter, which has the transmittance peak almost matching to the emission wavelength of the light source 202 as illustrated in FIG. 7. With such a configuration, only after the light having the wavelengths other than the emission wavelength of the light source 202 is removed, the image sensor 206 receives the light. Hence, the amount of light that is emitted by the light source 202 and received by the image sensor 206 increases relative to the ambient light. As a result, even if the light source 202 does not have a large amount of luminescence, it becomes possible to distinguish between the light emitted by the light source 202 from the ambient light.

However, in the present embodiment, in addition to detecting the raindrops 203 attached to the windshield 105 from the captured-image data; the proceeding motor vehicles, the oncoming motor vehicles, and the white lines are also detected from the captured-image data. Thus, if the wavelength range other than the infrared wavelength light emitted by the light source 202 is removed with respect to all captured images, then the image sensor 206 becomes unable to receive light in the wavelength ranges required for the detection of the proceeding motor vehicles, the oncoming motor vehicles, and the white lines. That poses a problem for the detection of those objects. In that regard, in the present embodiment, image areas in the captured-image data are divided into raindrop detection image areas, which are used in detecting the raindrops 203 attached to the windshield 105, and motor vehicle detection image areas, which are used in detecting the proceeding motor vehicles, the oncoming motor vehicles, and the white lines. Moreover, with respect to the portion corresponding to only the raindrop detection image areas, a filter that cuts off the wavelength range other than the infrared wavelength light emitted by the light source 202 is disposed in the optical filter 205.

Figure 8:
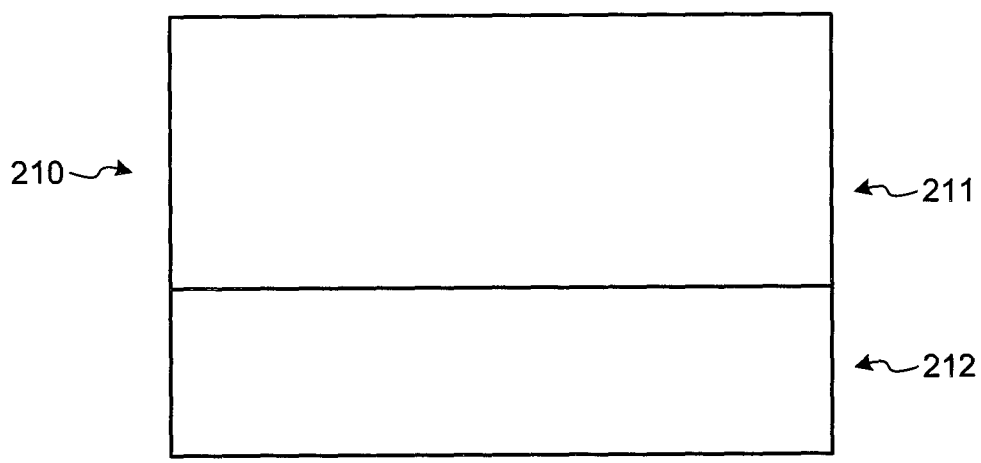
FIG. 8 is a front view of a pre-filter disposed in an optical filter of the imaging device.

FIG. 8 is a front view of a pre-filter 210 disposed in the optical filter 205.

Figure 9:
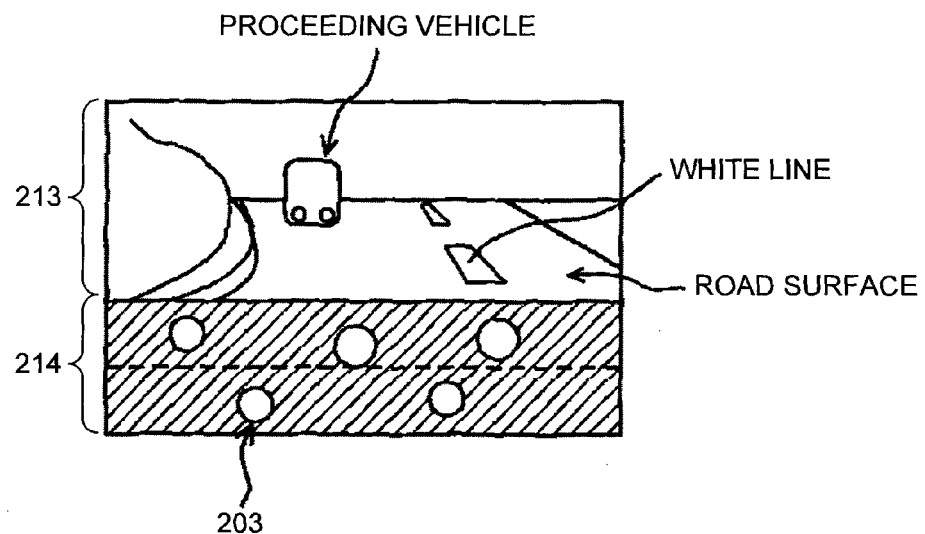
FIG. 9 is an explanatory diagram for explaining an example of an image based on captured-image data of the imaging device.

FIG. 9 is an explanatory diagram for explaining an example of an image in the captured-image data.

As illustrated in FIG. 3, the optical filter 205 has a structure in which the pre-filter 210 and a post-filter 220 are superposed in the light transmission direction. As illustrated in FIG. 8, the pre-filter 210 is segmented into an infrared light cutoff filter area 211, which is formed in the portion corresponding to a motor vehicle detection image area 213 that accounts for the upper two-thirds portion of a captured image, and an infrared light transmission filter area 212, which is formed in the portion corresponding to a raindrop detection image area 214 that accounts for the lower one-third portion of a captured image. As the infrared light transmission filter area 212, the cutoff filter illustrated in FIG. 6 or the bandpass filter illustrated in FIG. 7 is used.

In captured images; the headlamps of oncoming motor vehicles, the tail lamps of proceeding motor vehicles, and the white lines are often captured in the upper portion. In contrast, the immediate road surface to the own motor vehicle is captured usually in the lower portion of a captured image. Therefore, the information required for the identification of the headlamps of oncoming motor vehicles, the tail lamps of proceeding motor vehicles, and the white lines is available largely in the upper portion of captured images; and the information available in the lower portion of captured images is of small interest in such identification. Hence, from a single set of captured-image data, when detection of oncoming motor vehicles, proceeding motor vehicles, or the white lines is to be performed at the same time of performing detection of raindrops; then, as illustrated in FIG. 9, it is preferable to set the lower portion of a captured image as the raindrop detection image area 214; to set the remaining upper portion of the captured color area as the motor vehicle detection image area 213; and to accordingly perform area segmentation of the pre-filter 210.

If the imaging direction of the imaging device 200 is tilted downward, then there are times when the hood of the own motor vehicle enters the lower portion within the imaging area. In this case, the sunlight reflected from the hood of the own motor vehicle or the light emitted by the tail lamp of a proceeding motor vehicle and reflected from the hood of the own motor vehicle becomes ambient light; and inclusion of such ambient light in the captured-image data becomes responsible for false detection of the headlamps of oncoming motor vehicles, the tail lamps of proceeding motor vehicles, and the white lines. Even in such a case, in the present embodiment, since the cutoff filter illustrated in FIG. 6 or the bandpass filter illustrated in FIG. 7 is disposed at the portion corresponding to the lower portions of captured images; the sunlight reflected from the hood of the own motor vehicle or the light emitted by the tail lamp of a proceeding motor vehicle and reflected from the hood of the own motor vehicle is cut off. That enables achieving enhancement in the identification accuracy of the headlamps of oncoming motor vehicles, the tail lamps of proceeding motor vehicles, and the white lines.

Moreover, in the present embodiment, due to the characteristic feature of the imaging lens 204, the view in the imaging area and the image captured in the image sensor 206 are reversed in terms of the upper side and the lower side. As a result, in the case of setting the lower portion of the captured-image as the raindrop detection image area 214; the upper portion of the pre-filter 210 in the optical filter 205 is configured with the cutoff filter illustrated in FIG. 6 or the bandpass filter illustrated in FIG. 7.

Herein, at the time of detecting a proceeding motor vehicle, the tail lamp captured in the captured image is identified and the proceeding motor vehicle is detected. However, as compared to the headlamp of an oncoming motor vehicle, the light emitted by the tail lamp is smaller in amount. Moreover, there is also present a lot of ambient light such as the light of street lamps. Hence, highly accurate detection of a tail lamp is difficult to perform by referring only to brightness data. For that reason, during tail lamp identification, it becomes necessary to refer to spectral information and to identify the tail lamp on the basis of the amount of red light that is received. In that regard, in the present embodiment, as described later, a red filter or a cyan filter matching to the color of the tail lamp (i.e., a filter that transmits the wavelength band of only the color of the tail lamp) is disposed, and the amount of red light that is received is detected.

However, in the present embodiment, each light receiving element constituting the image sensor 206 has sensitivity to the light in the infrared wavelength band. Thus, when the image sensor 206 receives the light containing the infrared wavelength band, the captured image that is obtained becomes reddish in entirety. As a result, there are times when the red image portion corresponding to the tail lamp is difficult to identify. In that regard, in the present embodiment, in the pre-filter 210 of the optical filter 205, the location corresponding to the motor vehicle detection image area 213 is set as the infrared light cutoff filter area 211. With that, the infrared wavelength band gets cut off from that portion of the captured-image data which is used in tail lamp identification. That enables achieving enhancement in the tail lamp identification accuracy.

Figure 10:
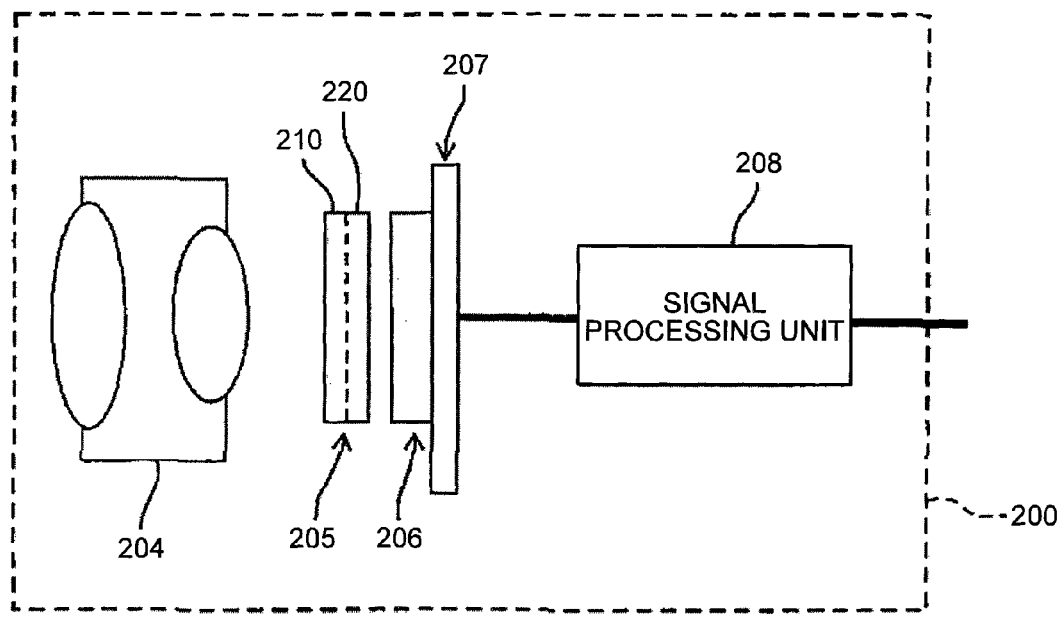
FIG. 10 is an explanatory diagram for explaining the details of the imaging device.

FIG. 10 is an explanatory diagram for explaining the details of the imaging device 200 according to the present embodiment.

The imaging device 200 is mainly configured with a sensor substrate 207 and a signal processing unit 208. The sensor substrate 207 includes the imaging lens 204, the optical filter 205, and the image sensor 206 that has a pixel array with a two-dimensional arrangement. The signal processing unit 208 generates captured-image data by converting analog electrical signals output by the sensor substrate 207 (i.e., the amount of light received by the light receiving elements of the image sensor 206) into digital electrical signals, and then outputs the captured-image data. The light from the imaging area containing a photographic subject (i.e., a target object for detection) passes through the imaging lens 204, passes through the optical filter 205, and is converted into electric signals according to the light intensity thereof in the image sensor 206. When the electric signals (analog signals) output from the image sensor 206 are received as input; the signal processing unit 208 outputs, as the captured-image data, digital signals indicating the brightness (luminance) of each pixel in the image sensor 206 as well as horizontal/vertical synchronization signals to the subsequent component.

Figure 11:
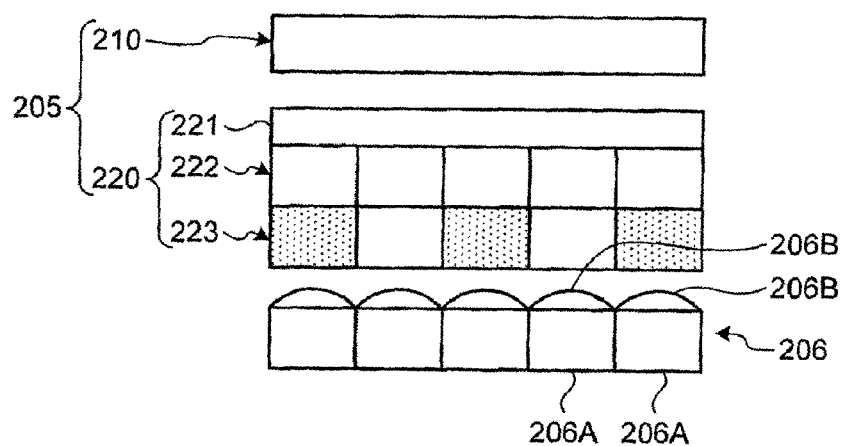
FIG. 11 is a schematic enlarged view of the optical filter and an image sensor of the imaging device when viewed from the orthogonal direction to the light transmission direction.

FIG. 11 is a schematic enlarged view of the optical filter 205 and the image sensor 206 when viewed from the orthogonal direction to the light transmission direction.

In the image sensor 206, a CCD (Charge Coupled Device) or a CMOS (Complementary Metal Oxide Semiconductor) is used as an image sensor, and photodiodes 206A are used as light receiving elements. The photodiodes 206A are arranged in a two-dimensional array on a pixel-by-pixel basis. In order to enhance the light collection efficiency of the photodiodes 206A, a microlens 206B is disposed on the light entering side of each photodiode 206A. Meanwhile, the sensor substrate 207 is formed by bonding the image sensor 206 to a PWB (printed wiring board) using the wire bonding method or the like.

The optical filter 205 is proximately-arranged to the surface of the image sensor 206 on which the microlenses 206B are disposed. As illustrated in FIG. 11, the post-filter 220 of the optical filter 205 has a laminate structure in which a polarization filter layer 222 and a spectral filter layer 223 are sequentially formed on a transparent filter substrate 221. Each of the polarization filter layer 222 and the spectral filter layer 223 are segmented into areas, each of which corresponds to one of the photodiodes 206A of the image sensor 206.

Although it is possible to have a configuration in which there is a clearance gap between the optical filter 205 and the image sensor 206, having a configuration in which the optical filter 205 is closely-attached to the image sensor 206 makes it easier to match the borders between the segmented areas of the polarization filter layer 222 and the segmented areas of the spectral filter layer 223 in the optical filter 205 with the borders between the photodiodes 206A of the image sensor 206. The optical filter 205 and the image sensor 206 can be attached together using a UV adhesive agent or by performing UV bonding or thermal compression bonding of the four side areas outside of the effective pixels while supporting the portion other than the effective pixel range, which is used in imaging, with a spacer.

Figure 12:
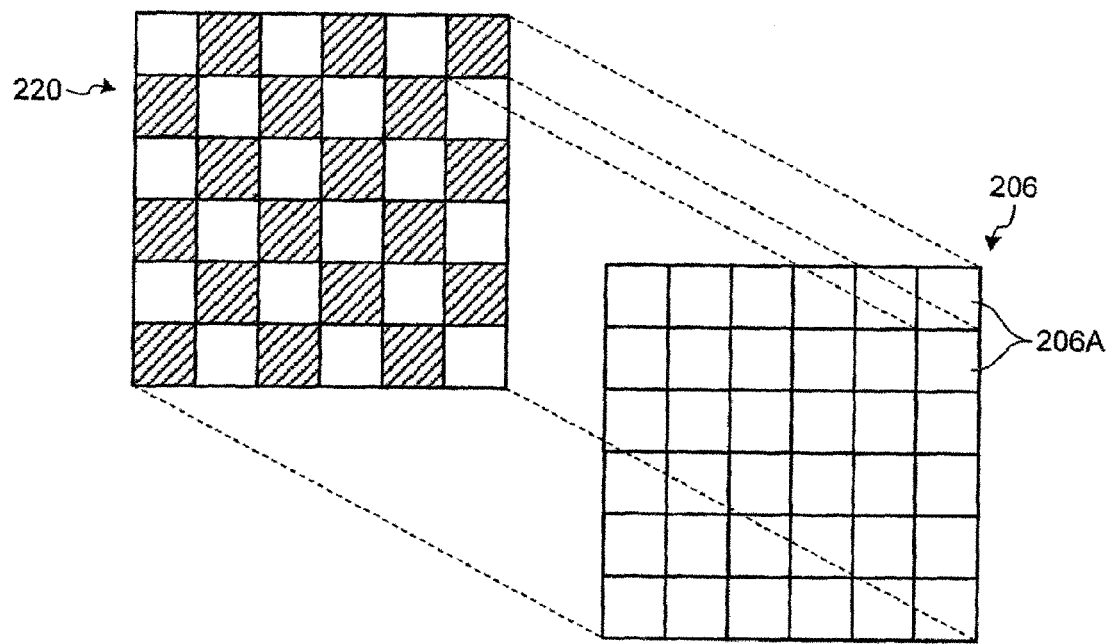
FIG. 12 is an explanatory diagram illustrating an area segmentation pattern of a polarization filter layer and a spectral filter layer of the optical filter.

FIG. 12 is an explanatory diagram illustrating an area segmentation pattern of the polarization filter layer 222 and the spectral filter layer 223 in the optical filter 205 according to the present embodiment.

Each of the polarization filter layer 222 and the spectral filter layer 223 has two types of areas. The polarization filter layer 222 has a first type area and a second type area formed corresponding to a single photodiode 206A of the image sensor 206, and the spectral filter layer 223 has a third type area and a fourth type area. Consequently, depending on the type of the areas of the polarization filter layer 222 and the spectral filter layer 223 through which the received light has passed, the amount of light received by each photodiode 206A of the image sensor 206 can be obtained as polarization information or spectral information.

Meanwhile, in the present embodiment, although the explanation is given on the premise that the image sensor 206 is configured with imaging elements for forming monochrome images, it is also possible to configure the image sensor 206 with imaging elements for forming color images. In the case of configuring the image sensor 206 with imaging elements for forming color images, the light transmission characteristics of each area of the polarization filter layer 222 as well as the spectral filter layer 223 can be adjusted according to the characteristics of a color filter pertaining to each imaging pixel of the imaging elements for forming color images.

First Configuration Example of Optical Filter

Herein, the explanation is given for a configuration example of the optical filter 205 according to the present embodiment (hereinafter, the present configuration example is referred to as "first configuration example"). In the following explanation of the optical filter 205, the explanation regarding the pre-filter 210 of the optical filter 205 is skipped and the explanation regarding only the post-filter 220 is given.

Figure 13:
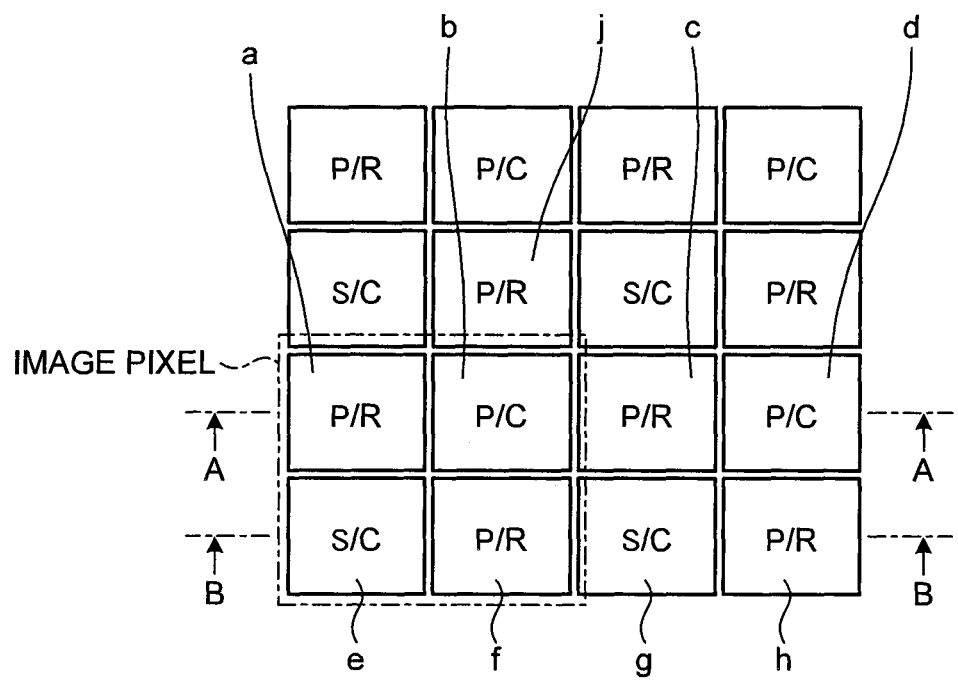
FIG. 13 is an explanatory diagram for explaining the contents of information (information regarding each imaging pixel) corresponding to the amount of light that has passed through the optical filter according to a first configuration example and that is received by each photodiode of the image sensor.

FIG. 13 is an explanatory diagram for explaining the contents of the information (information regarding each imaging pixel) corresponding to the amount of light that has passed through the optical filter 205 according to the first configuration example and that is received by each photodiode 206A of the image sensor 206.

Figure 14A:
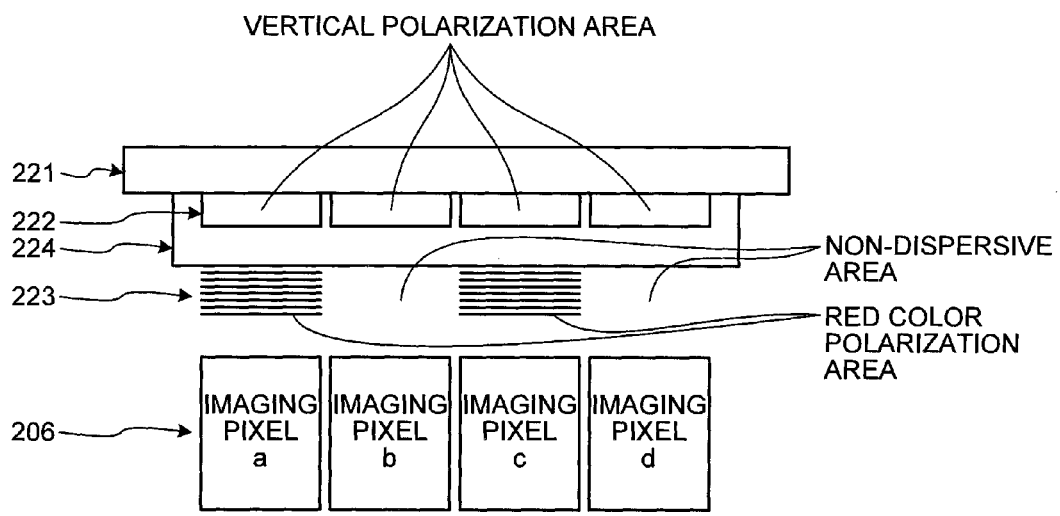
FIG. 14A is a cross-sectional view taken along line A-A illustrated in FIG. 13 for schematically illustrating the optical filter and the image sensor.

FIG. 14A is a cross-sectional view taken along line A-A illustrated in FIG. 13 for schematically illustrating the optical filter 205 and the image sensor 206.

Figure 14B:
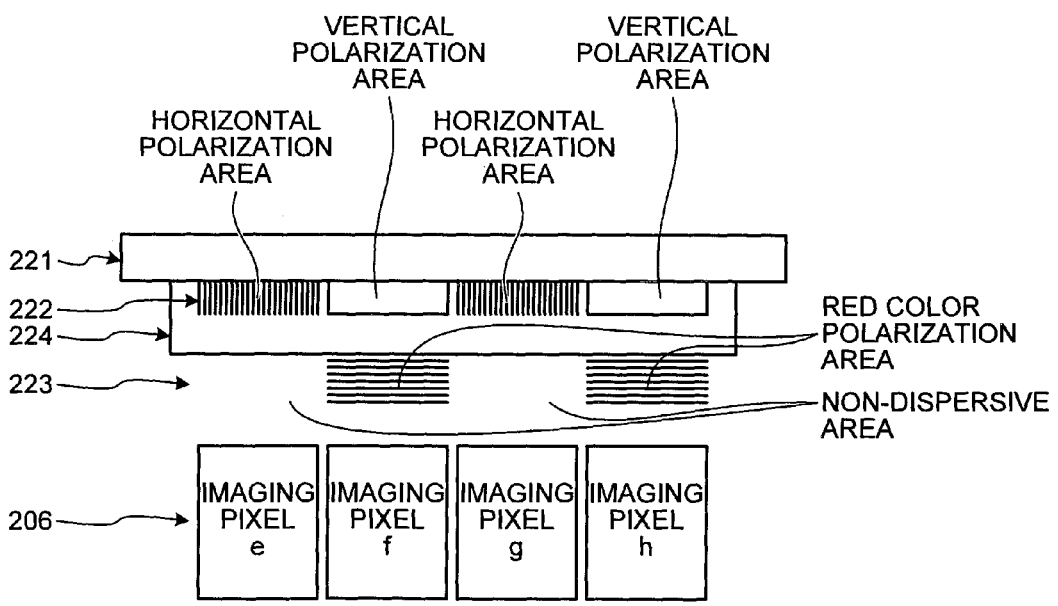
FIG. 14B is a cross-sectional view taken along line B-B illustrated in FIG. 13 for schematically illustrating the optical filter and the image sensor.

FIG. 14B is a cross-sectional view taken along line B-B illustrated in FIG. 13 for schematically illustrating the optical filter 205 and the image sensor 206.

As illustrated in FIGS. 14A and 14B, the optical filter 205 according to the first configuration example has a laminate structure in which the polarization filter layer 222 is firstly formed on the transparent filter substrate 221 and then the spectral filter layer 223 is formed on the polarization filter layer 222. Herein, the polarization filter layer 222 has a wire grid structure, and the top face in the lamination direction (the lower face illustrated in FIGS. 14A and 14B) becomes uneven in nature.

If an attempt is made to form the spectral filter layer 223 on such an uneven face, the spectral filter layer 223 also gets formed along the uneven face. That causes irregularity in the layer thickness of the spectral filter layer 223. As a result, there are times when the original spectral performance of the spectral filter layer 223 cannot be obtained. In that regard, in the optical filter 205 according to the present embodiment, the top face in the lamination direction of the polarization filter layer 222 is smoothened by filling it with a filling material, and then the spectral filter layer 223 is formed on the polarization filter layer 222.

As the filling material, it is possible to use any filling material that, when filled to smoothen the uneven face, does not interfere with the function of the polarization filter layer 222. In the present embodiment, a filling material not having the polarization function is used. Moreover, during the smoothening operation using a filling material, it is possible to suitably adopt the method of applying the filling material with the spin-on glass technology. However, that is not the only possible case.

In the first configuration example, the first type area of the polarization filter layer 222 is a vertical polarization area that selectively transmits only the vertical polarization components which oscillate parallel to columns of the imaging pixels of the image sensor 206 (i.e., oscillate in the vertical direction). The Second type area of the polarization filter layer 222 is a horizontal polarization area that selectively transmits only the horizontal polarization components which oscillate parallel to rows of the imaging pixels of the image sensor 206 (i.e., oscillate in the horizontal direction).

The third type area of the spectral filter layer 223 is a red spectral area that selectively transmits the light of only the red wavelength band (i.e., a specific wavelength band) included in the used wavelength bands that can pass through the polarization filter layer 222. The fourth type area of the spectral filter layer 223 is a non-dispersive area that transmits the light without selecting a wavelength. Meanwhile, in the first configuration example, as enclosed in a dashed-dotted line illustrated in FIG. 13, a total of four imaging pixels including two horizontally-adjacent imaging pixels and two vertically-adjacent imaging pixels (i.e., four imaging pixels "a", "b", "e", and "f") constitute a single image pixel in the captured-image data.

The imaging pixel "a" illustrated in FIG. 13 receives the light that has passed through the vertical polarization area (the first type area) in the polarization filter layer 222 of the optical filter 205 and through the red spectral area (the third type area) in the spectral filter layer 223 of the optical filter 205. Thus, the imaging pixel "a" receives a light P/R that indicates a light in the red wavelength band (illustrated as R in FIG. 13) of the vertical polarization component (illustrated as P in FIG. 13).

The imaging pixel "b" illustrated in FIG. 13 receives the light that has passed through the vertical polarization area (the first type area) in the polarization filter layer 222 of the optical filter 205 and through the non-dispersive area (the fourth type area) in the spectral filter layer 223 of the optical filter 205. Thus, the imaging pixel "b" receives a light P/C that indicates a light of the non-dispersive type (illustrated as C in FIG. 13) of the vertical polarization component P.

The imaging pixel "e" illustrated in FIG. 13 receives the light that has passed through the horizontal polarization area (the second type area) in the polarization filter layer 222 of the optical filter 205 and through the non-dispersive area (the fourth type area) in the spectral filter layer 223 of the optical filter 205. Thus, the imaging pixel "e" receives a light S/C that indicates a light of the non-dispersive type C of the horizontal polarization component (illustrated as S in FIG. 13).

The imaging pixel "f" illustrated in FIG. 13 receives the light that has passed through the vertical polarization area (the first type area) in the polarization filter layer 222 of the optical filter 205 and through the red spectral area (the third type area) in the spectral filter layer 223 of the optical filter 205. Thus, in an identical manner to the imaging pixel "a", the imaging pixel "f" receives the light P/R that indicates a light in the red wavelength band R of the vertical polarization component P.

With the configuration described above, according to the first configuration example, from the output signal of the imaging pixel "a" and the output signal of the imaging pixel "f", image data for one image pixel regarding a vertical polarization component image of red light is obtained; from the output signal of the imaging pixel "b", image data for one image pixel regarding a vertical polarization component image of non-dispersive light is obtained; and from the output signal of the imaging pixel "e", image data for one image pixel regarding a horizontal polarization component image of non-dispersive light is obtained. Thus, according to the first configuration example, with a single imaging operation, it becomes possible to obtain the following three types of captured-image data: a vertical polarization component image of red light; a vertical polarization component image of non-dispersive light; and a horizontal polarization component image of non-dispersive light.

In these types of captured-image data, the number of image pixels becomes smaller than the number of imaging pixels. Thus, in order to obtain images of a higher resolution, a commonly-known image interpolation technique can be used. For example, consider the case of obtaining a vertical polarization component image of red light that is of a higher resolution. In that case, regarding the image pixels corresponding to the imaging pixel "a" and the imaging pixel "f", the information of the vertical polarization component P of red light that is received at the imaging pixel "a" and at the imaging pixel "f" is used without modification. Moreover, regarding the image pixel corresponding to the imaging pixel "b"; for example, the average value of the imaging pixels "a", "c", "f", and "j" that surround the imaging pixel "b" is used as the information of the vertical polarization component of red light of that image pixel.

Moreover, in order to obtain a horizontal polarization component image of non-dispersive light that is of a higher resolution, regarding the image pixel corresponding to the imaging pixel "e", the information of the horizontal polarization component S of non-dispersive light received at the imaging pixel "e" is used without modification. Moreover, regarding the image pixels corresponding to the imaging pixels "a", "b", and "f"; either the average value of the imaging pixel "e" and an imaging pixel "g", which receive horizontal polarization components of non-dispersive light around the imaging pixels "a", "b", and "f", can be used or the same value as the imaging pixel "e" can be used.

The vertical polarization component images of red light obtained in the abovementioned manner can be used, for example, in identifying tail lamps. As far as the vertical polarization component images of red light are concerned, since the horizontal polarization component S is cut off, it becomes possible to obtain such red images that are free of disturbance factors caused by a high-intensity red light of the horizontal polarization component S such as the red light reflected from the road surface or the red light (reflected light) from the dashboard of the own motor vehicle 100. Hence, by using vertical polarization component images of red light in the identification of tail lamps, the tail lamp recognition rate can be enhanced.

The vertical polarization component images of non-dispersive light can be used, for example, in identifying white lines or headlamps of oncoming motor vehicles. As far as vertical polarization component images of non-dispersive light are concerned, since the horizontal polarization component S is cut off, it becomes possible to obtain such non-dispersive images that are free of disturbance factors caused by a high-intensity white light of the horizontal polarization component S such as the white light of a headlamp or a street lamp that is reflected from the road surface or the white light (reflected light) from the dashboard of the own motor vehicle 100. Hence, by using vertical polarization component images of non-dispersive light in the identification of white lines or headlamps of oncoming motor vehicles, the recognition rate can be enhanced. Particularly, it is commonly known that, on the road that is wet from the rain, the reflected light from the water surface covering the road surface has a large amount of the horizontal polarization component S. In such a situation, by using vertical polarization component images of non-dispersive light in the identification of white lines or headlamps of oncoming motor vehicles, it becomes possible to properly identify the white lines present under the water surface that is covering the road surface. That enables achieving enhancement in the recognition rate.

Meanwhile, if index values are obtained by comparing the pixels in a vertical polarization component image of non-dispersive light with the pixels in a horizontal polarization component image of non-dispersive light and if a comparison image is used in which the index values are treated as pixel values; then, as described later, it becomes possible to perform highly accurate identification of the following things: metal bodies present in the imaging area; dryness and wetness of the road surface; three-dimensional objects present in the imaging area, and white lines drawn on the road that is wet from the rain. Herein, for example, the comparison image can be one of the following images: a difference image in which pixel values point to the difference values between the pixel values of a vertical polarization component image of non-dispersive light and the pixel values of a horizontal polarization component image of non-dispersive light; a ratio image in which pixel values point to the ratios of the pixel values of a vertical polarization component image of non-dispersive light and the pixel values of a horizontal polarization component image of non-dispersive light; and a difference polarization degree image in which pixel values point to the ratios of the difference values of the pixel values of a vertical polarization component image of non-dispersive light and the pixel values of a horizontal polarization component image of non-dispersive light to the sum total of the pixel values in those images (difference polarization degrees).

Meanwhile, in the optical filter 205 according to the present embodiment; the post-filter 220, which includes the polarization filter layer 222 and the spectral filter layer 223 that are segmented into areas as illustrated in FIG. 13, is disposed more on the side of the image sensor 206 as compared to the pre-filter 210, which is segmented into two areas as illustrated in FIG. 8. However, alternatively, the pre-filter 210 can be disposed more on the side of the image sensor 206 as compared to the post-filter 220. Moreover, since the polarization filter layer 222 and the spectral filter layer 223, which are segmented into areas as illustrated in FIG. 13, are not essential in detecting raindrops; the configuration can be such that the polarization filter layer 222 and the spectral filter layer 223 are not formed at the location corresponding to the raindrop detection image area 214, that is, at the location opposite to the infrared light transmission filter area 212 of the pre-filter 210.

Second Configuration Example of Optical Filter

Explained below is another configuration example of the optical filter 205 according to the present embodiment (hereinafter, the present configuration example is referred to as "second configuration example").

Figure 15:
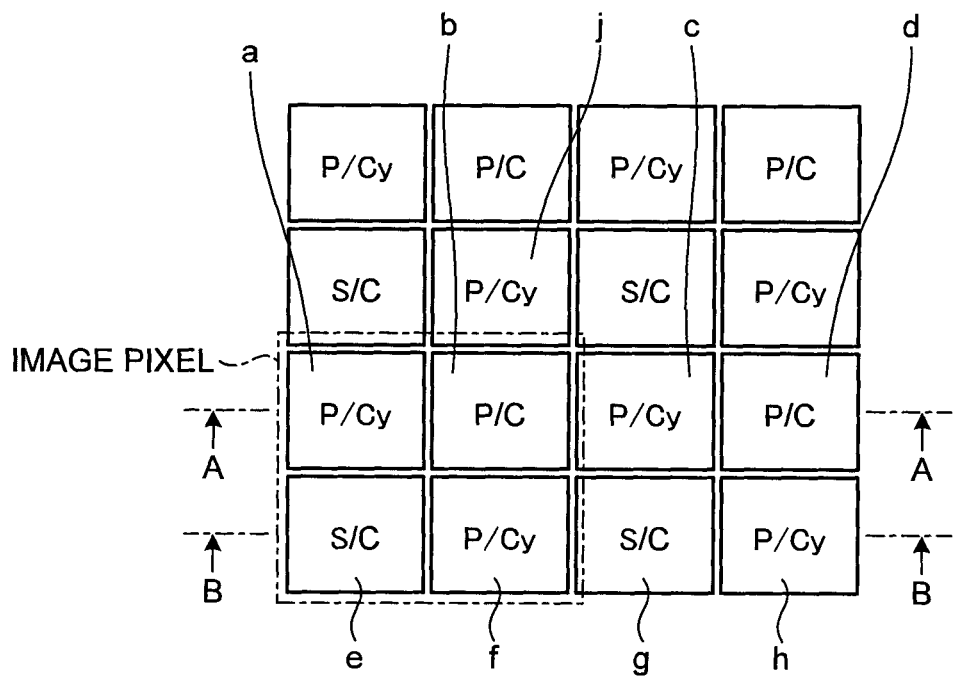
FIG. 15 is an explanatory diagram for explaining the contents of information (information regarding each imaging pixel) corresponding to the amount of light that has passed through the optical filter according to a second configuration example and that is received by each photodiode of the image sensor.

FIG. 15 is an explanatory diagram for explaining the contents of the information (information regarding each imaging pixel) corresponding to the amount of light that has passed through the optical filter 205 according to the second configuration example and that is received by each photodiode 206A of the image sensor 206.

Figure 16A:
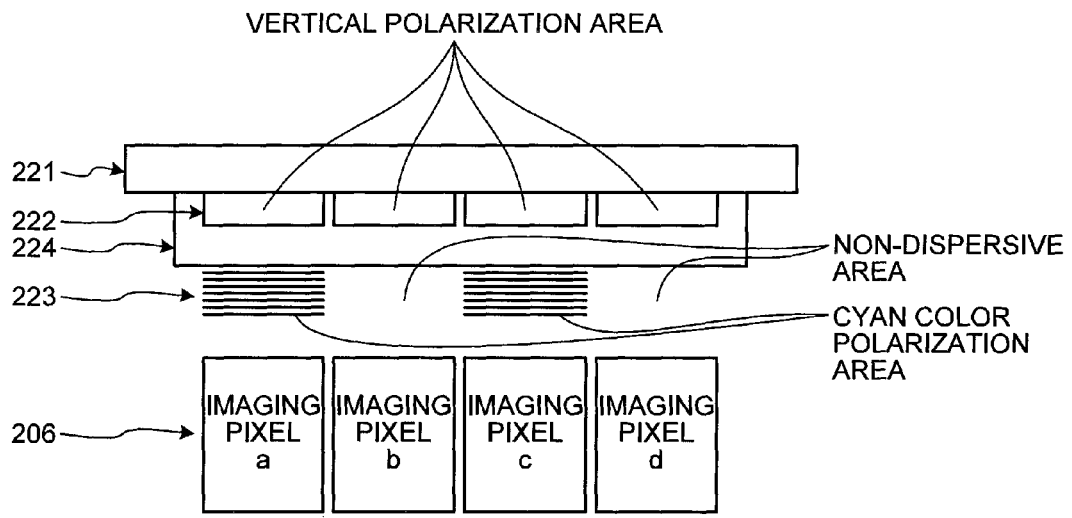
FIG. 16A is a cross-sectional view taken along line A-A illustrated in FIG. 15 for schematically illustrating the optical filter and the image sensor.

FIG. 16A is a cross-sectional view taken along line A-A illustrated in FIG. 15 for schematically illustrating the optical filter 205 and the image sensor 206.

Figure 16B:
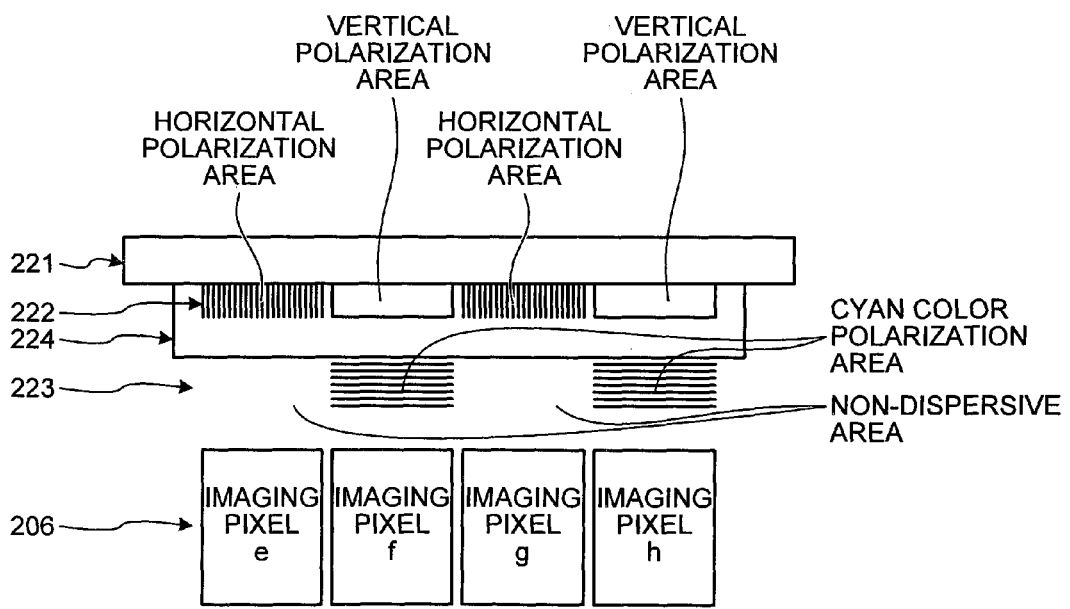
FIG. 16B is a cross-sectional view taken along line B-B illustrated in FIG. 15 for schematically illustrating the optical filter and the image sensor.

FIG. 16B is a cross-sectional view taken along line B-B illustrated in FIG. 15 for schematically illustrating the optical filter 205 and the image sensor 206.

In the first configuration example described above, the third type area of the spectral filter layer 223 is a red spectral area that selectively transmits the light of only the red wavelength band. In contrast, in the second configuration example, the third type area of the spectral filter layer 223 is a cyan spectral area that selectively transmits the light of only the cyan wavelength band (illustrated as Cy in FIG. 15) included in the used wavelength bands that can pass through the polarization filter layer 222. Apart from that point, the second configuration example has the same configuration as the first configuration example described above.

According to the second configuration example, from the output signal of the imaging pixel "a" and the output signal of the imaging pixel f, image data for one image pixel regarding a vertical polarization component image of cyan light is obtained; from the output signal of the imaging pixel "b", image data for one image pixel regarding a vertical polarization component image of non-dispersive light is obtained; and from the output signal of the imaging pixel "e", image data for one image pixel regarding a horizontal polarization component image of non-dispersive light is obtained. Thus, according to the second configuration example, with a single imaging operation, it becomes possible to obtain the following three types of captured-image data: a vertical polarization component image of cyan light; a vertical polarization component image of non-dispersive light; and a horizontal polarization component image of non-dispersive light.

According to the second configuration example, in an identical manner to the first configuration example described above, the three types of captured-image data obtained in the abovementioned manner enable achieving enhancement in the recognition rate of various targets for identification (such as tail lamps, headlamps, white lines, etc.).

Moreover, according to the second configuration example, it becomes possible to use a comparison image comparing between a vertical polarization component image of cyan light and a vertical polarization component image of non-dispersive light. By using such a comparison image, tail lamp identification can be performed with a high degree of accuracy. More particularly, regarding the light of a tail lamp, the amount of received light is small in the imaging pixels that have passed through a cyan spectral area have a small in amount, while the amount of received light is large the imaging pixels that have passed through a non-dispersive area. Hence, if a comparison image is generated to compare between a vertical polarization component image of cyan light and a vertical polarization component image of non-dispersive light, it becomes possible to increase the contrast between the tail lamp and the surrounding scenario portion. As a result, the tail lamp recognition rate can be enhanced.

In the second configuration example, the red spectral area using a red filter according to the first configuration example is replaced with the cyan spectral area using a cyan filter that transmits the light of only cyan color. Consequently, as compared to the first configuration example, the second configuration example provides a greater capability to identify between the tail lamp of a proceeding motor vehicle that is close to the own motor vehicle and a headlamp of an oncoming motor vehicle. If the red spectral area according to the first configuration example is used, regarding the tail lamp of a proceeding motor vehicle that is close to the own motor vehicle, there are times when the amount of light received through the red spectral area becomes so large that the light receiving sensitivity disappears thereby leading to saturation in the amount of light received through the red spectral area. As a result, there is a possibility of a decline in the tail lamp recognition rate for a proceeding motor vehicle that is close to the own motor vehicle. In contrast, when the cyan spectral area according to the second configuration example is used, regarding the tail lamp of a proceeding motor vehicle that is close to the own motor vehicle, there is no saturation in the amount of light received through the cyan spectral area. Hence, it becomes possible to prevent a decline in the tail lamp recognition rate for a proceeding motor vehicle that is close to the own motor vehicle.

Third Configuration Example of Optical Filter

Explained below is still another configuration example of the optical filter 205 according to the present embodiment (hereinafter, the present configuration example is referred to as "third configuration example").

Figure 17:
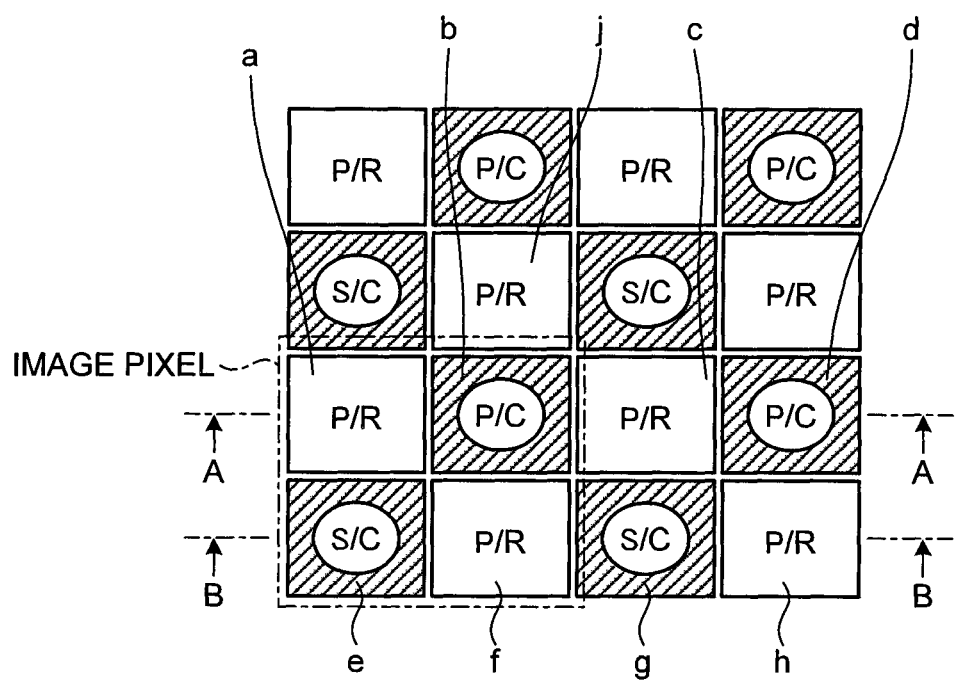
FIG. 17 is an explanatory diagram for explaining the contents of information (information regarding each imaging pixel) corresponding to the amount of light that has passed through the optical filter according to a third configuration example and that is received by each photodiode of the image sensor.

FIG. 17 is an explanatory diagram for explaining the contents of the information (information regarding each imaging pixel) corresponding to the amount of light that has passed through the optical filter 205 according to the third configuration example and that is received by each photodiode 206A of the image sensor 206.

Figure 18A:
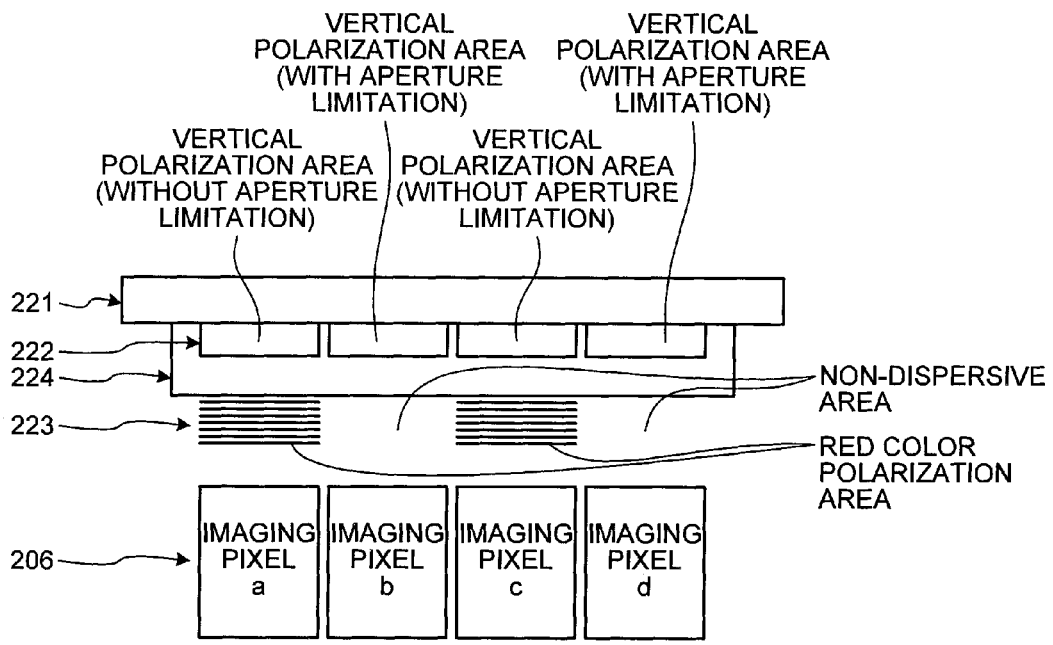
FIG. 18A is a cross-sectional view taken along line A-A illustrated in FIG. 17 for schematically illustrating the optical filter and the image sensor.

FIG. 18A is a cross-sectional view taken along line A-A illustrated in FIG. 17 for schematically illustrating the optical filter 205 and the image sensor 206.

Figure 18B:
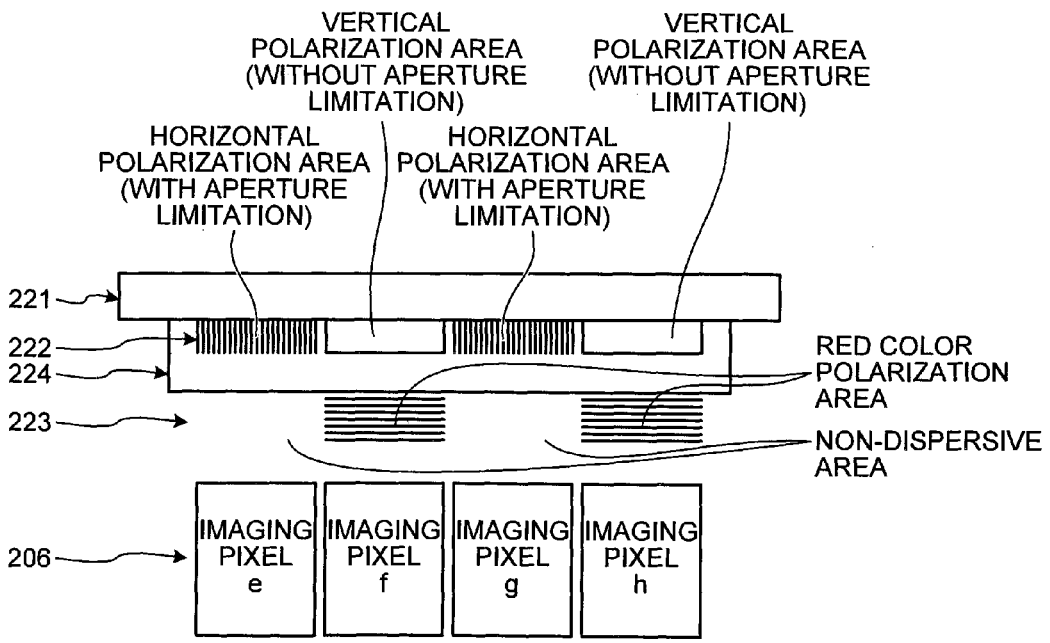
FIG. 18B is a cross-sectional view taken along line B-B illustrated in FIG. 17 for schematically illustrating the optical filter and the image sensor.

FIG. 18B is a cross-sectional view taken along line B-B illustrated in FIG. 17 for schematically illustrating the optical filter 205 and the image sensor 206.

In the third configuration example, the area segmentation configuration of the polarization filter layer 222 and the spectral filter layer 223 is identical to the first configuration example described above. However, in the third configuration example, corresponding to the non-dispersive area of the spectral filter layer 223, an aperture limiting unit is disposed for limiting the amount of received light. Thus, according to the third configuration example, in an identical manner to the first configuration example described above, with a single imaging operation, it becomes possible to obtain the following three types of captured-image data: a vertical polarization component image of red light; a vertical polarization component image of non-dispersive light; and a horizontal polarization component image of non-dispersive light. However, in the third configuration example, the vertical polarization component images of non-dispersive light and the horizontal polarization component images of non-dispersive light are generated with a smaller amount of received light as compared to the first configuration example described above.

Figure 19:
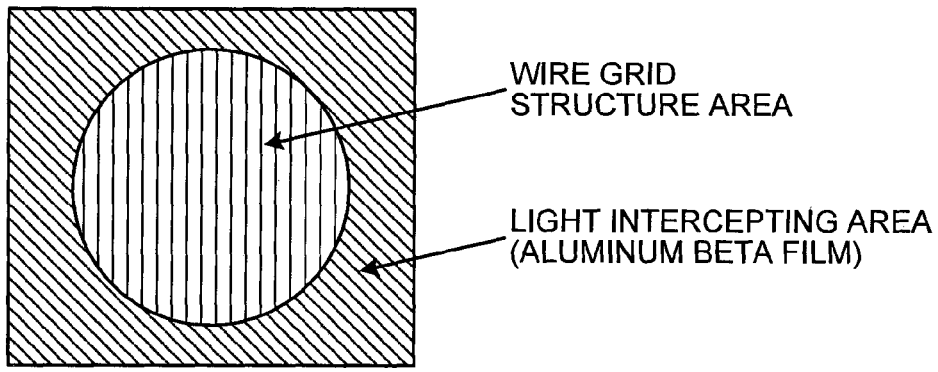
FIG. 19 is an explanatory diagram for explaining an exemplary configuration for limiting the amount of received light passing through the non-dispersive area of the spectral filter layer of the optical filter.
Figure 20:
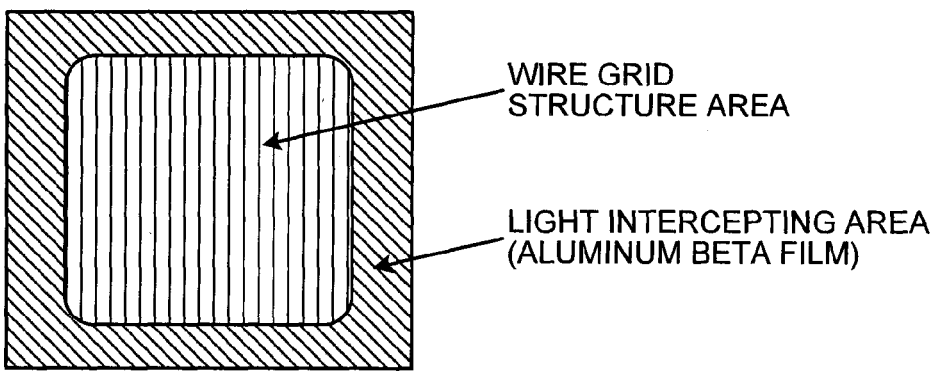
FIG. 20 is an explanatory diagram for explaining another exemplary configuration for limiting the amount of received light passing through the non-dispersive area of the spectral filter layer of the optical filter.

As far as the configuration for limiting the amount of received light passing through the non-dispersive area of the spectral filter layer 223 is concerned; the following structure explained with reference to FIG. 19 can be considered: corresponding to the non-dispersive area of the spectral filter layer 223, a round wire grid structure is formed at the central part of imaging pixels of the polarization filter layer 222; and the surrounding portion of the round wire grid structure is formed to be an aluminum film. With such a structure, the light gets intercepted at the aluminum film. Hence, depending on the size (aperture ratio) of the area in which the wire grid structure is formed, it becomes possible to limit the amount of received light passing through the non-dispersive area of the spectral filter layer 223. Meanwhile, the area for forming the wire grid structure need not be round as illustrated in FIG. 19. Alternatively, the area for forming the wire grid structure can be squarish in shape as illustrated in FIG. 20. In the case of forming a shape having corners as illustrated in FIG. 20, having roundish corners makes it easier to achieve the shape size by means of etching, for example.

In order to form the polarization filter layer 222 having the wire grid structure, a common manufacturing method includes, for example, forming an aluminum film in a uniform manner on the filter substrate 221 and then partially removing the aluminum film by means of etching to obtain the wire grid structure. In the third configuration example in which the aperture is limited by forming a light interception area made of aluminum surrounding the wire grid structure; while forming the wire grid structure, the aperture can be limited by performing processing to ensure that the aluminum film remains intact surrounding the wire grid structure. With that, as compared to the case of performing aperture limiting processing independent of the polarization filter layer 222, it becomes possible to simplify the manufacturing process.

Figure 21:
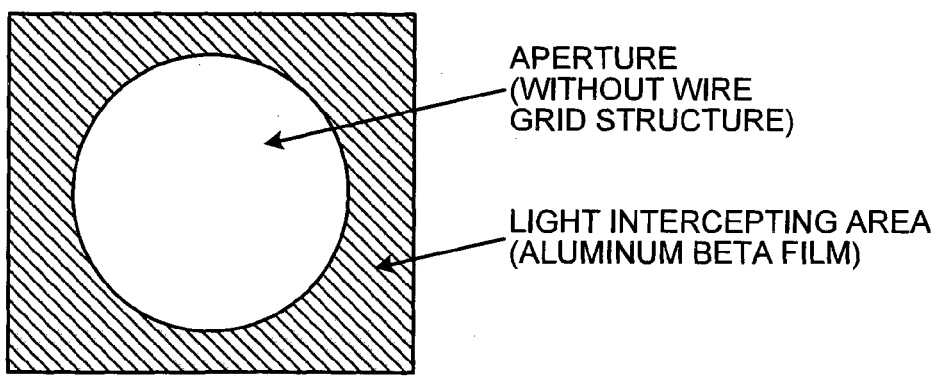
FIG. 21 is an explanatory diagram for explaining still another exemplary configuration for limiting the amount of received light passing through the non-dispersive area of the spectral filter layer of the optical filter.

Of course, an aperture limiting layer as illustrated in FIG. 21 can be formed independent of the polarization filter layer 222. In that case, no wire grid structure is formed in the central part of imaging pixels of the aperture limiting layer. Thus, the aperture limiting layer serves as an aperture through which the light passes without any interception.

Figure 22:
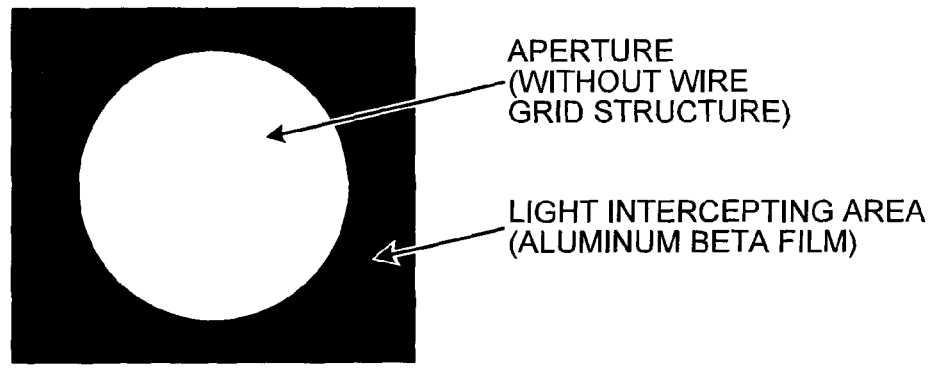
FIG. 22 is an explanatory diagram for explaining still another exemplary configuration for limiting the amount of received light passing through the non-dispersive area of the spectral filter layer of the optical filter.
Figure 23:
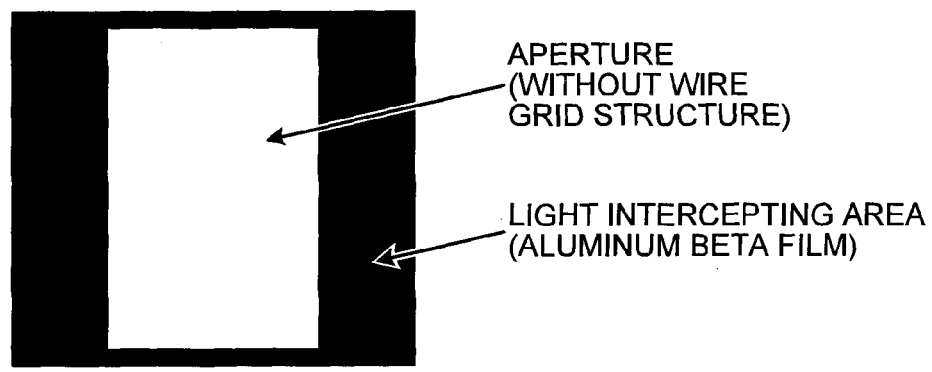
FIG. 23 is an explanatory diagram for explaining still another exemplary configuration for limiting the amount of received light passing through the non-dispersive area of the spectral filter layer of the optical filter.

Meanwhile, the light interception area used in limiting the aperture is not limited to a reflective film such as the aluminum film mentioned above. Alternatively, it is also possible to form, for example, a light absorbing film. As an example, as illustrated in FIG. 22, it is also possible to form the light interception area with a black resist film. In that case too, the light interception area need not be round as illustrated in FIG. 22, but can be, for example, squarish in shape as illustrated in FIG. 23. In the case of forming a shape having corners as illustrated in FIG. 23, having roundish corners makes it easier to achieve the shape size by means of etching, for example.

Figure 24:
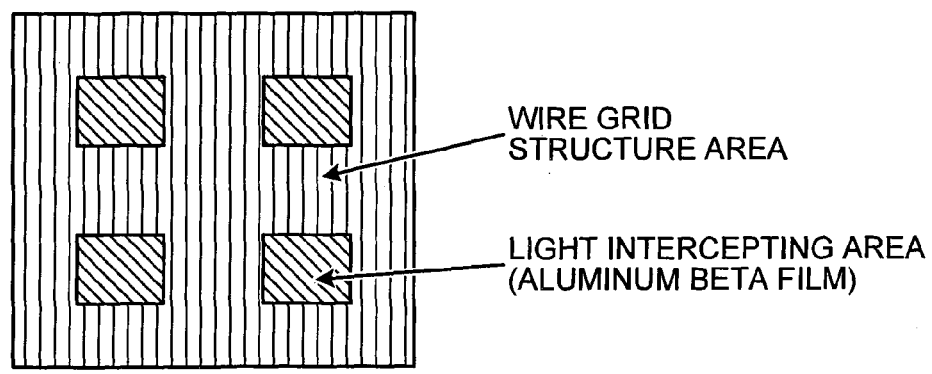
FIG. 24 is an explanatory diagram for explaining still another exemplary configuration for limiting the amount of received light passing through the non-dispersive area of the spectral filter layer of the optical filter.

Moreover, it is not necessary that a single imaging pixel has only a single light transmitting aperture formed. Alternatively, a single imaging pixel can have a plurality of apertures or wire grid structure areas formed. Regarding the light interception area too, it is not necessary that a single imaging pixel has only a single light interception area. Alternatively, a single imaging pixel can have a plurality of light interception areas. Particularly, a light interception area need not be formed in the surrounding part of imaging pixels. Alternatively, for example, as illustrated in FIG. 24, in the wire grid structure, aluminum films can be arranged in a discrete manner.

In the third configuration example, it becomes possible to obtain the following three types of captured-image data: a vertical polarization component image of red light identical to the first configuration example; a vertical polarization component image of non-dispersive light having limitation on the amount of received light as compared to the first configuration example; and a horizontal polarization component image of non-dispersive light having limitation on the amount of received light as compared to the first configuration example. In the third configuration example, proceeding motor vehicles are detected by referring to the result of identifying tail lamps using vertical polarization component images of red light; while oncoming motor vehicles are detected by referring to the result of identifying headlamps using vertical polarization component images of non-dispersive light or horizontal polarization component images of non-dispersive light. Usually, two lamps that are separated by a certain distance in the horizontal direction form a single pair of tail lamps or a single pair of headlamps. Hence, at the time of detecting a proceeding motor vehicle or an oncoming motor vehicle, when the image portions of two tail lamps or two headlamps in a captured image are separated by a certain distance, the pair of tail lamps is recognized to be of a proceeding motor vehicle or the pair of headlamps is recognized to be of an oncoming motor vehicle. At that time, the amount of light emitted by headlamps is greater than the amount of light emitted by tail lamps. For that reason, if the light receiving sensitivity is set to properly receive the light emitted by tail lamps, then it leads to saturation in the amount of light received from headlamps and the image area recognized as a single pair of headlamps expands. As a result, the two headlamp image areas that should originally be recognized separately get recognized as an integrated image area. Therefore, the image areas of headlamps are not properly recognized, which results in a decline in the recognition rate of oncoming motor vehicles. In contrast, if the light receiving sensitivity is set to properly receive the light emitted by headlamps, then it leads to a shortage in the amount of light received from tail lamps. Therefore, the image areas of tail lamps are not properly recognized, which results in a decline in the recognition rate of proceeding motor vehicles.

According to the third configuration example, the vertical polarization component images of non-dispersive light and the horizontal polarization component images of non-dispersive light that are used in the identification of headlamps are subjected to aperture limiting with the aim of limiting the amount of received light. Hence, even if the light receiving sensitivity is set in accordance to tail lamps that are identified with the use of vertical polarization component images of red light, saturation is prevented from occurring in the amount of light received from headlamps. As a result, it becomes possible to individually identify the image area of each headlamp. Hence, a decline is prevented from occurring in the recognition rate of oncoming motor vehicles.

Meanwhile, identification of tail lamps as well as identification of headlamps can be performed, for example, by switching between the light receiving sensitivities for capturing images separately and by identifying tail lamps and headlamps from the captured images. However, in this case, not only a control mechanism for switching between light receiving sensitivities becomes necessary, but also the frame rate of the captured image data decreases to half. In that regard, according to the third configuration example, no such issues arise and identification of tail lamps as well as identification of headlamps can be performed.

Fourth Configuration Example

Explained below is still another configuration example of the optical filter 205 according to the present embodiment (hereinafter, the present configuration example is referred to as "fourth configuration example").

As described above, the polarization filter layer 222 formed in the post-filter 220 of the optical filter 205 is subjected to area segmentation in the units of imaging pixels, and is segmented a the vertical polarization area (first type area) that selectively transmits only the vertical polarization component P and a horizontal polarization area (second type area) that selectively transmits only the horizontal polarization component S. With that, based on the image data of imaging pixels that receive the light which has passed through the vertical polarization area, it becomes possible to obtain a vertical polarization component image having the horizontal polarization component S removed therefrom. Similarly, based on the image data of imaging pixels that receive the light which has passed through the horizontal polarization area, it becomes possible to obtain a horizontal polarization component image having the vertical polarization component P removed therefrom.

If the windshield 105 has a flat face; then, by properly setting the polarization direction (transmission axis) of the vertical polarization area or the horizontal polarization area with respect to the face of the windshield 105, it becomes possible to obtain vertical polarization component images or horizontal polarization component images from which the reflection onto the windshield 105 is properly removed. However, generally, the windshield 105 of a motor vehicle is not only tilted downward anteriorly for the purpose of enhancement in the aerodynamic characteristics but also has a large curvature posteriorly in the left-right direction from the central part toward both ends. For that reason, when the polarization direction (transmission axis) of the vertical polarization area or the horizontal polarization area in the polarization filter layer 222 of the optical filter 205 is uniform in the area at any location; then, for example, even if the reflection from the windshield 105 is properly removed at the central part of captured images, there are times when reflection from the windshield 105 is not removed at the end parts of captured images.

Figure 25:
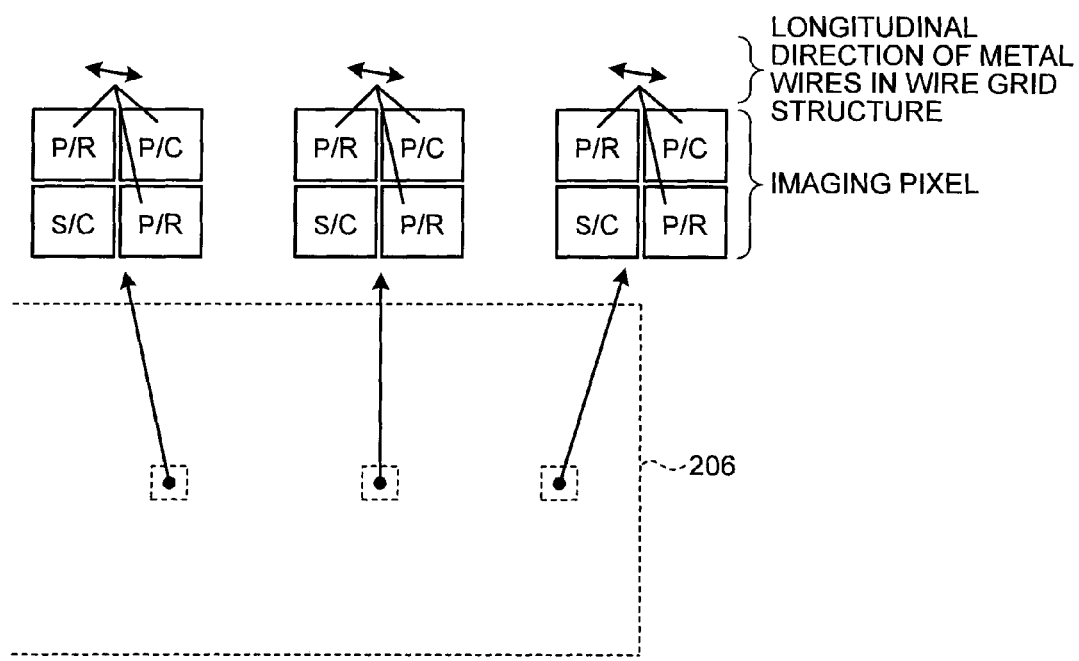
FIG. 25 is an explanatory diagram illustrating the longitudinal direction of metal wires of a wire grid structure in the polarization filter layer of the optical filter according to a fourth configuration example.

FIG. 25 is an explanatory diagram illustrating the longitudinal direction of metal wires of the wire grid structure in the polarization filter layer 222 of the optical filter 205 according to the fourth configuration example.

In the fourth configuration example, the area segmentation structure of the polarization filter layer 222 as well as the spectral filter layer 223 is identical to that explained in the first configuration example. However, in the fourth configuration example, the polarization direction (transmission axis) of the polarization filter layer 222 is not uniform. More particularly, as illustrated in FIG. 25, the vertical polarization area of the polarization filter layer 222 is formed in such a way that closer the vertical polarization area to an end in horizontal direction of the polarization filter layer 222, greater is the angle between the polarization direction (transmission axis) of the polarization filter layer 222 and the vertical direction in tune with the curvature of the windshield 105. That is, in the fourth configuration example, the polarization filter layer 222 is formed in such a way that closer the vertical polarization area to an end in the horizontal direction, greater is the angle between the longitudinal direction of the metal wires of the wire grid structure and the horizontal direction. In the present embodiment, since the vertical polarization area is formed with the wire grid structure, it becomes possible to form a number of areas having different polarization directions in the miniscule units of imaging pixels.

Details of Constituent Elements of Optical Filter

Explained below are the details of the constituent elements of the post-filter 220 of the optical filter 205. The filter substrate 221 is formed with a transparent material such as glass, sapphire, or crystal that can transmit the light of the used bands (in the present embodiment, visual light range and infrared region). In the present embodiment; glass, particularly, quartz glass (having refractive index of 1.46) or tempax glass (having refractive index of 1.51) that is inexpensive and durable can be suitably used.

Figure 26:
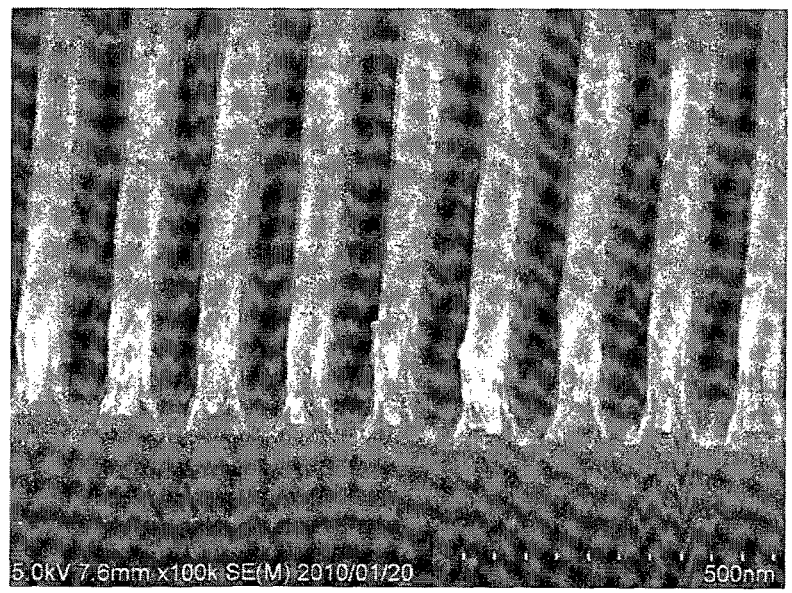
FIG. 26 is an enlarged view of the wire grid structure constituting the polarization filter layer.

The polarization filter layer 222 formed on the filter substrate 221 is configured with a polarizer that is formed using a wire grid structure illustrated in FIG. 26. In the wire grid structure, metal wires (conductive materials) that are made of a metal such as aluminum and that extend in a particular direction are arranged with a specific pitch. The wire pitch in the wire grid structure is set to be sufficiently small (for example, equal to or smaller than half) as compared to the wavelength band of the incident light. Because of that, almost all of the light of electrical field vector components oscillating parallel to the longitudinal direction of the metal wires gets reflected; and almost all of the light of electrical field vector components oscillating orthogonal to the longitudinal direction of the metal wires is transmitted. Hence, the polarizer can be used to produce single-polarization.

Regarding the polarizer having the wire grid structure, generally, an increase in the cross-sectional area of the metal wires leads to an increase in the extinction ratio. Moreover, in metal wires having a predetermined width or more with respect to the period width, there is a decrease in the transmittance. Furthermore, if the cross-sectional shape orthogonal to the longitudinal direction of the metal wires is tapered, there is less transmittance and less wavelength dispersibility of polarization degree in wideband, thereby indicating a high extinction ratio.

In the present embodiment, by forming the polarization filter layer 222 with the wire grid structure, following effects can be achieved.

The wire grid structure can be formed by making use of the widely-known semiconductor manufacturing process. More particularly, after an aluminum thin film is vapor-deposited on the filter substrate 221, patterning is performed followed by the formation of a subwavelength structure of the wire grid using a method such as metal etching. By performing such a manufacturing process, the polarization direction (polarization axis), that is, the longitudinal direction of the metal wires can be adjusted corresponding to the size (of few μm) of imaging pixels of the image sensor 206. With that, as described in the present embodiment, it becomes possible to prepare the polarization filter layer 222 in which the longitudinal direction of the metal wires, that is, the polarization direction (polarization axis) is altered in the units of imaging pixels.

Moreover, since the wire grid structure is manufactured using a metallic material such as aluminum, a high heat resistance is achieved. Hence, there is also the advantage that the wire grid structure can be suitably used in a high temperature environment such as the inside of a motor vehicle that is likely to get hot.

A filling material 224 that is used to even out the top face in the lamination direction of the polarization filter layer 222 is filled in the depressed portions in between the metal wires of the polarization filter layer 222. As the filling material 224, it is possible to suitably use an inorganic material having a smaller refractive index or the same refractive index as compared to the refractive index of the filter substrate 221. In the present embodiment, the filling material 224 is formed so as to also cover the top face in the lamination direction of the wire metal portion of the polarization filter layer 222.

As a specific material to be used for the filling material 224, it is desirable to use a material with a low refractive index as close as possible to the refractive index of air (refractive index=1), so that there is no degradation in the polarization property of the polarization filter layer 222. For example, it is desirable to use porous ceramics that is made by dispersing minute holes in ceramics. More particularly, the examples of such porous ceramics are porous silica ($SiO_2$), porous magnesium fluoride (MgF), and porous aluminum oxide ($Al_2O_3$). Herein, the extent of lowness in the refractive index depends on the number or the size of holes in ceramics (i.e., depends on porosity). When the filter substrate 221 contains silica crystals or glass as the major constituent, it is possible to suitably use porous silica (n=1.22 to 1.26).

As the method of forming the filling material 224, it is possible to suitably use the SOG (Spin On Glass) technique. More particularly, a solvent made by dissolving silanol (Si($OH)_4$) in alcohol is spin-coated on the polarization filter layer 222 that is formed on the filter substrate 221. Then, the solvent components are volatilized by means of thermal treatment, and silanol itself is subjected to dehydration polymerization reaction. Such a process is followed to form the filling material 224.

The polarization filter layer 222 is a wire grid structure of the subwavelength size and is weak in terms of mechanical strength. Thus, the metal wires get damaged even with a slight external force. Meanwhile, since it is desirable that the optical filter 205 according to the present embodiment is closely-attached to the image sensor 206, there is a possibility that the optical filter 205 and the image sensor 206 make contact with each other during the manufacturing stages. In that regard, in the present embodiment, the top face in the lamination direction of the polarization filter layer 222, that is, the face of the polarization filter layer 222 on the side of the image sensor 206 is covered by the filling material 224. Hence, even when that top face comes in contact with the image sensor, the wire grid structure is prevented from getting damaged.

Moreover, as described in the present embodiment, by filling the depressed portions in between the metal wires of the wire grid structure of the polarization filter layer 222 with the filling material 224, it becomes possible to prevent foreign substances from entering the depressed portions.

Meanwhile, in the present embodiment, the spectral filter layer 223 that is laminated on the filling material 224 does not have any protective layer, such as the filling material 224, formed thereon. That is because of the following reason. The experiments performed by the inventor(s) of the present invention indicated that, even if the spectral filter layer 223 makes contact with the image sensor 206, there is no damage that can affect the captured images. Hence, formation of the protective layer is omitted with the preference given to the reduction in cost. Moreover, on the one hand, the metal wires (salient portions) of the polarization filter layer 222 are low in height at equal to or lower than half of the used wavelength; and, on the other hand, the filter layer portion (salient portion) of the spectral filter layer 223 which has the red spectral area or the cyan spectral area formed thereon is either equal or about severalfold in height than the used wavelength. As the filling material 224 goes on increasing in thickness, it becomes more difficult to secure the evenness of the top face thereof, thereby affecting the characteristics of the optical filter 205. Hence, there is a limit to increasing the thickness of the filling material 224. For that reason too, in the present embodiment, the spectral filter layer 223 is not covered by any filling material.

Figure 27:
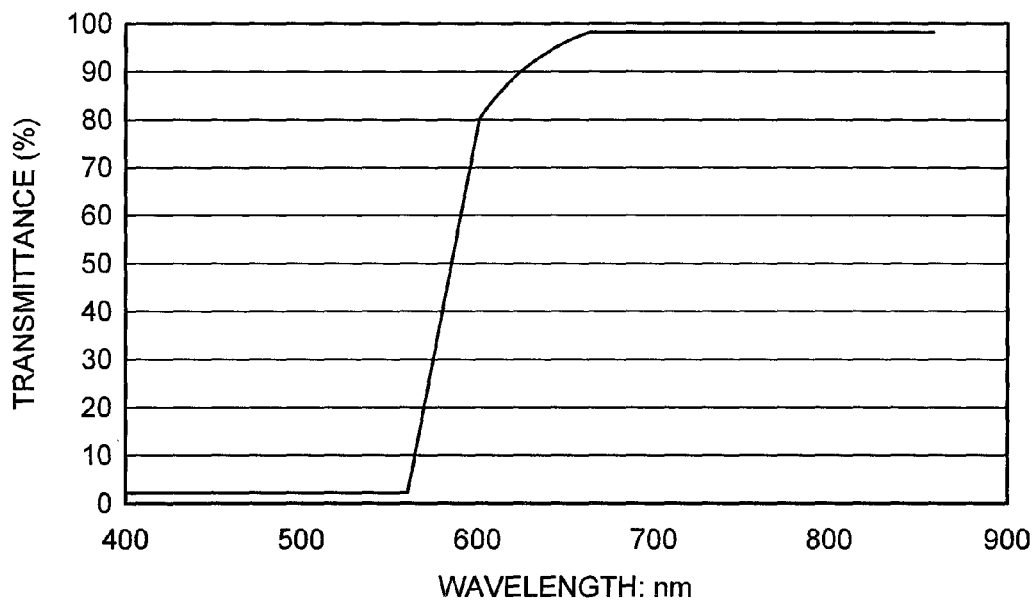
FIG. 27 is a graph illustrating the filter characteristics of a cutoff filter that is applicable in the spectral filter layer.

In the present embodiment, the filter layer portion of the spectral filter layer 223 which has the red spectral area or the cyan spectral area formed thereon is manufactured in the form of a multi-layer film structure in which thin films of high refractive index and thin films of low refractive index are alternately superposed. With such as a multi-layer film structure; making use of light interference enables to have a high degree of freedom in setting the spectral transmittance, and superposing multiple layers of thin films enables achieving reflectance close to 100% with respect to a specific wavelength (such as the wavelength band excluding red color). In the present embodiment, the used wavelength range of captured image data indicates the substantially visible light wavelength band (wavelength bands of visible light and infrared light). Therefore, the image sensor 206 having sensitivity in that used wavelength range is selected; and a cutoff filter as illustrated in FIG. 27 is formed that has the transparent wavelength of the multi-layer film portion set to, for example, 600 nm or more and that reflects the remaining wavelength band.

Such a cutoff filter can be obtained by manufacturing a multi-layer film that has a configuration such as "substrate/(0.125L0.25H0.125L)p/medium A)" in that order from the lower side in the lamination direction of the optical filter 205. Herein, "substrate" points to the filling material 224 described above. Moreover, "0.125L" indicates that nd/λ is set to 1L in the layer thickness notation method of a low refractive index material (for example, $SiO_2$), and thus the film of "0.125L" is a film of a low refractive index material having such a film thickness that the light path length becomes one-eighth of the wavelength. Furthermore, "n" represents the refractive index, "d" represents the thickness, and "λ" represents the cutoff wavelength. In an identical manner, "0.25H" indicates that nd/λ is set to 1H in the layer thickness notation method of a high refractive index material (for example, $TiO_2$), and thus the film of "0.25H" is a film of a high refractive index material having such a film thickness that the light path length becomes one-fourth of the wavelength. Moreover, "p" represents the number of times of repeating (superposing) the combination of films given inside the brackets. Greater the value of "p", greater is the extent to which the effect of ripples can be controlled. Meanwhile, the medium "A" points to the resin or the bonding adhesive that enables close bonding with the air or the image sensor 206.

Figure 28:
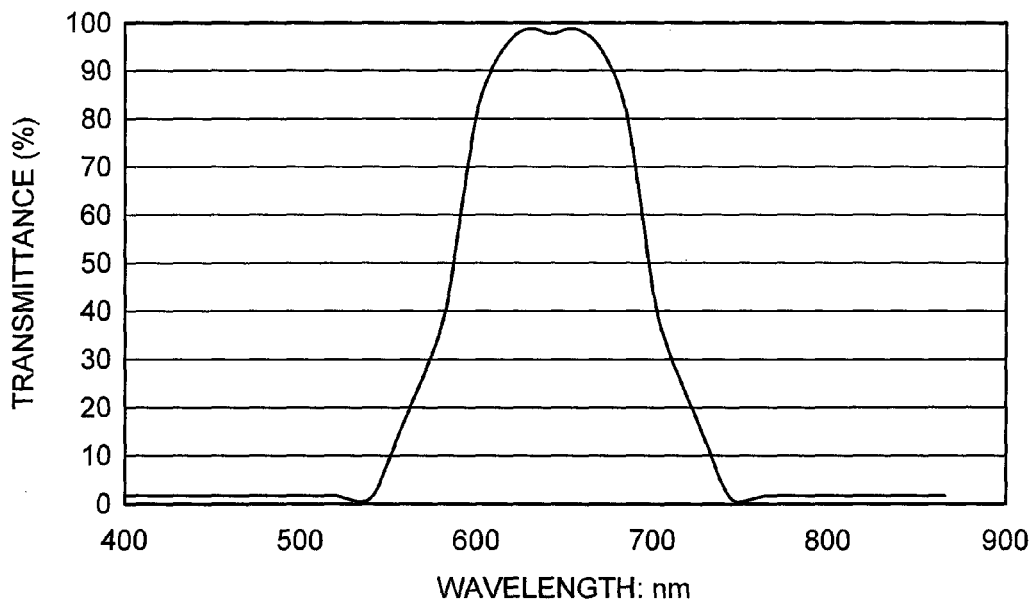
FIG. 28 is a graph illustrating the filter characteristics of a bandpass filter that is applicable in the spectral filter layer.

As the filter layer portion of the spectral filter layer 223 which has the red spectral area or the cyan spectral area formed thereon, it is possible to use a bandpass filter having the transparent wavelength range of 600 to 700 nm and having the filter characteristics as illustrated in FIG. 28. In the case of using a bandpass filter, it also becomes possible to identify the near-infrared color area and the red color area on the long-wavelength side of red color. Such a bandpass filter can be obtained by manufacturing a multi-layer film that has a configuration such as "substrate/(0.125L0.5M0.125L)p (0.125L0.5H0.125L)q(0.125L0.5 M0.125L)r/medium A)". Meanwhile, as described above, if titanium dioxide ($TiO_2$) is used as a high refractive index material and if silicon dioxide ($SiO_2$) is used as a low refractive index material, then it becomes possible to achieve the spectral filter layer 223 having high weather resistance.

Explained below is an example of the method of manufacturing the spectral filter layer 223 according to the present embodiment. Firstly, a multi-layer film as described above is formed on the layer of the filling material 224 applied on the filter substrate 221 and the polarization filter layer 222. As the method of forming the multi-layer film, it is possible to implement the widely-known method of vapor deposition. Subsequently, at the locations corresponding to the non-dispersive area, the multi-layer film is removed. As the removal method, it is possible to implement the commonly-known liftoff technique.

In the liftoff technique, a pattern opposite to the intended pattern is formed in advance with a metal or a photoresist on the layer of the filling material 224; a multi-layer film is formed on the opposite pattern; and the multi-layer film at the locations corresponding to the non-dispersive area is removed along with the metal or the photoresist.

In the present embodiment, since a multi-layer structure is used for the spectral filter layer 223, there is an advantage of having a high degree of freedom in setting the spectral transmittance. Generally, a color filter in a color sensor is formed with a resist agent. However, as compared to a multi-layer film structure, controlling the spectral transmittance is difficult in the case of using a resist agent. In that regard, in the present embodiment, since a multi-layer structure is used for the spectral filter layer 223, it becomes possible to form the spectral filter layer 223 that is optimized to the wavelength of a tail lamp.

Light Distribution Control for Headlamps

Given below is the explanation of light distribution control performed for headlamps.

According the present embodiment, in the light distribution control performed for headlamps, the captured image data of images captured by the imaging device 200 is analyzed, and tail lamps and headlamps of motor vehicles are identified. Subsequently, proceeding motor vehicles are detected from the identified tail lamps and oncoming motor vehicles are detected from the identified headlamps. Then, switchover between the high beam and the low beam of the headlamp 104 is performed along with partial light interception control of the headlamp 104, so as to secure visibility for the driver of the own motor vehicle 100 while preventing the intense light of the headlamp of the own motor vehicle 100 from getting in the eyes of the drivers of proceeding motor vehicles or the drivers of oncoming motor vehicles so that those drivers of other motor vehicles are not distracted.

Meanwhile, the following explanation is given for a case in which the first configuration example described above is used as the post-filter 220 of the optical filter 205.

In the light distribution control according to the present embodiment, of the information that can be obtained from the imaging unit 101, the following information is used: intensity of light emitted by each spot (light source body) within the imaging area (brightness information); distance between a light source body such as a headlamp or a tail lamp (of another motor vehicle) and the own motor vehicle (distance information); spectral information containing the comparison of the red color component and the white color component (non-dispersive type) of the light emitted by each light source body; polarization information containing the comparison of the horizontal polarization component and the vertical polarization component of the white color component; vertical polarization component information of white color component from which the horizontal polarization component is removed; and vertical polarization component information of red color component from which the horizontal polarization component is removed.

The following explanation is given regarding the brightness information. Consider that, during nighttime, a proceeding motor vehicle and an oncoming motor vehicle are present at the same distance from the own motor vehicle; and that the imaging device captures images of that proceeding motor vehicle and that oncoming motor vehicle. In that case, in the captured image data, the headlamp of the oncoming motor vehicle, which is one of the target objects for detection, appears most brightly; while the tail lamp of the proceeding motor vehicle, which is one of the target objects for detection, appears darker than the headlamp. Meanwhile, there are times when a headlamp reflector also appears in the captured image data. However, a headlamp reflector is not a light source that emits light, but is an object that appears bright because of the reflection of the headlamp light of the own motor vehicle. Hence, the headlamp reflector appears darker than even the tail lamp of the proceeding motor vehicle. As the distance from the own motor vehicle increases; the light emitted by the headlamp of the oncoming motor vehicle, the light emitted by the tail lamp of the proceeding motor vehicle, and the light reflected from the headlamp reflector are gradually observed to be darker by the image sensor 206 that is receiving those lights. Therefore, by referring to the brightness (luminance information) obtained from the captured image data, it becomes possible to perform primary identification of the two types of target objects for detection (i.e., the headlamp and the tail lamp) and the headlamp reflector.

The following explanation is given regarding the distance information. Most of the times, a headlamp or a tail lamp includes a symmetrical pair of lamps. Thus, by making use of this aspect of configuration, it is possible to obtain the distance from a headlamp or a tail lamp (i.e., the distance from another motor vehicle) to the own motor vehicle. In the captured image data, the lamps in the symmetrical pair of lamps appear close to each other at the same position heightwise. Moreover, lamp image areas, in each of which appears one of the two lamps, are almost equal in largeness as well as shape. Therefore, if such aspects are considered as conditions, then the lamp image areas satisfying those conditions can be identified to be corresponding to a symmetric pair of lamps. Meanwhile, as the distance goes on increasing, the lamp on the left side and the lamp on the right side in a symmetric pair of lamps cannot be recognized distinctly. Instead, the two lamps are recognized as a single lamp.

When the symmetric pair of lamps is identified using such a method, it becomes possible to calculate the distance up to the light source of the headlamp or the tail lamp configured with that pair of lamps. Regarding the distance between the pair of left and right headlamps and the distance between the pair of left and right tail lamps of a motor vehicle, it is possible to perform approximation with a constant value "w0" (for example, about 1.5 m). Besides, a focal length "f" of the imaging lens 204 in the imaging device 200 is known. Moreover, a distance "w1" between two lamp image areas corresponding to the right and left lamps on the image sensor 206 of the imaging device 200 can be calculated from the captured image data. With that, a distance "x" between the own motor vehicle and the headlamp or the tail lamp configured with the abovementioned pair of lamps can be obtained by a simple proportion ($x = f \times w0/w1$). If the distance "x" calculated in this manner is within an appropriate range, then it can be identified that the two lamp image areas used in the calculation represent the headlamp or the tail lamp of another motor vehicle. Therefore, the use of distance information leads to an enhancement in the identification accuracy of the headlamps and tail lamps that are the target objects for detection.

The following explanation is given regarding the spectral information. In the present embodiment, as described above, from the captured image data of images captured by the imaging device 200, if pixel data is extracted only corresponding to the imaging pixels "a", "c", "f", and "h" in the image sensor 206 that receive the red light (vertical polarization component) P/R; then it becomes possible to generate a red image that displays only the red color component within the imaging area. Thus, when an image area having luminance equal to or more than a predetermined luminance is present in a red image, that image area can be identified to be a tail lamp image area in which a tail lamp appears.

Moreover, from the captured image data of images captured by the imaging device 200, if pixel data is extracted only corresponding to the imaging pixels "b" and "d" in the image sensor 206 that receive the white light (non-dispersive light) P/C; then it becomes possible to generate a monochrome luminance image (vertical polarization component) within the imaging area. Consequently, it also becomes possible to calculate a luminance ratio (red luminance ratio) between the image area in the red image and the corresponding image area in the monochrome luminance image. By referring to the red luminance ratio, it becomes possible to know the relative proportion of red color component included in the light from the object (light source body) present in the imaging area. The red luminance ratio of a tail lamp has a sufficiently higher value than the red luminance ratio of a headlamp or most other light sources. Thus, using such red luminance ratio leads to an enhancement in the identification accuracy of tail lamps.

The following explanation is given regarding the polarization information. In the present embodiment, as described above, from the captured image data of images captured by the imaging device 200, pixel data can be extracted corresponding to the imaging pixels "b" and "d" in the image sensor 206 that receive the vertical polarization component P/C of white light (non-dispersive light) and pixel data can be extracted corresponding to the imaging pixels "e" and "g" in the image sensor 206 that receive the horizontal polarization component S/C of white light (non-dispersive light); and a comparison image can be obtained by comparing the pixel values (luminance) on a pixel-by-pixel basis between the two sets of pixel data. More particularly, for example, as a comparison image, it is possible to obtain a difference image in which pixel values indicate the difference values (S−P) between the vertical polarization component P of white light (non-dispersive light) and the horizontal polarization component S of white light (non-dispersive light). With such a comparison image, it becomes possible to increase the contrast between an image area of direct light (headlamp image area), in which the light emitted by a headlamp directly falls on the imaging device 200, and an image area of indirect light, in which the light emitted by a headlamp falls on the imaging device 200 after getting reflected from the water surface covering the road that is wet from the rain. That leads to an enhancement in the identification accuracy of headlamps.

Particularly, as a comparison image, it is possible to suitably use a ratio image in which pixel values indicate the ratios (S/P) between the vertical polarization component P of white light (non-dispersive light) and the horizontal polarization component S of white light (non-dispersive light), or a difference polarization degree image in which pixel values indicate the difference polarization degrees ((S−P)/(S+P)). Generally, it is known that the light reflected from a horizontal mirror surface such as a water surface always has a strong horizontal polarization component. Particularly, when the ratios (S/P) or the difference polarization degrees ((S−P)/(S+P)) between the vertical polarization component P of white light (non-dispersive light) and the horizontal polarization component S are taken, it is known that the ratio or the difference polarization degree is at the maximum at a specific angle (Brewster's angle). On a road that is wet from the rain, the asphalt surface that is a scattering surface gets filled with water thereby leading to a condition close to a mirror surface. Hence, in the light that is emitted by a headlamp and reflected from the road surface, the horizontal polarization component S is strong. Therefore, in a comparison image or a difference polarization degree image, the image area of the light emitted by a headlamp and reflected from the road surface has large pixel values (luminance). On the other hand, since the direct light from a headlamp is basically non-polarized, the pixel values (luminance) thereof are small in a comparison image or a difference polarization degree image. By making use of such a difference, it becomes possible to properly remove the light that is emitted by a headlamp and reflected from the wet road surface and that has about the same light intensity as the direct light from the headlamp. Thus, the direct light from the headlamp can be distinctly identified from the light emitted by a headlamp and reflected from the road surface.

Figure 29:
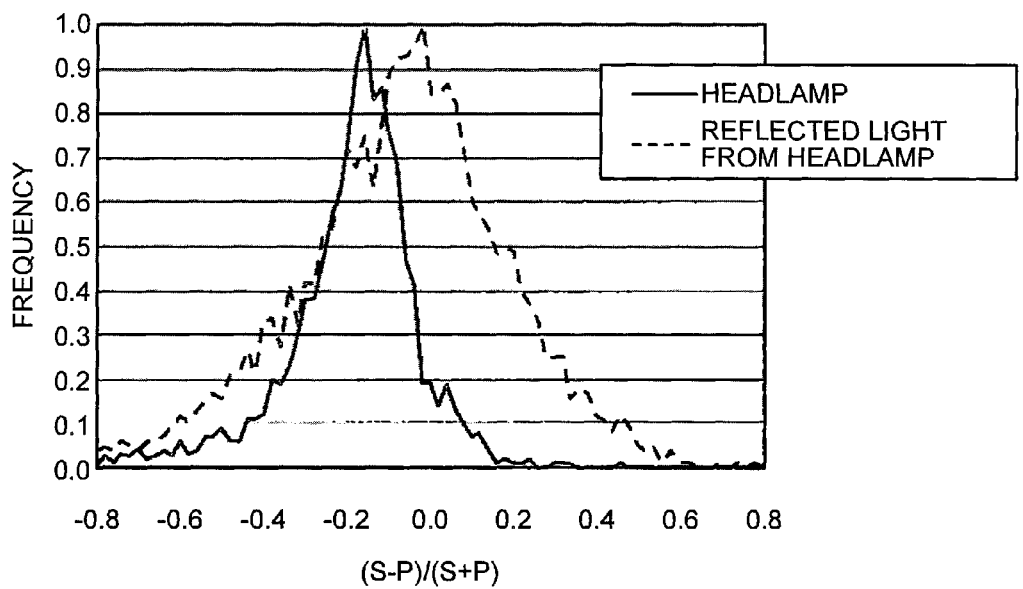
FIG. 29 is a histogram illustrating a case when images of the direct light from a headlamp on a rainy day as well as images of the reflected light (glare) of a headlamp from the wet road surface are captured using the imaging device, and respective difference polarization degrees are calculated.

FIG. 29 is a histogram illustrating a case when images of the direct light from a headlamp on a rainy day as well as images of the reflected light (glare) of a headlamp from the wet road surface are captured using the imaging device 200, and respective difference polarization degrees ((S−P)/(S+P)) are calculated. In FIG. 29, the vertical axis represents frequency, which is normalized to 1. In FIG. 29, the horizontal axis represents the calculation of difference polarization degrees ((S−P)/(S+P)). As is clear from FIG. 29, in comparison to the direct sunlight from a headlamp, the distribution of the reflected light of a headlamp from the wet road surface has shifted to the side on which the horizontal polarization component S is relatively large (shifted to the right side in FIG. 29).

Figure 30:
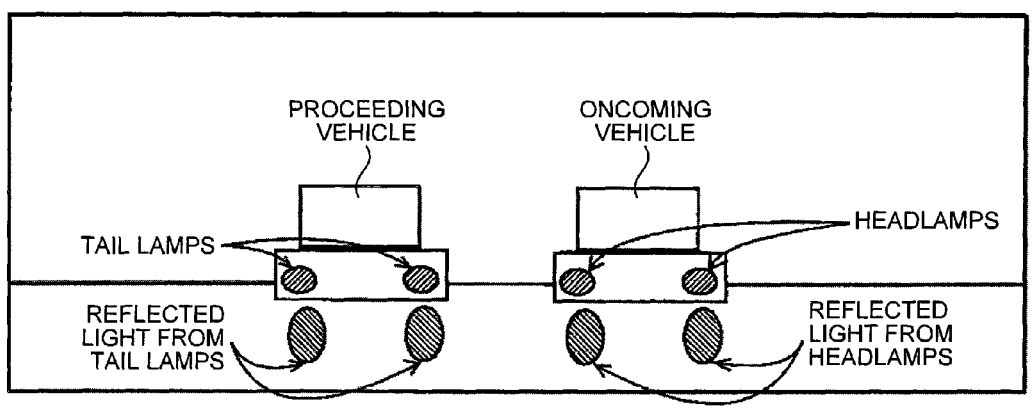
FIG. 30 is a schematic diagram illustrating an example when the imaging device captures images of a situation in which a proceeding motor vehicle and an oncoming motor vehicle are present at almost the same distance in the travelling direction of the own motor vehicle that is running on a wet road surface.

FIG. 30 is a schematic diagram illustrating an example when the imaging device 200 captures images of a situation in which a proceeding motor vehicle and an oncoming motor vehicle are present at almost the same distance in the travelling direction of the own motor vehicle that is running on a wet road surface.

In such a situation, if only the brightness information and the distance information is to be used, then it is difficult to distinctly detect the tail lamps of the proceeding motor vehicle, detect the glare of the tail lamps that is reflected from the wet road surface, detect the headlamps of the oncoming motor vehicle, and detect the glare of the headlamps that is reflected from the wet road surface.

According to the present embodiment, even in such a situation, firstly, the tail lamps of the proceeding motor vehicle and the glare of the tail lamps that is reflected from the wet road surface can be distinctly identified with high accuracy using the spectral information described above. Similarly, the headlamps of the oncoming motor vehicle and the glare of the headlamps that is reflected from the wet road surface can be distinctly identified with high accuracy using the spectral information described above. More particularly, in the lamp image areas narrowed down based on only the brightness information and the distance information, the image areas having the pixel values (luminance values) in excess of a predetermined threshold value or the red luminance ratio of the red image in excess of a predetermined threshold value are identified to be the tail lamp image areas in which appears the tail lamps of the proceeding motor vehicle or the glare of tail lamps that is reflected from the wet road surface. In contrast, the image areas having the pixel values (luminance values)

below the predetermined threshold value or the red luminance ratio of the red image below the predetermined threshold value are identified to be the headlamp image areas in which appears the headlamps of the oncoming motor, vehicle or the glare of the headlamps that is reflected from the wet road surface.

Moreover, according to the present embodiment, regarding each lamp image area identified using the spectral information in the manner described above, the direct light and the glare of a tail lamp or a headlamp can be identified with high accuracy using the polarization information described above. More particularly, for example, regarding tail lamps; on the basis of the pixel values (luminance values) of the red image or the difference polarization degrees of the horizontal polarization component S, the difference in frequencies or intensities of the horizontal polarization component is used in identifying the direct light from the tail lamps of the proceeding motor vehicle and identifying the glare of the tail lamps that is reflected from the wet road surface. Furthermore, for example, regarding headlamps; on the basis of the pixel values (luminance values) of the white image or the difference polarization degrees of the horizontal polarization component, the difference in frequencies or intensities of the horizontal polarization component is used in identifying the direct light from the headlamps of the oncoming motor vehicle and identifying the glare of the headlamps that is reflected from the wet road surface.

Figure 31:
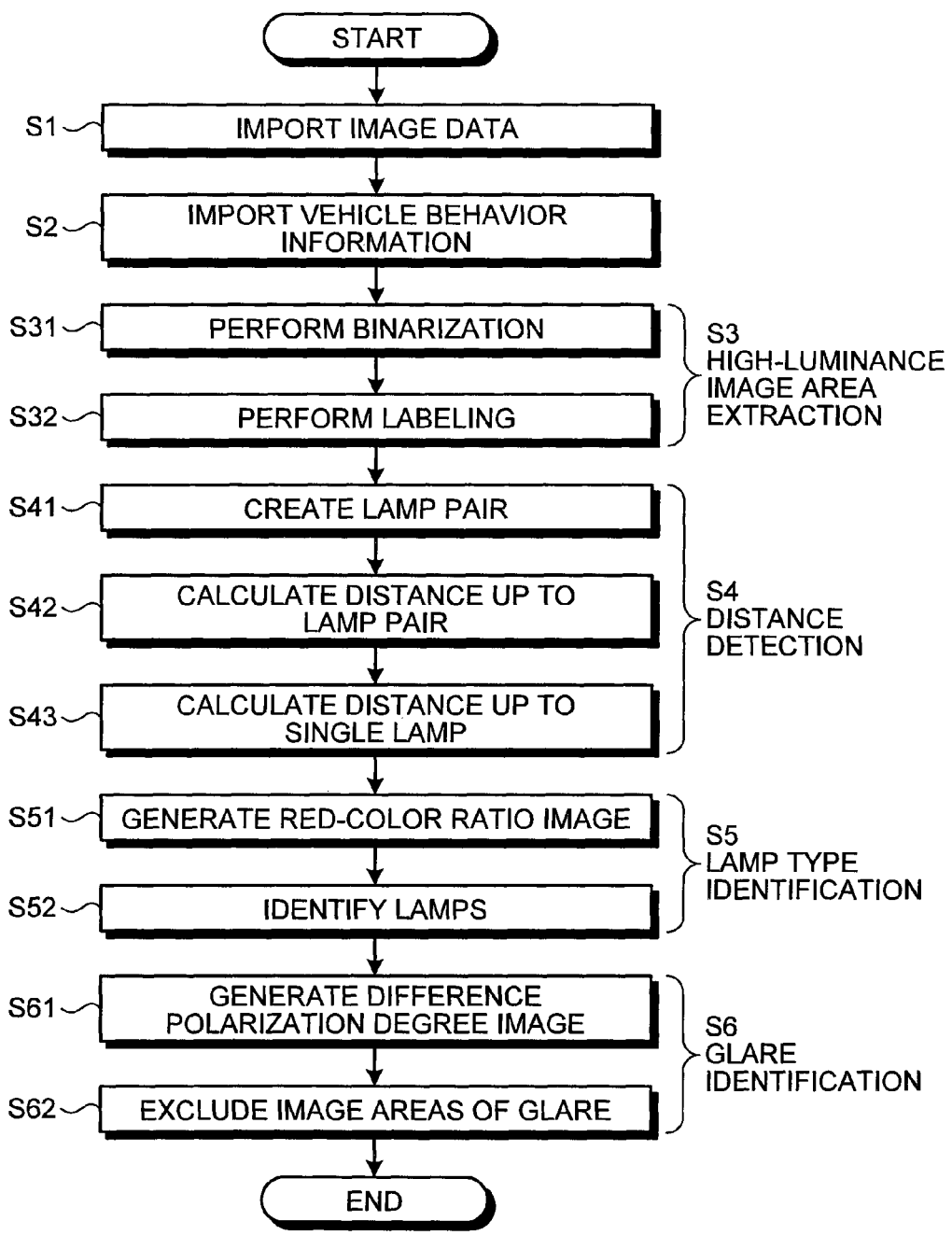
FIG. 31 is a flowchart for explaining a sequence of operations performed during a motor vehicle detection operation according to the embodiment.

Explained below is a sequence of operations performed during a detection operation for detecting a proceeding motor vehicle and an oncoming motor vehicle according to the present embodiment. FIG. 31 is a flowchart for explaining a sequence of operations performed during the motor vehicle detection operation according to the present embodiment.

During the motor vehicle detection operation according to the present embodiment, image processing is performed on the image data of images captured by the imaging device 200, and image areas that are believed to be target objects for detection are extracted. Then, detection of a proceeding motor vehicle or an oncoming motor vehicle is performed by identifying the type of the target object for detection from among the two types of light source bodies appearing in those image areas.

Firstly, at Step S1, the image data of images of the front area of the own motor vehicle captured by the image sensor 206 of the imaging device 200 is imported in a memory. As described above, the image data contains signals indicating the luminance at each imaging pixel of the image sensor 206. Then, at Step S2, information related to the behavior of the own motor vehicle is imported from a vehicle behavior sensor (not illustrated).

At Step S3, from the image data imported in the memory, image areas having high luminance (high-luminance image areas) that are believed to be the target objects for detection (tail lamps of a proceeding motor vehicle and headlamps of an oncoming motor vehicle) are extracted. In the image data, the high-luminance image areas are bright areas having a higher luminance than a predetermined threshold luminance. It is often the case that there is a plurality of high-luminance image areas, all of which are extracted. Therefore, at this stage, image areas containing the glare from the wet road surface are also extracted as high-luminance image areas.

During the high-luminance image area extracting operation, firstly, at Step S31, binarization is performed by comparing the luminance value of each imaging pixel of the image sensor 206 with a predetermined threshold luminance. More particularly, a binarized image is generated by assigning "1" to the pixels having the luminance equal to or greater than the predetermined luminance and by assigning "0" to the pixels having a smaller luminance than the predetermined luminance. Then, at Step S32, in the binarized image, when the pixels having "1" assigned thereto are positioned close to each other, a labeling operation is performed in which those pixels are recognized as a single high-luminance image area. With that, each set of a plurality of high-luminance pixels positioned close to each other is extracted as a single high-luminance image area.

After performing the high-luminance image area extracting operation; at Step S4, the distance is calculated between the own motor vehicle and an object within the imaging area corresponding to each high-luminance image area. During the distance calculating operation, the following two operations are performed: a lamp-pair distance calculating operation in which the distance is calculated by making use of the fact that the lamps of a motor vehicle are symmetrical pairs of lamps; and a single-lamp distance calculating operation performed when the left and right lamps in a pair of lamps at far distance cannot be recognized distinctly, but are recognized as a single lamp.

In order to perform the lamp-pair distance calculating operation, firstly at Step S41, a lamp pair creating operation is performed to create a pair of lamps. In the image data of images captured by the imaging device 200, the lamps in a symmetrical pair of lamps satisfy the conditions that the positions thereof are close to each other at almost the same height, and that the high-luminance image areas thereof are of almost the same dimensions and shapes. Thus, the high-luminance image areas satisfying such conditions are considered to be a pair of lamps, while the high-luminance image areas not pairing up are considered to be single lamps. When a pair of lamps is created, the lamp-pair distance calculating operation is performed at Step S42 to calculate the distance up to the pair of lamps. Regarding the distance between the pair of left and right headlamps and the distance between the pair of left and right tail lamps of a motor vehicle, it is possible to perform approximation with the constant value "w0" (for example, about 1.5 m). Besides, the focal length "f" of the imaging device 200 is known. Moreover, the distance "w1" between the right and left lamps on the image sensor 206 of the imaging device 200 can be calculated. With that, the actual distance "x" up to the pair of lamps can be obtained by a simple proportion (x=f×w0/w1). Meanwhile, the distance detection up to a proceeding motor vehicle or an oncoming motor vehicle can also be performed using a dedicated distance sensor such as a laser radar or a millimeter-wave radar.

At Step S5, a lamp type identification operation is performed in which the ratio (red luminance ratio) between the vertical polarization component P of the red image and the vertical polarization component P of the white image is used as spectral information to identify whether the two high-luminance image areas considered to be a pair of lamps are formed due to the light emitted by headlamps or due to the light emitted by tail lamps. During the lamp type identification operation, firstly, at Step S51, a red-color ratio image is generated in which pixel values point to the ratios between pixel data corresponding to the imaging pixels "a" and "f" on the image sensor 206 and pixel data corresponding to the imaging pixel "b" on the image sensor 206. Then, at Step S52, a lamp identification operation is performed in which the pixel values of the red-color ratio image are compared with a predetermined threshold value; and the high-luminance image areas having pixel values equal to or greater than the predetermined threshold value are considered to be tail lamp image areas formed due to the light emitted by tail lamps, while the high-luminance image areas having pixel values smaller than the predetermined threshold value are considered to be headlamp image areas formed due to the light emitted by headlamps.

Then, at Step S6, regarding each image area identified either as a tail lamp image area or as a headlamp image area, a glare identification operation is performed in which it is identified whether the light is the direct light from tail lamps or the glare reflected from the mirror surface such as the wet road surface. During the glare identification operation, firstly, at Step S61, the difference polarization degrees ((S−P)/(S+P)) are calculated regarding the tail lamp image areas and a difference polarization degree image is generated in which pixel values point to those difference polarization degrees. In an identical manner, the difference polarization degrees ((S−P)/(S+P)) are calculated also regarding the headlamp images areas and a difference polarization degree image is generated in which pixel values point to those difference polarization degrees. Then, at Step S62, the pixel values of each difference polarization degree image are compared with a predetermined threshold value. The tail lamp image areas and the headlamp image areas having pixel values equal to or greater than the predetermined threshold value are determined to be formed due to the glare; and an exclusion operation is performed to exclude such image areas in accordance with the fact that the tail lamps of a proceeding motor vehicle or the headlamps of an oncoming motor vehicle do not appear in those image areas. After completing the exclusion operation, the remaining tail lamp image areas and the remaining headlamp image areas are identified to be displaying the tail lamps of a proceeding motor vehicle and the headlamps of an oncoming motor vehicle, respectively.

Meanwhile, the glare identification operation at Step S6 can be performed only when a rain sensor is installed in the motor vehicle and when the rain sensor confirms that it is rainy weather. Alternatively, the glare identification operation at Step S6 can be performed only when the driver operates the wipers. In essence, the glare identification operation at Step S6 can be performed only when it is rainy weather in which there is a possibility of a glare from the wet road surface.

The detection result of proceeding motor vehicles and oncoming motor vehicles that is obtained by performing the motor vehicle detection operation in the manner described above is used in the light distribution control of headlamps that are in-vehicle devices of the own motor vehicle in the present embodiment. More particularly, when the tail lamps of a proceeding motor vehicle are detected during the motor vehicle detection operation and when that proceeding motor vehicle comes close to the distance range in which the headlamp light of the own motor vehicle falls on the rearview mirror of the proceeding motor vehicle; then control is performed either to partially intercept the headlamp light of the headlamps of the own motor vehicle or to divert the emitting direction of the headlamp light of the own motor vehicle in vertical direction or in the horizontal direction so that the headlamp light of the own motor vehicle does not fall on the proceeding motor vehicle. Similarly, when the headlamps of an oncoming motor vehicle are detected during the motor vehicle detection operation and when that oncoming motor vehicle comes close to the distance range in which the headlamp light of the own motor vehicle falls on the driver of the oncoming motor vehicle; then control is performed either to partially intercept the headlamp light of the headlamps of the own motor vehicle or to divert the emitting direction of the headlamp light of the own motor vehicle in vertical direction or in the horizontal direction.

Distinguishing Operation for Distinguishing Between Dry Condition and Wet Condition of Road Surface Explained below is a distinguishing operation according to the present embodiment for distinguishing between the dry condition and the wet condition of the road surface.

In the present embodiment, in order to determine whether or not the road surface is wet and has become slippery for the own motor vehicle, a distinguishing operation is performed to distinguish between the dry condition and the wet condition of the road surface.

In the distinguishing operation according to the present embodiment for distinguishing between the dry condition and the wet condition of the road surface; of the information that can be obtained from the imaging unit 101, polarization information is used that is obtained by comparing the horizontal polarization component and the vertical polarization component of the white color component (non-dispersive light).

Figure 32:
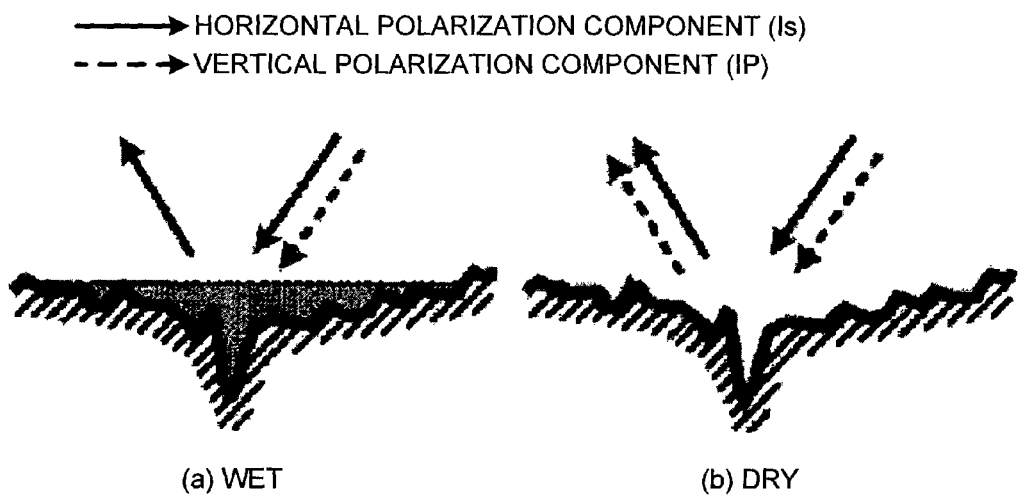
FIG. 32 shows the changes in the reflected light when the road surface is wet and when the road surface is dry.

FIG. 32 shows the changes in the reflected light when the road surface is wet (see the state (a)) and when the road surface is dry (see the state (b)).

As illustrated in the state (a) in FIG. 32, on a wet road surface, water gets filled in the uneven portions of the road surface thereby leading to a condition close to a mirror surface. For that reason, the reflected light from the wet road surface exhibits following polarization property. If it is assumed that Rs represents the reflectance of the horizontal polarization component of the reflected light and Rp represents the reflectance of the vertical polarization component of the reflected light; then a vertical polarization component Is of the reflected light with respect to the incident light having a light intensity I can be calculated using Equation (1) given below, and a horizontal polarization component Ip of the reflected light with respect to the incident light having the light intensity I can be calculated using Equation (2) given below. Moreover, the incident angle dependence of the components is as illustrated in FIG. 33.

$$Is = Rs \times I \quad (1)$$

$$Ip = Rp \times I \quad (2)$$

Figure 33:
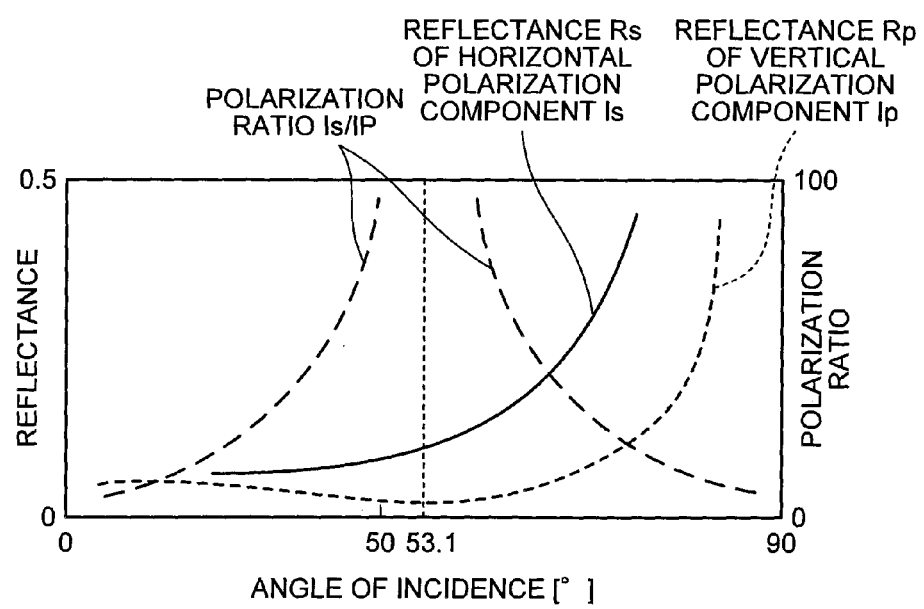
FIG. 33 is a graph illustrating the incident angle dependence of a horizontal polarization component Is and a vertical polarization component Ip of the reflected light with respect to the incident light having a light intensity I.

As can be noted in FIG. 33, when the angle of incidence is equal to the Brewster's angle)(53.1°), the reflectance Rp of the vertical polarization component Ip of the reflected light from the mirror surface becomes zero and the reflected light intensity of the vertical polarization component Ip becomes zero. The reflectance Rs of the horizontal polarization component Is of the reflected light from the mirror surface exhibits the characteristic of a gradual increase accompanying an increase in the angle of incidence. Hence, the reflected light intensity of the horizontal polarization component Is also increases gradually accompanying an increase in the angle of incidence. On the other hand, as illustrated in the state (b) in FIG. 32, since a dry road surface is rough in nature, the diffused reflection becomes dominant and the reflected light does not exhibit the polarization property. That leads to a decrease in the difference between the reflectance Rs and the reflectance Rp of the polarization components.

Because of such differences in the polarization property of the reflected light from the road surface, it becomes possible to determine whether the road surface is wet or dry. More particularly, in the present embodiment, in order to determine whether the road surface is wet or dry, a polarization ratio H given below in Equation (3) is used. The polarization ratio H can be obtained as the average value of the ratio (S/P) calculated between the vertical polarization component P of white light (non-dispersive light) and the horizontal polarization component S of white light (non-dispersive light). As given below in Equation (3), the polarization ratio H is a parameter that is not dependent on the incident light intensity I. Hence, the determination of whether the road surface is wet or dry can be performed in a stable manner without getting affected by luminance fluctuation within the imaging area.

$$H=Is/IP=Rs/Rp \qquad (3)$$

If the polarization ratio H obtained in the abovementioned manner is exceeding a predetermined threshold value, then it is determined that the road surface is wet; and if the polarization ratio H is equal to or smaller than the predetermined threshold value, then it is determined that the road surface is dry. When the road surface is dry, the horizontal polarization component S is almost equal to the vertical polarization component P. Hence, the polarization ratio becomes equal to around 1. On the other hand, when the road surface is completely wet, the horizontal polarization component S increases to a substantially large value as compared to the vertical polarization component P, and thus the polarization ratio H increases to a large value. Meanwhile, if the road surface is slightly wet, the polarization ratio H becomes an intermediate value between the two values mentioned above.

In the present embodiment, the result of the distinguishing operation, which is performed to distinguish between the dry condition and the wet condition of the road surface, is used in performing driving support control such as issuing warnings to the driver of the own motor vehicle 100 or controlling the steering wheel or the brakes of the own motor vehicle 100. More particularly, when it is determined that the road surface is wet, the result is sent to the vehicle running control unit 108 and, for example, is used in controlling the automatic braking system of the own motor vehicle 100. Such measures are expected to be effective in reducing the number of traffic accidents. Moreover, for example, warning information such as the road surface is slippery can be displayed on a CRT screen of the vehicle navigation system in the own motor vehicle so as to draw the driver's attention to the situation.

Detection Operation for Detecting on-Road Metal Bodies

Explained below is a detection operation according to the present embodiment for detecting on-road metal bodies.

In the present embodiment, with the aim of preventing sideslip of the own motor vehicle 100 or preventing false recognition by a radar (described later), a detection operation is performed to detect on-road metal bodies as the target objects for detection. Herein, on-road metal bodies point to metallic objects lying almost in the same plane as the road surface. For example, on-road metal bodies point to manhole covers on ordinary roads or metallic joints on freeways. A manhole cover is a metal plate fit in the opening of a manhole, and is generally made of cast iron that is strong and heavy.

During the detection operation according to the present embodiment for detecting on-road metal bodies, firstly, a target area for identification is limited by excluding the image area not showing the road surface having on-road metal bodies to be detected, that is, by excluding the upper area of the captured images. Although limiting the target area for identification is not necessary, it is effective in reducing the processing time. Subsequently, a plurality of processing lines is set with respect to the target area for identification. In the present embodiment, as illustrated in FIG. 34, the processing lines are set corresponding to the rows of pixels arranged laterally within the target area for identification. However, the processing lines need not be oriented in the lateral direction. Alternatively, the processing lines can be oriented in the longitudinal direction or in an oblique direction. Moreover, the pixel count in each processing line can either be same or be different. Furthermore, the processing lines need not be set with respect to all pixels within the target area for identification. Alternatively, the processing lines can be set with respect to some pixels selected in an appropriate manner within the target area for identification.

According to the present embodiment, during the detection operation for detecting on-road metal bodies; of the information that can be obtained from the imaging unit 101, polarization information is used that is obtained by comparing the horizontal polarization component S and the vertical polarization component P of the white color component (non-dispersive light). Meanwhile, the vertical polarization component of the white color component can also contain the vertical polarization component of red light. In the present embodiment, the difference polarization degrees ((S−P)/(S+P)) of the horizontal polarization component S and the vertical polarization component P of the white color component (non-dispersive light) are used as this polarization information. More particularly, from the image data of the horizontal polarization component S of the white color component (non-dispersive light) and from the image data of the vertical polarization component P of the white color component (non-dispersive light) of images captured by the imaging unit 101, a difference polarization degree image is generated in which pixel values point to difference polarization degrees ((S−P)/(S+P)). Then, along a processing line mentioned above, a difference value between each pair of adjacent pixel values (difference polarization degrees) is calculated. If a difference value is equal to greater than an on-road metal body threshold value, then that area between the corresponding two adjacent pixels is identified as an edge. Subsequently, the pixel values (difference polarization degrees) of the pixels related to the identified edge are compared with a threshold value for on-field metal body identification. If the pixel values are equal to or greater than the threshold value for on-field metal body identification, then the corresponding edge is extracted as an edge of an on-road metal body.

By performing such edge extracting operation for all processing lines, it becomes possible to extract image areas that are enclosed by the edges of on-road metal bodies as on-road metal-body image area candidates. Then, the on-road metal-body image area candidates that are extracted are subjected to a shape approximation recognition operation. More particularly, the shapes of on-road metal-body image area candidates are compared with on-road metal body shape templates that are stored in advance. If the shape of an on-road metal-body image area candidate matches with an on-road metal body shape template, then that on-road metal-body image area candidate is identified to be an on-road metal body image area.

During the shape approximation recognition operation; shape approximation recognition is performed with respect to the edges of an on-road metal-body image area candidate, and approximated curves are obtained. As the method of recognizing a shape, it is possible to use the least-square technique, the Hough transform, or the model equation. At the time of obtaining approximated curves, it is desirable that the edges that are related to the image area candidates located in the lower part of reliable captured images are given more weight-age as far as voting values for shape approximation are concerned. With that, even if edges are present that are related to a falsely-recognized image area candidate in the upper portion of captured images having low reliability; as long as edges are present that are related to correctly-recognized image area candidates in the lower portion of reliable captured images, it becomes possible to appropriately identify the on-road metal bodies.

Meanwhile, with the aim of enhancing the detection accuracy of on-road metal bodies, the following operation can be additionally performed.

In the case of detecting on-road metal bodies in real time, regarding the image areas that are identified to be on-road metal bodies on the basis of difference polarization degree images captured continuously at regular intervals by the imaging device 200, the processing results are stored in a predetermined memory. Then, the processing result stored the previous time or stored before the previous time is referred to determine whether the on-road metal body image area identified in the current processing result has already been identified to be containing an on-road metal body in an earlier processing result. If that is the case, then it is determined that the current processing result has a high degree of reliability. That degree of reliability is then used while identifying on-road metal body image areas. As far as identifying the earlier processing results related to the image area in the current processing result is concerned; for example, by referring to the position of the image area in the current processing result as well as by referring to the travelling direction and the velocity of the own motor vehicle, the position of the same image area is searched in the earlier processing results, and the earlier processing results related to the image area in the current processing result are identified.

The explanation given above is for the case of extracting edges of on-road metal bodies along the processing lines. However, instead of the processing lines, the edge extracting operation can also be performed in the units of processing blocks (formed with a matrix of two or more pixels). In this case, for example, a plurality of processing blocks is set with respect to the target area for identification; and, for each block, a standard deviation is calculated that indicates the extent of variation (extent of diffusion) of the pixel values (difference polarization degrees). When a calculated standard deviation is equal to or greater than a standard deviation threshold value, then it can be determined that an edge is present inside that processing block. Meanwhile, the processing blacks can be set as oblong sections or as sections of other shapes. The size of a processing block can be set equal to, for example, about 10×10 image pixels. Moreover, each processing block can either be of the same size or be of a different size. Furthermore, instead of using the standard deviation, it is also possible to use a statistic such as dispersion or average deviation.

Meanwhile, the threshold values that are used at the time of detecting on-road metal bodies can be changed according to the changes in the environment. For example, the threshold values can be changed depending on the time period such as daytime or nighttime or depending on the weather such as rainy weather or fair weather. To perform such changes, it is possible to make use of time information or information of a rain sensor or a sunshine sensor.

Explained below is the reason for being able to distinctly recognize on-field metal bodies from the road surface with the use of difference polarization degrees.

When light falls with a certain angle (angle of incidence) on the interface between two materials having mutually difference refractive indices, then the polarization component parallel to the plane of incidence (in the present embodiment, the vertical polarization component P) has a different reflectance than the polarization component orthogonal to the plane of incident (in the present embodiment, the horizontal polarization component S). Specifically, as the angle of incidence goes on increasing, the reflectance of the vertical polarization component P decreases to zero at a certain angle (Brewster's angle) before increasing. In contrast, the reflectance of the horizontal polarization component S monotonically increases accompanying the increase in the angle of incidence. In this way, the vertical polarization component P and the horizontal polarization component S have different reflection characteristics. As a result, the difference polarization degrees ((S−P)/(S+P)) also vary depending on the angles of incidence and the refractive indices.

In the present embodiment, by making use of the fact that the difference polarization degrees ((S−P)/(S+P)) vary depending on the differences in the material of the reflecting surface, that is, depending on the differences in the refractive indices; the on-field metal bodies are distinctly recognizable from the road surface by referring to the difference polarization degrees. The road surface is generally made of asphalt, while the on-road metal bodies are made of metal. When there is such a difference in material, the refractive indices are also different thereby causing a difference in the difference polarization degrees between the road surface and the on-road metal bodies. Using such a difference, borders (edges) between the road surface and the on-road metal bodies can be extracted as described above, and image areas of the on-road metal bodies can be identified. Then, by performing the shape approximation recognition operation, the types of on-road metal bodies (such as manhole covers or metallic joints) can be identified using shape templates.

FIGS. 35A and 35B are exemplary images respectively illustrating a monochrome luminance image (non-dispersive type/non-polarized type) and a difference polarization degree image of non-dispersive type captured within the same imaging area.

Since the imaging area is dark, in the monochrome luminance image illustrated in FIG. 35A, it can be seen that there is not much contrast between the asphalt surface (road surface) and a manhole cover (on-road metal body). In contrast, in the difference polarization degree image illustrated in FIG. 35B, there is a sharp contrast between the asphalt surface (road surface) and the manhole cover (on-road metal body). Therefore, even though it is difficult to identify the manhole cover in the monochrome luminance image, a highly accurate identification of the manhole cover becomes possible when the difference polarization degree image is used.

In the present embodiment, the result of the detection operation for detecting on-road metal bodies is used in performing driving support control such as issuing warnings to the driver of the own motor vehicle 100 or controlling the steering wheel or the brakes of the own motor vehicle 100. More particularly, when an on-read metal body is determined to be present, the determination result is sent to the vehicle running control unit 108 and, for example, is used in controlling the automatic braking system of the own motor vehicle 100. Such measures are expected to be effective in reducing the number of traffic accidents. Moreover, for example, lane departure information can be displayed on a CRT screen of the vehicle navigation system in the own motor vehicle so as to draw the driver's attention to the situation.

Moreover, the result of the detection operation for detecting on-road metal bodies can be used in a sensor fusion system in which the measurement result of a radar and the captured images in the imaging device 200 are used in combination. More particularly, there is a possibility that an on-road metal body is falsely recognized as a collision avoiding object, such as a proceeding motor vehicle or a guardrail, in the measurement result of the radar. Thus, by correcting the measurement result of the radar using the detection result of on-road metal bodies from the images captured by the imaging device 200, it becomes possible to prevent false recognition of collision avoiding objects by the radar. As a result, for example, it becomes possible to prevent a situation from occurring in which, while the own motor vehicle is running, an on-road metal body is falsely recognized as a collision avoiding object and the automatic braking system operates to cause a sudden deceleration of the own motor vehicle.

Moreover, the result of the detection operation for detecting on-road metal bodies can be used as location information in the vehicle navigation so as to enhance the location identifying accuracy of the own motor vehicle. More particularly, a database is made of location information of the locations of manholes on the road. Then, the distance from the own motor vehicle to those manhole covers and the directions of those manhole cover are identified by referring to the detection result of manhole covers, and relative location information of the own motor vehicle with respect to the manhole covers is generated. Moreover, manhole IDs of those particular manhole covers are identified. Subsequently, the manhole location information corresponding to the identified manhole IDs is read from the database, and the location of the own motor vehicle identified by the vehicle navigation is corrected by referring to the manhole location information and the relative location information of the own motor vehicle with respect to the manhole covers.

Meanwhile, the detection operation for detecting on-road metal bodies can also be performed with respect to difference polarization degree images from which white lines are removed using the result of a white line recognizing operation (described later). In this case, the accuracy of identifying on-road metal bodies can be enhanced by appropriately removing the noise including the white lines.

Detection Operation for Detecting Three-Dimensional Objects

Explained below is a detection operation according to the present embodiment for detecting three-dimensional objects.

In the present embodiment, with the aim of avoiding collision with three-dimensional objects, a detection operation is performed to detect three-dimensional objects as target objects for detection.

Herein, three-dimensional objects point to all three-dimensional objects that have an external surface oriented in a different direction than the road surface. Thus, the three-dimensional objects include motor vehicles running on the road, guardrails installed on the sides of the road, utility poles, street lights, road signs, off-street obstacles such as unevenness on the sides of the road, people present on the road or on the shoulder of the road, animals, and bicycles.

During the detection operation according to the present embodiment for detecting three-dimensional objects; of the information that can be obtained from the imaging unit 101, polarization information is used that is obtained by comparing the horizontal polarization component S and the vertical polarization component P of the white color component (non-dispersive light). Meanwhile, the vertical polarization component of the white color component can also contain the vertical polarization component of red light. In the present embodiment, in an identical manner to the detection operation for detecting on-road metal bodies, the difference polarization degrees ((S−P)/(S+P)) of the horizontal polarization component S and the vertical polarization component P of the white color component (non-dispersive light) are used as this polarization information.

Firstly, from the image data of the horizontal polarization component S of the white color component (non-dispersive light) and from the image data of the vertical polarization component P of the white color component (non-dispersive light) of images captured by the imaging unit 101, a difference polarization degree image is generated in which pixel values point to difference polarization degrees ((S−P)/(S+P)). Then, in an identical manner to the detection operation for detecting on-road metal bodies, a plurality of processing lines is set. However, since three-dimensional objects serving as target objects for detection are present across the entire imaging area, the processing lines are set in the entire captured image as illustrated in FIG. 36 without limiting a target area for identification. Herein, the method of setting the processing lines (or processing blocks) is identical to the method explained in the detection operation for detecting on-road metal bodies.

Once the processing lines are set in the abovementioned manner, difference values between pairs of adjacent pixel values (difference polarization degrees) are calculated along the processing lines. If a difference value is equal to greater than a three-dimensional object threshold value, then that area between the corresponding two adjacent pixels is identified as an edge. Subsequently, the pixel values (difference polarization degrees) of the pixels related to the identified edge are compared with a threshold value for three-dimensional object identification. If the pixel values are equal to or greater than the threshold value for three-dimensional object identification, the corresponding edge is extracted as an edge of a three-dimensional object.

By performing such edge extracting operation for all processing lines, it becomes possible to extract image areas enclosed by the edges of three-dimensional objects as three-dimensional-object image area candidates. Then, the three-dimensional-object image area candidates that are extracted are subjected to the shape approximation recognition operation. More particularly, the shape of a three-dimensional-object image area candidate is compared with three-dimensional object shape templates that are stored in advance. If the shape of a three-dimensional-object image area candidate matches with a three-dimensional object shape template, then that three-dimensional-object image area candidate is identified to be a three-dimensional object image area. Herein, the shape approximation recognition operation is identical to the shape approximation recognition operation performed during the detection operation for detecting on-road metal bodies.

Meanwhile, the threshold values that are used at the time of detecting three-dimensional objects can be changed according to the changes in the environment. For example, the threshold values can be changed depending on the time period such as daytime or nighttime or depending on the weather such as rainy weather or fair weather. To perform such changes, it is possible to make use of time information or information of a rain sensor or a sunshine sensor.

Explained below is the reason for being able to recognize three-dimensional objects with the use of difference polarization degrees.

As described already, when light falls with a certain angle (angle of incidence) on the interface between two materials having mutually difference refractive indices, then the vertical polarization component P has a different reflectance than the horizontal polarization component S. As a result, the difference polarization degrees ((S−P)/(S+P)) also vary depending on the angles of incidence and the refractive indices. In the present embodiment, by making use of the fact that the difference polarization degrees ((S−P)/(S+P)) vary depending on the differences in the material of the reflecting surface, that is, depending on the differences in the refractive indices; the three-dimensional objects are distinctly recognizable from the road surface by referring to the difference polarization degrees. The road surface is generally made of asphalt, while three-dimensional objects such as other motor vehicles or guardrails present in the imaging area are made of coated metallic surfaces. When there is such a difference in material, the refractive indices are also different thereby causing a difference in the difference polarization degrees between the road surface and the three-dimensional objects. Using such a difference, borders (edges) between the road surface and the three-dimensional objects, such as other motor vehicles or guardrails made of coated metallic surfaces, can be extracted as described above, and image areas of the three-dimensional objects can be identified.

Moreover, although the road surface is a flat face in the substantially horizontal direction, the three-dimensional objects such as other motor vehicles have side faces oriented in directions other than the road surface. Thus, depending on the road surface and a three-dimensional object, the angle of incidence is different for the reflected light incorporated in the imaging device 200. Therefore, depending on the road surface and a side face of three-dimensional object, the vertical polarization component P and the horizontal polarization component S of the corresponding reflected light are different. Particularly, when a side face of a three-dimensional object is substantially upright with respect to the road surface, then the correlation between the vertical polarization component P and the horizontal polarization component S included in the reflected light from that side face of the three-dimensional object comes close to the interchanged correlation between the vertical polarization component P and the horizontal polarization component S included in the reflected light from the road surface. As far as the correlation between the vertical polarization component P and the horizontal polarization component S included in the reflected light is concerned; generally, the horizontal polarization component S that is the orthogonal polarization component is greater with respect to the plane of incidence. Thus, when the imaging device 200 receives the reflected light from the road surface or from a face parallel to the road surface, then the horizontal polarization component S is stronger than the vertical polarization component P. In contrast, when the imaging device 200 receives the reflected light from a side face of a three-dimensional object that is substantially upright with respect to the road surface, then the vertical polarization component P is stronger than the horizontal polarization component S. Because of such differences in the polarization property between the road surface and a three-dimensional object, a comparison between the vertical polarization component P and the horizontal polarization component S included in the reflected light received by the imaging device 200 makes it possible to understand that a stronger horizontal polarization component S indicates the reflected light from a face parallel to the road surface and a stronger vertical polarization component P indicates the reflected light from a face orthogonal to the road surface. As a result, for example, the difference values (or the difference polarization degrees) between the vertical polarization component P and the horizontal polarization component S included in the reflected light received by the imaging device 200 can be calculated; and, depending on whether the difference values (or the difference polarization degrees) are positive or negative, it can be known whether the object has a face parallel to the road surface or the object is a three-dimensional object having an external face oriented in a different direction than the road surface.

Using such differences in materials and angles of incidence, borders (edges) between the road surface and the three-dimensional objects can be extracted, and image areas of the three-dimensional objects can be identified. Then, by performing the shape approximation recognition operation, the types of three-dimensional objects (such as motor vehicles or guardrails) can be identified using shape templates.

FIGS. 37A and 37B are exemplary images respectively illustrating a monochrome luminance image (non-dispersive type/non-polarized type) and a difference polarization degree image of non-dispersive type captured within the same imaging area.

Since the imaging area is dark, in the monochrome luminance image illustrated in FIG. 37A, it can be seen that there is not much contrast between the asphalt surface (road surface) and a proceeding motor vehicle (three-dimensional object). In contrast, in the difference polarization degree image illustrated in FIG. 37B, there is a sharp contrast between the asphalt surface (road surface) and the proceeding motor vehicle (three-dimensional object). Therefore, even though it is difficult to identify the proceeding motor vehicle in the monochrome luminance image, a highly accurate identification of the proceeding motor vehicle becomes possible when the difference polarization degree image is used.

Herein, regarding the difference polarization degrees accompanying the differences in materials, the difference between the polarization reflectance property of the asphalt (road surface) that is the material used in making the road surface and the polarization reflectance property of the coating material used on the side face of a motor vehicle (three-dimensional object) are subjected to evaluative analysis and it is confirmed that the respective polarization reflectance models are different and it is confirmed that consequently it is possible to distinguish between the asphalt road surface and the motor vehicle. The concrete explanation is given below.

The reflected light from an object contains a specular reflection component that is referred to as "shine"; contains a diffuse reflection component that is the matte reflection component representing the minute uneven structure of the object surface; and contains an internal scatter component that scatters inside the object before coming out. The intensity of the reflected light is expressed as the sum of these three components. Meanwhile, the specular reflection component can be considered to be a part of the diffuse reflection component. The diffuse reflection component and the internal scatter component are measured irrespective of the direction in which the light source that emits light to the object is present (that is, there is a low dependence on the angle of incidence). In contrast, the specular reflection component is highly dependent on the angle of incidence and is measured only when the light source is present in almost the specular direction with respect to the light receiving unit that receives the reflected light. The same can be said regarding the polarization property. As described above, although the diffuse reflection component and the internal scatter component are measured irrespective of the direction in which the light source that emits light to the object is present, the polarization properties thereof are different from each other. More particularly, it can be assumed that the diffuse reflection component divides the object surface into minute areas and satisfies the Fresnel reflection property in each area. Hence, the polarization property of the diffuse reflection component is such that, when the incident light is of the non-polarized type, the horizontal polarization component S is greater as compared to the vertical polarization component P. In contrast, the internal scatter component scatters inside the object before coming out. Hence, the polarization property of the internal scatter component is such that, when the incident light is of the non-polarized type, the internal scatter component is not easily affected by the polarization component of the incident light on the object, and the vertical polarization component P becomes stronger when the internal scatter component comes out of the object.

Regarding the case explained in the present embodiment, while capturing images of the front view from the own motor vehicle, most of the objects (such as the asphalt or the manhole covers) that can possibly be present in the imaging area have more than a little uneven surface. Therefore, it can be considered that the specular reflection component is small. Consequently, in the present embodiment, it can be considered that the reflected light from the objects present in the imaging area of the imaging device 200 predominately contain the diffuse reflection component and the internal scatter component. As a result, a comparison of intensities between the horizontal polarization component S and the vertical polarization component P included in the reflected light makes it possible to understand that a stronger horizontal polarization component S indicates a greater amount of the diffuse reflection component included in the reflected light and a stronger vertical polarization component P indicates a greater amount of the internal scatter component included in the reflected light.

Figure 38:
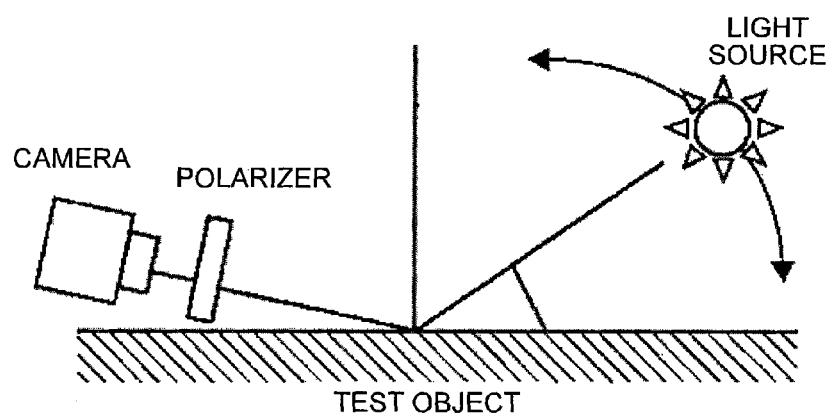
FIG. 38 is an explanatory diagram for explaining the overview of an experiment performed in a laboratory to capture images of a horizontal polarization component S and images of a vertical polarization component P with a fixed camera while varying the position of a light source with respect to test objects.

FIG. 38 is an explanatory diagram for explaining the overview of an experiment performed in a laboratory to capture images of the horizontal polarization component S and images of the vertical polarization component P with a fixed camera while varying the position of a light source with respect to test objects.

During this experiment, in a laboratory, images of the horizontal polarization component S and images of the vertical polarization component P are captured with a fixed camera while varying the position of a light source with respect to an asphalt surface and a surface of steel coated with paint; and the changes in the difference polarization degrees are measured. FIG. 38 is an explanatory diagram of an optical system that was subjected to evaluative analysis. Herein, a halogen lamp is used as the light source, a vision camera is used as the camera, and a polarizer is installed in front of the camera to enable rotational-selection of the polarization direction.

Figure 39:
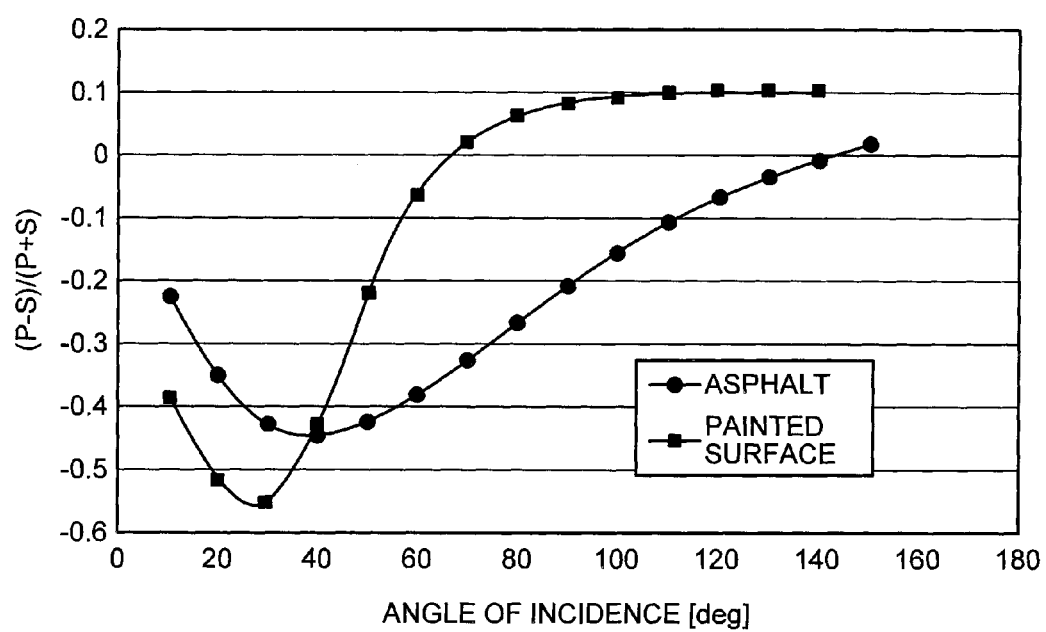
FIG. 39 is a graph illustrating the result of an experiment performed in a laboratory to capture images of the horizontal polarization component S and images of the vertical polarization component P with a fixed camera while varying the position of a light source with respect to an asphalt surface and a painted surface as test objects.

FIG. 39 is a graph illustrating the result of the experiment.

In this graph, the horizontal axis represents the angle of incidence (the light source position) and the vertical axis represents the difference polarization degree. With respect to the horizontal direction, the elevation angle of the camera is 10°. The difference polarization degree is calculated from luminance information of the substantially central part of the image captured at each angle of incidence. However, the difference polarization degrees used in the experiment are the ratios of the values obtained by subtracting the horizontal polarization component S from the vertical polarization component P to the total of the horizontal polarization component S and the vertical polarization component P. Therefore, the positivity and the negativity are opposite to the difference polarization degrees according to the present embodiment. Thus, regarding the difference polarization degrees used in the experiment, positive values are taken when the vertical polarization component P is greater than the horizontal polarization component S and negative values are taken when the horizontal polarization component S is greater than the vertical polarization component P.

As is clear from the graph illustrated in FIG. 39, regarding the asphalt surface, the difference polarization degrees are negative values across almost the entire range of angles of incidence, which indicates that the horizontal polarization component S is stronger than the vertical polarization component P. That is because of the fact that the reflected light from the asphalt surface predominately contains the diffuse reflection component. In contrast, regarding the painted surface, when the angle of incidence exceeds 60°, the difference polarization degrees take positive values. That is because of the fact that the reflected light from the painted surface contains the internal scatter component and the diffuse reflection component. Thus, by referring to the differences in the difference polarization degrees (differences in the polarization property); it becomes possible to recognize the asphalt surface and the painted surface in a distinct manner.

In the present embodiment, the result of the detection operation for detecting three-dimensional objects is used in performing driving support control such as issuing warnings to the driver of the own motor vehicle 100 or controlling the steering wheel or the brakes of the own motor vehicle 100. More particularly, when a three-dimensional object is determined to be present, the determination result is sent to the vehicle running control unit 108 and, for example, is used in controlling the automatic braking system of the own motor vehicle 100. Such measures are expected to be effective in reducing the number of traffic accidents. Moreover, for example, lane departure information can be displayed on a CRT screen of the vehicle navigation system in the own motor vehicle so as to draw the driver's attention to the situation.

Detection Operation for Detecting Roadsides

Explained below is a detection operation according to the present embodiment for detecting roadsides.

In the present embodiment, with the aim of preventing the own motor vehicle from departing from the roadable area, a detection operation is performed to detect the roadsides as target objects for detection. Herein, the roadsides point to the unevenness present between the motorway and pedestrian corridors, street gutters, roadside planting, guardrails, and concrete sidewalls.

During the detection operation according to the present embodiment for detecting the roadsides; of the information that can be obtained from the imaging unit 101, polarization information is used that is obtained by comparing the horizontal polarization component S and the vertical polarization component P of the white color component (non-dispersive light). Meanwhile, the vertical polarization component of the white color component can also contain the vertical polarization component of red light. In the present embodiment, the difference polarization degrees ((S−P)/(S+P)) of the horizontal polarization component S and the vertical polarization component P of the white color component (non-dispersive light) are used as this polarization information.

Firstly, from the image data of the horizontal polarization component S of the white color component (non-dispersive light) and from the image data of the vertical polarization component P of the white color component (non-dispersive light) of images captured by the imaging unit 101, a difference polarization degree image is generated in which pixel values point to difference polarization degrees ((S−P)/(S+P)). Then, in an identical manner to the detection operation for detecting three-dimensional objects, a plurality of processing lines is set. Herein, the method of setting the processing lines (or processing lines) is identical to that explained in the detection operation for detecting three-dimensional objects.

Once the processing lines are set in the abovementioned manner, difference values between pairs of adjacent pixel values (difference polarization degrees) are calculated along the processing lines. If a difference value is equal to greater than a roadside edge threshold value, then that area between the corresponding two adjacent pixels is identified as an edge. Subsequently, the pixel values (difference polarization degrees) of the pixels related to the identified edge are compared with a threshold value for roadside identification. If the pixel values are equal to or greater than the threshold value for roadside identification, the corresponding edge is extracted as an edge of a roadside.

By performing such edge extracting operation for all processing lines, it becomes possible to extract image areas enclosed by the edges of roadsides as roadside image area candidates. Then, the roadside image area candidates that are extracted are subjected to the shape approximation recognition operation. More particularly, the shape of a roadside image area candidate is compared with roadside shape templates that are stored in advance. If the shape of a roadside image area candidate matches with a roadside shape template, then that roadside image area candidate is identified to be a roadside image area. Herein, the shape approximation recognition operation is identical to the shape approximation recognition operation performed during the detection operation for detecting three-dimensional objects.

Meanwhile, the threshold values that are used at the time of detecting roadsides can be changed according to the changes in the environment. For example, the threshold values can be changed depending on the time period such as daytime or nighttime or depending on the weather such as rainy weather or fair weather. To perform such changes, it is possible to make use of time information or information of a rain sensor or a sunshine sensor.

The reason for being able to recognize roadsides with the use of difference polarization degrees is identical to the reason for being able to recognize three-dimensional objects. That is, since the difference polarization degrees vary depending on the materials or the angles of incidence, it becomes possible to extract borders (edges) between the road surface and the roadsides based on the difference polarization degrees. Moreover, by performing the shape approximation recognition operation, the types of the roadsides can also be identified using shape templates.

Figure 40A:
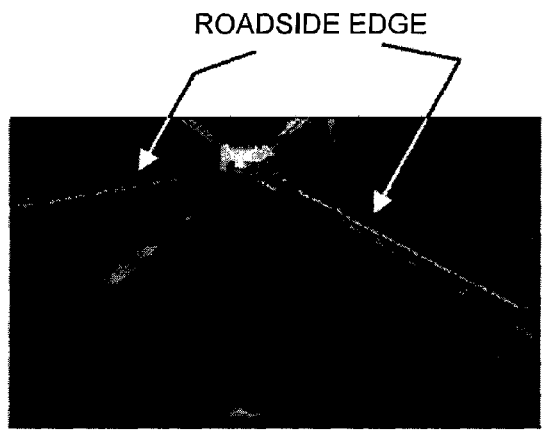
FIG. 40A is an exemplary image illustrating a monochrome luminance image (non-dispersive type/non-polarized type) in which an imaging area containing roadsides is captured.
Figure 40B:
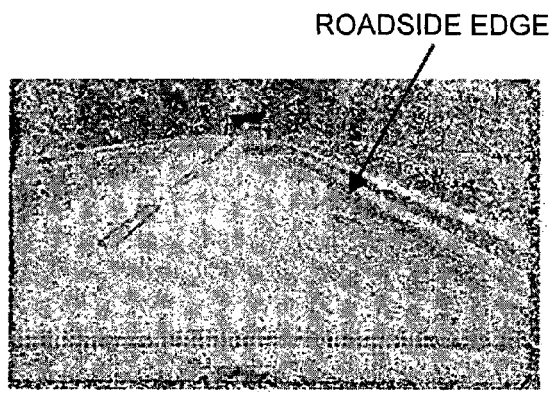
FIG. 40B is an exemplary image illustrating a difference polarization degree image of non-dispersive type in which the same imaging area is captured.

FIGS. 40A and 40B are exemplary images respectively illustrating a monochrome luminance image (non-dispersive type/non-polarized type) and a difference polarization degree image of non-dispersive type captured within the same imaging area.

These exemplary images are captured when the own motor vehicle is running inside a tunnel. Therefore, the imaging area is dark. For that reason, in the monochrome luminance image illustrated in FIG. 40A, it can be seen that there is not much contrast between the road surface and the tunnel sidewalls (roadsides). In contrast, in the difference polarization degree image illustrated in FIG. 40B, there is a sharp contrast between the road surface and the tunnel sidewalls (roadsides). Therefore, even though it is difficult to identify the tunnel sidewalls in the monochrome luminance image, a highly accurate identification of the tunnel sidewalls becomes possible when the difference polarization degree image is used.

Herein, regarding the difference polarization degrees accompanying the differences in materials, the difference between the polarization reflectance property of the asphalt (road surface) that is the material used in making the road surface and the polarization reflectance property of the concrete sidewalls (roadsides) is subjected to evaluative analysis and it is confirmed that the respective polarization reflectance models are different and it is confirmed that consequently it is possible to distinguish between the asphalt road surface and the concrete sidewalls. The concrete explanation is given below.

Figure 41:
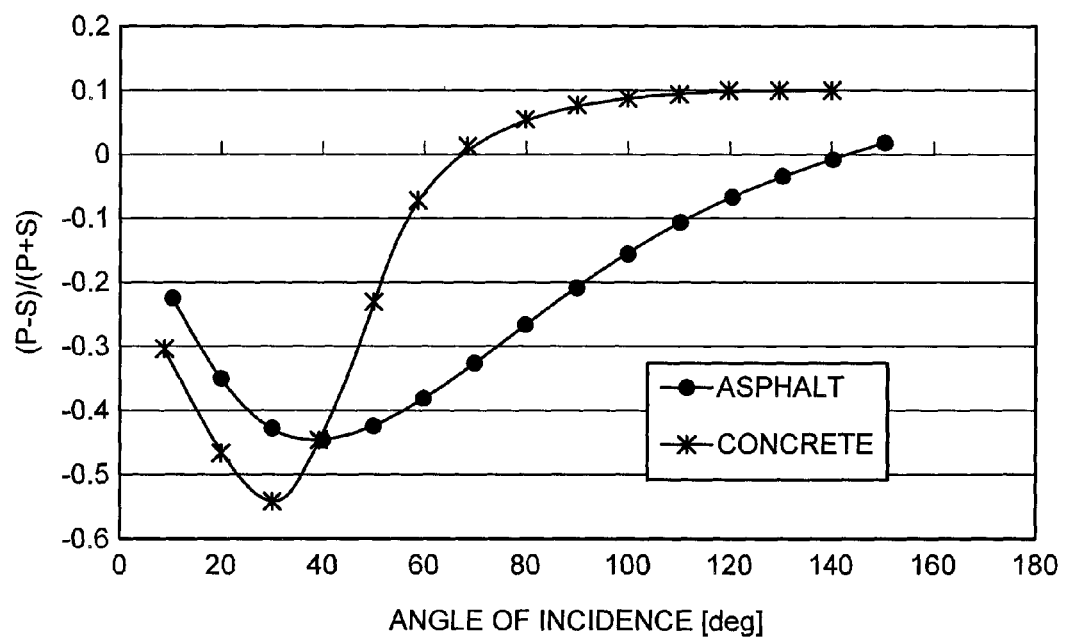
FIG. 41 is a graph illustrating the result of an experiment performed in a laboratory to capture images of the horizontal polarization component S and images of the vertical polarization component P with a fixed camera while varying the position of a light source with respect to an asphalt surface and a concrete surface as test objects.

FIG. 41 is a graph illustrating the result of an experiment performed in a laboratory to capture images of the horizontal polarization component S and images of the vertical polarization component P with a fixed camera while varying the position of a light source with respect to an asphalt surface and a concrete surface as test objects.

Meanwhile, in this experiment, the laboratory equipment is identical to that illustrated in FIG. 38. Moreover, the experimental conditions are identical to the case of performing an experiment on the asphalt surface and a painted surface.

As is clear from the graph illustrated in FIG. 41, as described already regarding the asphalt surface, the difference polarization degrees are negative values across almost the entire range of angles of incidence, which indicates that the horizontal polarization component S is stronger than the vertical polarization component P. In contrast, regarding the concrete surface, changes close to the abovementioned painted surface are seen, and it is clear that the reflected light from the concrete surface contains the internal scatter component and the diffuse reflection component. Thus, by referring to the differences in the difference polarization degrees (differences in the polarization property); it becomes possible to recognize the asphalt surface and the concrete surface in a distinct manner.

In the present embodiment, the result of the detection operation for detecting roadsides is used in performing driving support control such as issuing warnings to the driver of the own motor vehicle 100 or controlling the steering wheel or the brakes of the own motor vehicle 100. More particularly, roadside determination result is sent to the vehicle running control unit 108 and, for example, is used in controlling the automatic braking system of the own motor vehicle 100. Such measures are expected to be effective in reducing the number of traffic accidents. Moreover, for example, lane departure information can be displayed on a CRT screen of the vehicle navigation system in the own motor vehicle so as to draw the driver's attention to the situation.

Detection Operation for Detecting White Lines

Explained below is a detection operation according to the present embodiment for detecting white lines.

In the present embodiment, with the aim of avoiding departure of the own motor vehicle from the roadable area, a detection operation is performed to detect white lines (demarcation lines) as target objects for detection. Herein, the white lines include all types of lines such as solid lines, dashed lines, dotted lines, and double lines that are drawn to demarcate the roads. Moreover, apart from the white lines, other demarcation lines such as yellow lines can also be detected in the same manner.

During the detection operation according to the present embodiment for detecting white lines; of the information that can be obtained from the imaging unit 101, polarization information of the vertical polarization component P of the white color component (non-dispersive light) is used. Meanwhile, the vertical polarization component of the white color component can also contain the vertical polarization component of cyan light. Generally, it is known that the white lines and the asphalt surface have a flat spectral luminance characteristic in the visible light area. In contrast, since the cyan light contains a broad spectrum within the visible light area, it is suitable to capture images of the asphalt or the white lines. Thus, if the optical filter 205 according to the second configuration example described above is used and if the vertical polarization component of cyan light is included in the vertical polarization component of the white color component, the imaging pixels that are used increase in number. As a result, the resolution improves and the white lines at far distance can also be detected.

On many roads, white lines are drawn on the road surface that is close to black in color. Thus, in images of the vertical polarization component P of the white color component (non-dispersive light), the luminance of the portions of white lines is sufficiently large as compared to the luminance of other portions on the road surface. For that reason, during the detection operation according to the present embodiment for detecting white lines; of the portions of the road surface, the portions having the luminance equal to or greater than a predetermined threshold value are determined to white lines. Particularly, in the present embodiment, in images of the vertical polarization component P of the white color component (non-dispersive light), the horizontal polarization component S is removed. Therefore, it becomes possible to obtain images that are free of the glare from wet roads in the rainy season. As a result, white line detection can be performed without falsely recognizing the ambient light, such as the glare of headlamps that is reflected from the wet road during nighttime, as the white lines.

During the detection operation according to the present embodiment for detecting white lines; of the information that can be obtained from the imaging unit 101, polarization information can be used that contains the comparison of the horizontal polarization component S and the vertical polarization component P of the white color component (non-dispersive light). For example, the difference polarization degrees ((S−P)/(S+P)) of the horizontal polarization component S and the vertical polarization component P can be used as this polarization information. Usually, the reflected light from a white line predominately contains the diffuse reflection component. Hence, in that reflected light, the vertical polarization component P and the horizontal polarization component S are almost equal, and the difference polarization degrees decrease close to zero. In contrast, in dry conditions, the asphalt portion not having white lines drawn thereon exhibits a characteristic of predominately containing the scatter reflection component as illustrated in FIG. 39 or in FIG. 41, and the difference polarization degrees thereof are positive values (opposite to the positivity and the negativity of the experiment result illustrated in FIG. 39 or in FIG. 41). Moreover, in wet conditions, the asphalt portion not having white lines drawn thereon exhibits a characteristic of predominately containing the specular reflection component, and the difference polarization degrees thereof are greater values. Thus, of the road portions, the portions having the polarization difference values smaller than a predetermined threshold value can be determined to be white lines.

Figure 42A:
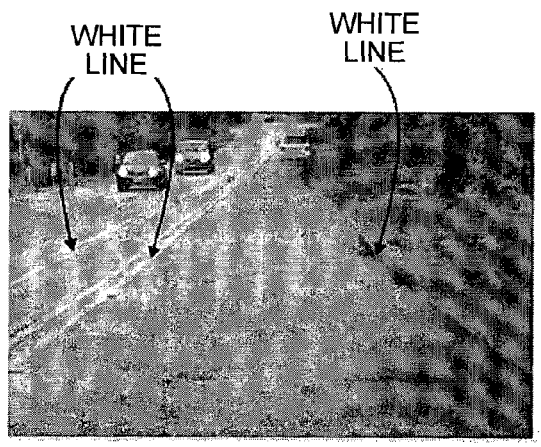
FIG. 42A is an exemplary image illustrating a monochrome luminance image (non-dispersive type/non-polarized type) in which an imaging area containing white lines in rainy weather is captured.
Figure 42B:
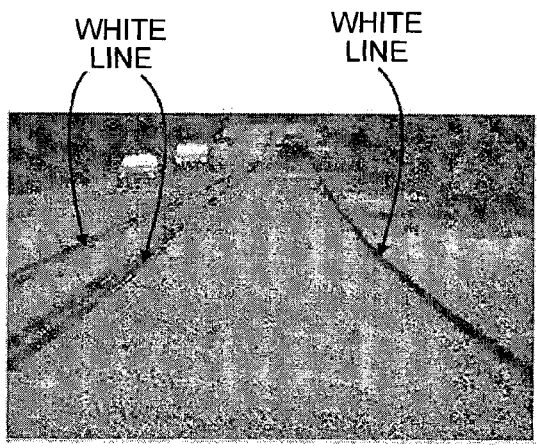
FIG. 42B is an exemplary image illustrating a difference polarization degree image of non-dispersive type in which the same imaging area is captured.

FIGS. 42A and 42B are exemplary images respectively illustrating a monochrome luminance image (non-dispersive type/non-polarized type) and a difference polarization degree image of non-dispersive type captured within the same imaging area in rainy weather.

Since these images are captured in rainy weather, the imaging area is comparatively dark, and the road surface is wet. Therefore, in the monochrome luminance image illustrated in FIG. 42A, there is not much contrast between white lines and the road surface. In contrast, in the difference polarization degree image illustrated in FIG. 42B, there is a sufficiently sharp contrast between the white lines and the road surface. Therefore, even though it is difficult to identify the white lines in the monochrome luminance image, a highly accurate identification of the white lines becomes possible when the difference polarization degree image is used.

Meanwhile, the white line in the right side of the images overlaps with the shadow. Thus, in the monochrome luminance image illustrated in FIG. 42A, there is particularly less contrast between the white line on the right side and the road surface. In contrast, in the difference polarization degree image illustrated in FIG. 42B, there is a sufficiently sharp contrast between the white line on the right side and the road surface. Therefore, regarding the white lines that are difficult to identify in the monochrome luminance image, a highly accurate identification becomes possible when the difference polarization degree image is used.

Detection Operation for Detecting Raindrops on Windshield

Explained below is a detection operation according to the present embodiment for detecting raindrops on the windshield.

In the present embodiment, with the aim of performing drive control of the wiper 107 and performing discharge control of the washer fluid, a detection operation is performed to detect raindrops as target objects for detection. Herein, although the explanation is given for the example when the attached material on the windshield is raindrops, the same is the case regarding other types of attached material such as bird droppings or splashes of water from the road surface due to an adjacent motor vehicle.

During the detection operation according to the present embodiment for detecting raindrops; of the information that can be obtained from the imaging unit 101, polarization information is used that is obtained by comparing the horizontal polarization component S and the vertical polarization component P of the raindrop detection image area 214 that receives the light which has passed through the infrared light transmission filter area 212 of the pre-filter 210. In the present embodiment, the difference polarization degrees ((S−P)/(S+P)) of the horizontal polarization component S and the vertical polarization component P of the white color component (non-dispersive light) are used as this polarization information.

As described above, the imaging unit 101 according to the present embodiment includes the light source 202. When the raindrops 203 are not attached to the outer wall surface of the windshield 105, the light emitted by the light source 202 reflects at the interface between the outer wall surface of the windshield 105 and the outside air, and the reflected light falls on the imaging device 200. On the other hand, when the raindrops 203 are attached to the outer wall surface of the windshield 105, the refractive index difference between the outer wall surface of the windshield 105 and the raindrops 203 becomes smaller than the refractive index difference between the outer wall surface of the windshield 105 and the outside air. As a result, the light emitted by the light source 202 passes through the interface and does not fall on the imaging device 200.

Figure 43:
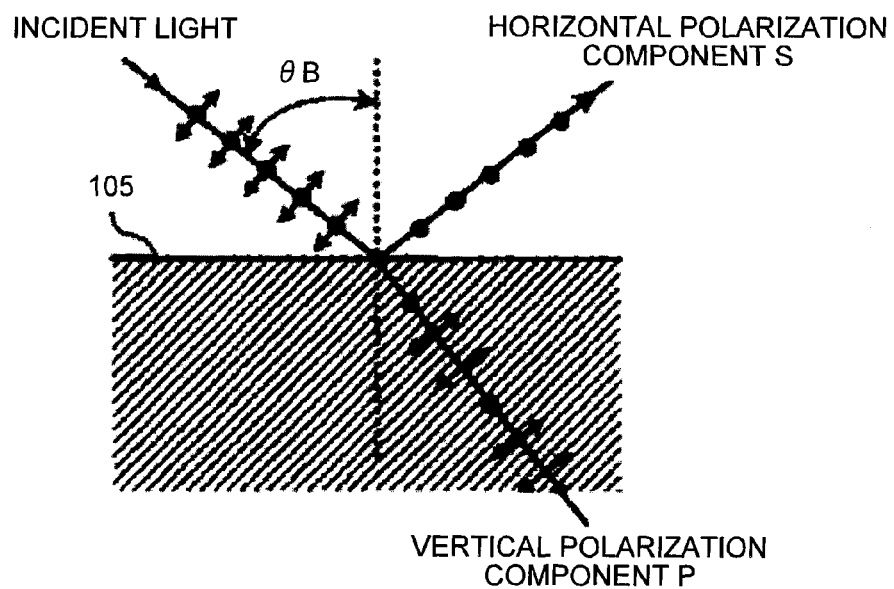
FIG. 43 is an explanatory diagram for explaining the polarization state of the reflected light at the Brewster's angle.

FIG. 43 is an explanatory diagram for explaining the polarization state of the reflected light at the Brewster's angle.

Generally, when light falls on a flat surface such as glass; the reflectance of the horizontal polarization component S monotonically increases accompanying the increase in the angle of incidence. In contrast, the reflectance of the vertical polarization component P becomes zero at a certain angle (at Brewster's angle θB). Thus, as illustrated in FIG. 43, the vertical polarization component P becomes does not get reflected and only serves as the transmitted light. Therefore, if the light source 202 is configured to emit only the light of the vertical polarization component P at the angle of incidence equal to the Brewster's angle θB from the inside of a motor vehicle toward the windshield 105; then there is no reflected light at the inner wall surface of the windshield 105 (i.e., the surface on the inside of the motor vehicle), and the outer wall surface of the windshield 105 gets exposed to the light of the vertical polarization component P. In case there is reflected light from the inner wall surface of the windshield 105, that reflected light becomes the ambient light falling on the imaging device 200 thereby leading to a decline in the raindrop detection rate.

In order to ensure that the light that is emitted by the light source 202 and that falls on the windshield 105 has only the vertical polarization component P; if the light source 202 is made of, for example, a light emitting diode (LED), then it is preferable to dispose a polarizer between the light source 202 and the windshield 105 with the aim of transmitting only the vertical polarization component P. Alternatively, if the light source 202 is made of a laser diode (LD); then, by taking into account the property that the LD can emit light of only a particular polarization component, the axis of the LD can be adjusted in such a way that only the light of the vertical polarization component P falls on the windshield 105.

Figure 44A:
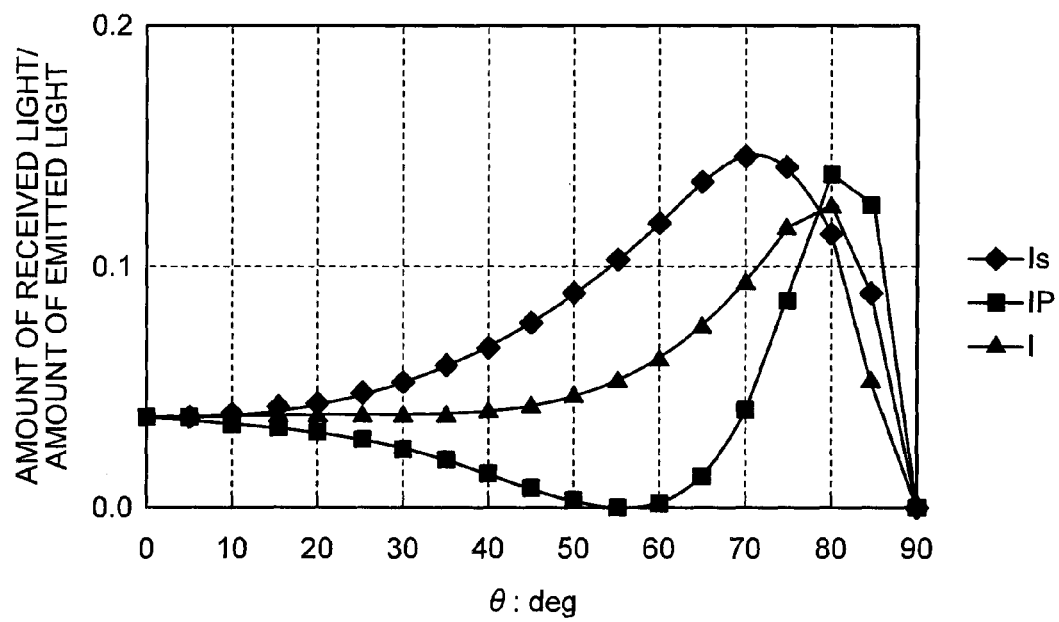
FIG. 44A is a graph illustrating, for each polarization component, the ratio of the amount of light received by the imaging device with respect to the amount of light emitted by the light source when the raindrops are not attached to the outer wall surface of the windshield.

FIG. 44A is a graph illustrating, for each polarization component, the ratio of the amount of light received by the imaging device 200 with respect to the amount of light emitted by the light source 202 when the raindrops are not attached to the outer wall surface of the windshield 105.

Figure 44B:
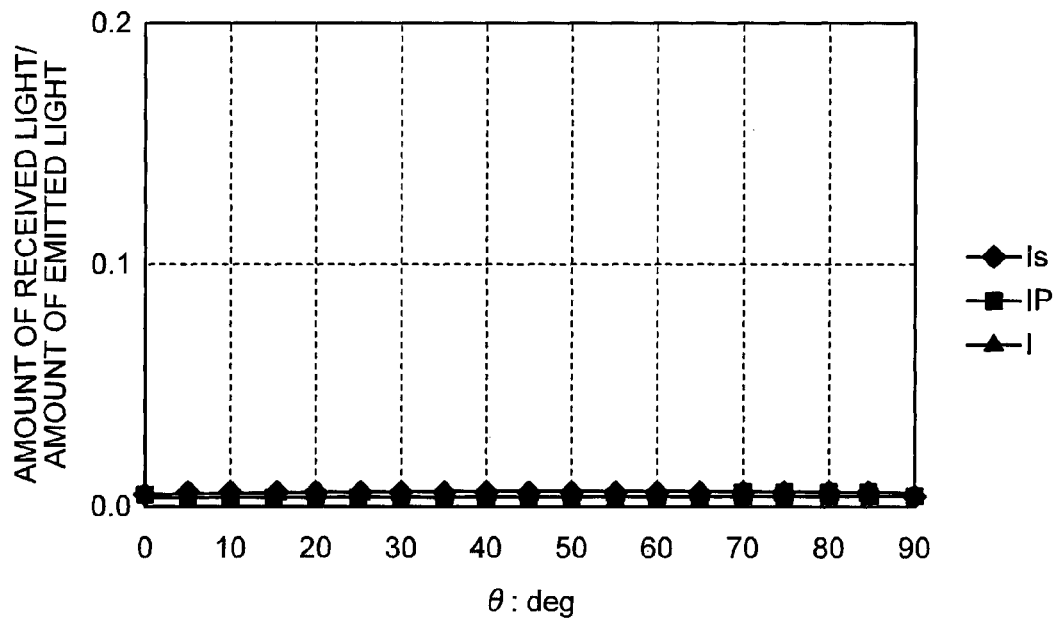
FIG. 44B is a graph illustrating, for each polarization component, the ratio of the amount of light received by the imaging device with respect to the amount of light emitted by the light source when the raindrops are attached to the outer wall surface of the windshield.

FIG. 44B is a graph illustrating, for each polarization component, the ratio of the amount of light received by the imaging device 200 with respect to the amount of light emitted by the light source 202 when the raindrops are attached to the outer wall surface of the windshield 105.

In these graphs, the horizontal axis represents the angle of incidence from the light source 202 to the windshield, and the vertical axis represents the ratio of the amount of light received by the imaging device 200 with respect to the amount of light emitted by the light source 202. The graphs referred to by "Is" are graphs regarding the horizontal polarization component S; the graphs referred to by "Ip" are graphs regarding the vertical polarization component P; and the graphs referred to by "I" are graphs regarding the average values of the horizontal polarization component S and the vertical polarization component P. All these graphs are calculated by assuming that the refractive index of the windshield 105 is 1.5 and the refractive index of the raindrops is 1.38.

In the present embodiment, as described above, the configuration is such that a polarizer is disposed between the light source 202 and the windshield 105 with the aim of transmitting only the vertical polarization component P to the windshield 105. However, in practice, it is difficult to adjust the polarization axis of the polarizer in such a way that only the light of the vertical polarization component P falls on the windshield 105. Thus, usually, the light of the horizontal polarization component S also falls on the windshield 105. For that reason, usually, the imaging device 200 receives the light of the horizontal polarization component S too.

Figure 45A:
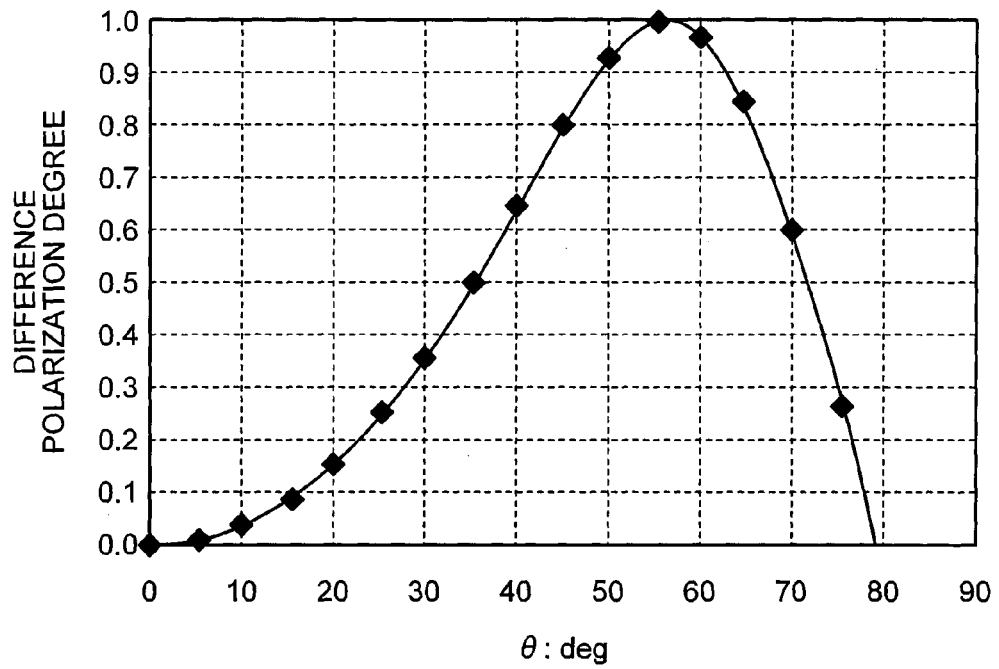
FIG. 45A is a graph illustrating the difference polarization degrees when the raindrops are not attached to the outer wall surface of the windshield.

FIG. 45A is a graph illustrating the difference polarization degrees when the raindrops are not attached to the outer wall surface of the windshield 105.

Figure 45B:
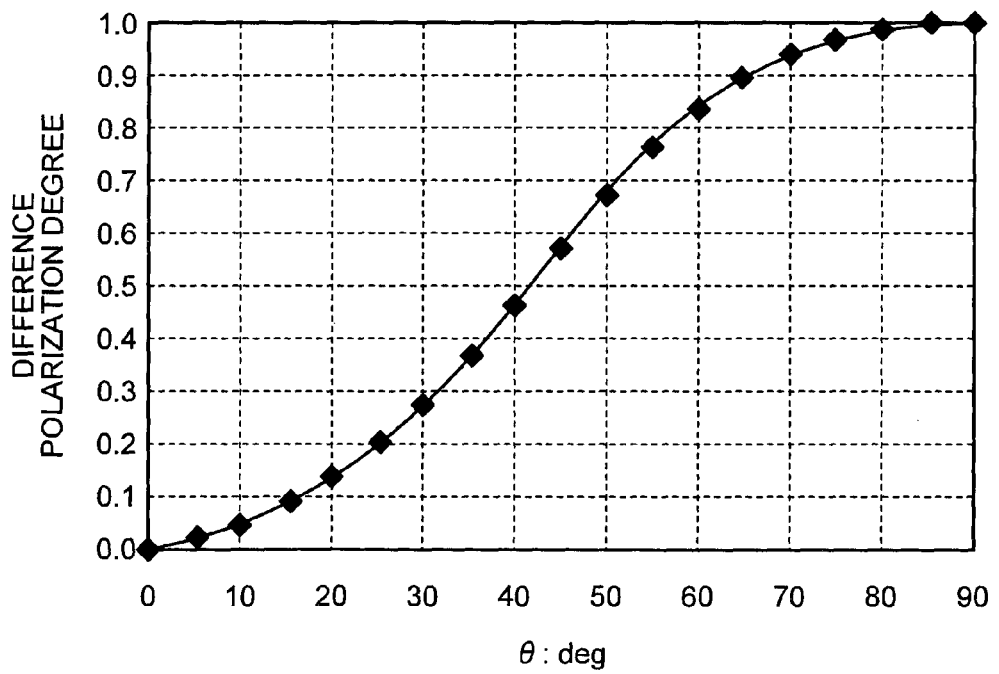
FIG. 45B is a graph illustrating the difference polarization degrees when the raindrops are attached to the outer wall surface of the windshield.

FIG. 45B is a graph illustrating the difference polarization degrees when the raindrops are attached to the outer wall surface of the windshield 105.

These graphs are also calculated by assuming that the refractive index of the windshield 105 is 1.5 and the refractive index of the raindrops is 1.38.

By comparing the graphs illustrated in FIG. 45A and FIG. 45B, it is clear that the incidence angle characteristics of the difference polarization degrees are different depending on whether or not the raindrops are attached. Moreover, among the graphs illustrated in FIG. 45A and FIG. 45B, the maximum difference in the difference polarization degrees occurs at around 50°, which is close to the Brewster's angle. Thus, by installing the light source 202 to have the angle of incidence at around 50°, it becomes possible to enhance the raindrop detection accuracy on the basis of the difference polarization degree images.

Figure 46:
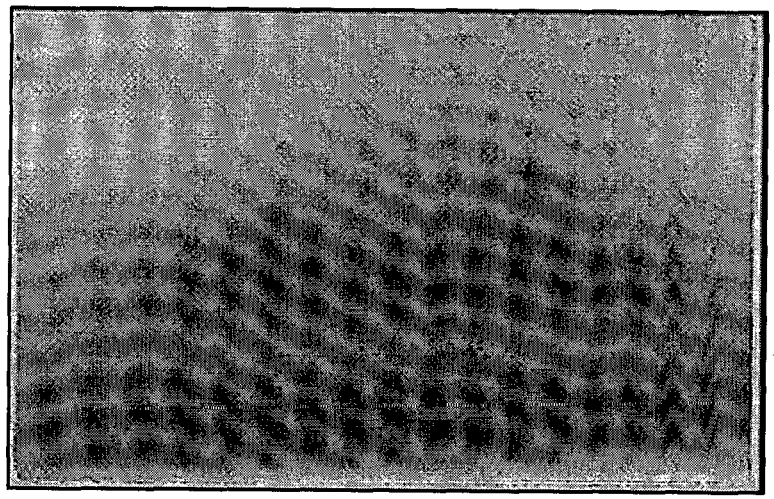
FIG. 46 illustrates an example of a difference polarization degree image of the windshield having raindrops attached thereto, when the installation is done to ensure that the angle of incidence is at around 50°.

FIG. 46 illustrates an example of a difference polarization degree image when the installation is done to ensure that the angle of incidence is at around 50°.

The exemplary image illustrated in FIG. 46 is a difference polarization degree image captured when the light source 202 emits light from the inside of the motor vehicle toward the windshield 105 in the dark. In the difference polarization degree image, it can be seen that there is a sufficiently sharp contrast between the image area in which raindrops are attached to the windshield and the image area in which raindrops are not attached to the windshield. Hence, by making use of the difference polarization degree image, the raindrops attached to the windshield 105 can be detected with a high degree of accuracy.

During the detection operation according to the present embodiment for detecting raindrops, firstly, the light source 202 is switched ON and a difference polarization degree image is generated in which pixel values point to the difference polarization degrees ((S−P)/(S+P)) based on the horizontal polarization component S and the vertical polarization component P of the raindrop detection image area 214 that receives the light which has passed through the infrared light transmission filter area 212. Then, with respect to that difference polarization degree image, an edge detection operation is performed using the known Laplacian filter. By performing the edge detecting operation, it becomes possible to generate an image in which a highlighted border separates a raindrop image area candidate and a no-raindrop image area candidate. Subsequently, a round shape detection operation is performed, and image areas detected to be round in shape are identified to be raindrops. During the round shape detecting operation, the generalized Hough transform, which is a known technique, is performed.

Subsequently, in the present embodiment, the number of areas that are identified to be raindrop image areas is calculated, and that number is converted into the amount of rainfall with the aim of calculating the amount of rainfall. Then, based on the amount of rainfall that is calculated, the wiper control unit 106 performs drive control of the wiper 107 or performs discharge control of the washer fluid.

Meanwhile, the imaging device 200 according to the present embodiment has what is called a monocular camera configuration. However, according to a modification example, an imaging device can be a stereo camera having a compound-eye camera configuration. The stereo camera includes two camera units, each of which can have the same configuration as the configuration of the imaging device 200 according to the embodiment described above.

The explanation given above is only an example, and the present invention produces a peculiar effect for each of the following aspects.

Aspect A

In the imaging device 200 for capturing images within an imaging area by means of receiving the light, via the optical filter 205, from an object present in the imaging area using the image sensor 206 that is configured with a pixel array having a two-dimensional arrangement of the photodiodes (light receiving elements) 206A; the optical filter 205 has the configuration in which the polarization filter layer 222 and the spectral filter layer 223 are laminated in the light transmission direction. The polarization filter layer 222 has the first type area, which selectively transmits the polarization component in only a particular direction (i.e., the vertical polarization component P), and the second type area, which either transmits the light without selecting a polarization component or selectively transmits the polarization component in the direction orthogonal to the abovementioned particular direction (i.e., the horizontal polarization component S). The first and second type areas are segmented into areas each corresponding to a unit area formed with one of the photodiodes 206A of the image sensor 206 (i.e., segmented in the units of imaging pixels). The spectral filter layer 223 includes the third type area, which selectively transmits the light of only a specific wavelength band (i.e. the red wavelength band or the cyan wavelength band) included in the used wavelength bands that can pass through the polarization filter layer 222, and the fourth type area, which either transmits the light without selecting a wavelength or transmits the light of a wavelength band that is different than the abovementioned specific wavelength band and that is included in the used wavelength bands. The third and fourth type areas are segmented into areas each corresponding to a unit area formed one or more photodiodes 206A of the image sensor 206. Of the polarization filter layer 222 and the spectral filter layer 223, the layer on the lower side in the lamination direction (i.e., the polarization filter layer 222) has an uneven top face in the lamination direction. Thus, the predetermined filling material 224 is filled on the top face in the lamination direction of the layer on the lower side in the lamination direction so that the top face of that layer is evened out. Subsequently, the other layer (i.e., the spectral filter layer 223) is formed on the layer that has been evened out. The optical filter 205 is configured in this manner.

With such a configuration, even if the other layer (i.e., the spectral filter layer 223) is formed on the layer having an uneven top face (i.e., the polarization filter layer 222), irregularity in the layer thickness of the other layer along the uneven face is prevented from occurring. That allows the other layer to fulfill its primary function. Moreover, as described in the present embodiment, by filling the filling material 224 in the depressed portions of the layer on the lower side in the lamination direction (i.e., the polarization filter layer 222), it becomes possible to prevent foreign substances from entering the depressed portions. As a result, it becomes possible to avoid a situation in which the entry of a foreign substance prevents the layer on the lower side in the lamination direction from fulfilling its primary function. Furthermore, as described in the present embodiment, since the layer on the lower side in the lamination direction (i.e., the polarization filter layer 222) is covered by the filling material 224, damage to that layer is prevented from occurring.

Besides, according to the present embodiment, it is possible to capture, at once, two-dimensional images in which three components, namely, the amount of transmitted light, the transmitted polarization components, and the transmitted wavelength bands are arbitrarily adjusted in the units of miniscule areas such as in the units of imaging pixels. Moreover, since the optical filter 205 according to the present embodiment has a static configuration without using any active devices such as liquid crystals; it becomes possible to achieve an affordable and simple optical system.

Aspect B

In the aspect A, the polarization filter layer 222 serves as the layer on the lower side in the lamination direction.

As compared to the spectral filter layer 223, the polarization filter layer 222 can be formed to have a smaller thickness. Thus, as compared to the spectral filter layer 223, the polarization filter layer 222 has poor mechanical strength, thereby making it vulnerable to damage. If the polarization filter layer 222 serves as the layer on the lower side in the lamination direction, then the filling material 224 covering the polarization filter layer 222 can also be filled thinly. That not only makes it easier to achieve smoothness of the top face of the filling material 224; but also makes it possible to protect the polarization filter layer 222, which is vulnerable to damage, using the filling material 224.

Aspect C

In the aspect A or the aspect B, the polarization filter layer 222 has a wire grid structure.

As described above, the wire grid structure can be manufactured using the semiconductor process, and the polarization axis can be adjusted by changing the groove orientation of the subwavelength structure. With that, it becomes possible to form polarizer patterns (polarization filter areas) having different polarization axes in the units of imaging pixels (in the size of few microns). Moreover, since the wire grid structure is made of fine metal wires, the optical filter 205 becomes highly reliable in terms of heat resistance/light resistance. Herein, light resistance points to the resistance against the degradation in the optical property due to ultraviolet light or the like. With such high heat resistance and high light resistance, the optical filter 205 can be suitably used in an in-vehicle imaging device.

Aspect D

In any one of the aspects A to C, the fourth type area of the spectral filter layer 223 transmits the light without selecting a wavelength; and the spectral filter layer 223 is formed by first uniformly forming a filter film serving as the third type area and then removing the filter film from the location corresponding to the fourth type area.

With such a configuration, the spectral filter layer 223 that is segmented into miniscule areas equivalent to a single pixel or a few pixels of the photodiodes 206A can be formed with relative ease.

Aspect E

In any one of the aspects A to D, the filling material is an inorganic material.

Such a filling material has high heat resistance/light resistance. As a result, the optical filter 205 becomes highly reliable in terms of heat resistance/light resistance.

Aspect F

In any one of the aspects A to E, the unit areas corresponding to the third type area and the fourth type area in the spectral filter layer 223 are identical to the unit areas corresponding to the first type area and the second type area in the polarization filter layer 222. In the spectral filter layer 223, the third type area and the fourth type area are arranged in an alternate manner. In the polarization filter layer 222 too, the first type area and the second type area of the same type are arranged in an alternate manner.

With such a configuration, it becomes possible to capture, at once, maximum four types of captured images in each of which a 2×2 matrix of imaging pixels constitutes a single image pixel. The maximum four types of captured images are: an image of the light that has passed through the first type area of the polarization filter layer 222 and through the third type area of the spectral filter layer 223; an image of the light that has passed through the first type area of the polarization filter layer 222 and through the fourth type area of the spectral filter layer 223; an image of the light that has passed through the second type area of the polarization filter layer 222 and through the third type area of the spectral filter layer 223; and an image of the light that has passed through the second type area of the polarization filter layer 222 and through the fourth type area of the spectral filter layer 223.

Aspect G

An object detecting apparatus includes: the imaging device 200 according to any one of the aspects A to F; and an object detection operation unit for detecting, based on captured images that are captured by the imaging unit, a detection target object present in the imaging area.

With such a configuration, a spectral image and a polarization image can be obtained by performing image capturing only for one time. Thus, as compared to a configuration in which those images are captured one after the other, it becomes possible to obtain spectral images and polarization images at a high frame rate and in a continuous manner. Therefore, even if a detection target object that is detectable from a spectral image and a polarization image performs high-speed movements within the imaging area, it is still possible to properly follow those movements.

Aspect H

In the aspect G, the imaging device 200 captures images of the vehicle-travelling direction front area of the own motor vehicle 100 as the imaging area. The detection target object includes an oncoming motor vehicle travelling in the opposite direction of the own motor vehicle 100 and a proceeding motor vehicle travelling in the same direction as the own motor vehicle 100. The specific wavelength band corresponding to the light transmitted by the third type area of the spectral filter layer 223 points to the wavelength band containing the wavelength of the color of tail lamps of motor vehicles (red color). The fourth type area of the spectral filter layer 223 transmits light without selecting a wavelength. The object detection operation unit detects a proceeding motor vehicle based on output signals of those light receiving elements (imaging pixels "a" and "f") of the image sensor 206 which received the transmitted light from the third type area of the spectral filter layer 223. Besides, the object detection operation unit detects an oncoming motor vehicle either based on output signals of the light receiving element (imaging pixel "b") of the image sensor 206 which received the transmitted light from the first type area of the polarization filter layer 222 and from the fourth type area of the spectral filter layer 223 or based on output signals of low signal level from among the output signals of the light receiving element (imaging pixel "e") of the image sensor 206 which received the transmitted light from the second type area of the polarization filter layer 222 and from the fourth type area of the spectral filter layer 223.

With such a configuration, as described above, tail lamps can be identified with a high degree of accuracy. Based on that identification result, it becomes possible to achieve a high degree of detection accuracy while detecting proceeding motor vehicles. Similarly, as described above, headlamps can be identified with a high degree of accuracy. Based on that identification result, it becomes possible to achieve a high degree of detection accuracy while detecting oncoming motor vehicles.

Aspect I

In the aspect G or the aspect H, the imaging device 200 captures images of the vehicle-travelling direction front area of the own motor vehicle 100 as the imaging area. The detection target object includes a demarcation line such as a white line drawn on the road surface. The object detection operation unit detects such a demarcation line based on index values such as difference polarization degrees that are calculated from output signals of the light receiving element (imaging pixel "b") of the image sensor 206 which received the transmitted light from the first type area of the polarization filter layer 222 and output signals of the light receiving element (imaging pixel "e") of the image sensor 206 which received the transmitted light from the second type area that is adjacent to the first type area of the polarization filter layer 222.

With such a configuration, as described above, even if it is difficult to identify the white lines in a monochrome luminance image, a highly accurate identification of the white lines becomes possible when a difference polarization degree image is used in which pixel values point to index values such as difference polarization degrees.

Aspect J

The optical filter 205 is disposed in an imaging device, which includes the image sensor 206 configured with a pixel array having a two-dimensional arrangement of light receiving elements, between the image sensor 206 and the imaging area. The optical filter has a configuration in which the polarization filter layer 222 and the spectral filter layer 223 are laminated in the light transmission direction. The polarization filter layer 222 includes the first type area, which selectively transmits the polarization component in only a particular direction, and the second type area, which either transmits the light without selecting a polarization component or selectively transmits the polarization component in a different direction than the abovementioned particular direction. The first and second type areas are segmented into areas each corresponding to a unit area formed with one or more light receiving elements of the image sensor 206. The spectral filter layer 223 includes the third type area, which selectively transmits the light of only a specific wavelength band included in the used wavelength bands that can pass through the polarization filter layer 222, and the fourth type area, which either transmits the light without selecting a wavelength or transmits the light of a wavelength band that is different than the abovementioned specific wavelength band and that is included in the used wavelength bands. The third and fourth type areas are segmented into areas each corresponding to a unit area formed with one or more light receiving elements of the image sensor 206. Of the polarization filter layer 222 and the spectral filter layer 223, the layer on the lower side in the lamination direction has an uneven top face in the lamination direction. The optical filter is formed by filling the uneven top face with a predetermined filling material so as to even out the top face and then forming the other layer.

With such a configuration, even if the other layer (i.e., the spectral filter layer 223) is formed on the layer having an uneven top face (i.e., the polarization filter layer 222), irregularity in the layer thickness of the other layer along the uneven face is prevented from occurring. That allows the other layer to fulfill its primary function. Moreover, as described in the present embodiment, by filling the depressed portions of the layer on the lower side in the lamination direction (i.e., the polarization filter layer 222) with the filling material 224, it becomes possible to prevent foreign substances from entering the depressed portions. As a result, it becomes possible to avoid a situation in which the entry of a foreign substance prevents the layer on the lower side in the lamination direction from fulfilling its primary function. Furthermore, as described in the present embodiment, since the layer on the lower side in the lamination direction (i.e., the polarization filter layer 222) is covered by the filling material 224, damage to that layer is prevented from occurring. Moreover, since the optical filter 205 according to the present embodiment has a static configuration without using any active devices such as liquid crystals; it becomes possible to achieve an affordable and simple optical system.

Aspect K

In the manufacturing method of the optical filter 205 that is disposed in an imaging device, which includes the image sensor 206 configured with a pixel array having a two-dimensional arrangement of light receiving elements, between the image sensor 206 and the imaging area; one of the polarization filter layer 222, in which the first type area selectively transmits the polarization component in only a particular direction and the second type area either transmits the light without selecting a polarization component or selectively transmits the polarization component in a different direction than the abovementioned particular direction are segmented into areas each being a unit area formed with one light receiving element or with two or more light receiving elements of the image sensor 206, and the spectral filter layer 223, in which the first type area selectively transmits the light of only a specific wavelength band included in the used wavelength bands that can pass through the polarization filter layer 222 and the second type area either transmits the light without selecting a wavelength or transmits the light of a wavelength band that is different than the abovementioned specific wavelength band and that is included in the used wavelength bands, are segmented into areas each being a unit area formed with one light receiving element or with two or more light receiving elements of the image sensor 206, is formed to have an uneven top face in the lamination direction followed by filling a predetermined filling material on the top face in the lamination direction of that layer so that the top face of that layer is evened out, which is followed by forming the other layer.

With such a configuration, even if the other layer (i.e., the spectral filter layer 223) is formed on the layer having an uneven top face (i.e., the polarization filter layer 222), irregularity in the layer thickness of the other layer along the uneven face is prevented from occurring. That allows the other layer to fulfill its primary function. Moreover, as described in the present embodiment, by filling the filling material 224 in the depressed portions of the layer on the lower side in the lamination direction (i.e., the polarization filter layer 222), it becomes possible to prevent foreign substances from entering the depressed portions. As a result, it becomes possible to avoid a situation in which the entry of a foreign substance prevents the layer on the lower side in the lamination direction from fulfilling its primary function. Furthermore, as described in the present embodiment, since the layer on the lower side in the lamination direction (i.e., the polarization filter layer 222) is covered by the filling material 224, damage to that layer is prevented from occurring. Moreover, since the optical filter 205 according to the present embodiment has a static configuration without using any active devices such as liquid crystals; it becomes possible to achieve an affordable and simple optical system.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. An imaging device for capturing images within an imaging area comprising:
    an optical filter; and
    an image sensor that is configured with a pixel array having a two-dimensional arrangement of light receiving elements, wherein
    the optical filter has a configuration in which a polarization filter layer and a spectral filter layer are laminated in light transmission direction,
    the polarization filter layer includes a first type area, which selectively transmits a polarization component of light in only a particular direction, and a second type area, which either transmits light without selecting a polarization component or selectively transmits a polarization component of light in a different direction than the particular direction, the first and second type areas being segmented into areas each corresponding to a unit area formed with one or more light receiving elements of the image sensor,
    the spectral filter layer includes a third type area, which selectively transmits light of only a specific wavelength band included in used wavelength bands that can pass through the polarization filter layer, and a fourth type area, which either transmits light without selecting a wavelength or transmits light of a wavelength band that is different than the specific wavelength band and that is included in the used wavelength bands, the third and fourth type areas being segmented into areas each corresponding to a unit area formed with one or more light receiving elements of the image sensor,
    of the polarization filter layer and the spectral filter layer, the layer on the lower side in lamination direction has an uneven top face in the lamination direction,
    the optical filter is formed by filling the uneven top face with a predetermined filling material so as to even out the top face and then forming other layer,
    the fourth type area of the spectral filter layer transmits light without selecting a wavelength, and
    the spectral filter layer is formed by first uniformly forming a filter film serving as the third type area and then removing the filter film from the location corresponding to the fourth type area.

2. The imaging device according to claim 1, wherein the layer on the lower side in the lamination direction is the polarization filter layer.

3. The imaging device according to claim 1, wherein the polarization filter layer has a wire grid structure.

4. The imaging device according to claim 1, wherein the filling material is an inorganic material.

5. The imaging device according to claim 1, wherein
    the unit areas corresponding to the third type area and the fourth type area in the spectral filter layer are identical to the unit areas corresponding to the first type area and the second type area in the polarization filter layer, and
    the third type area and the fourth type area in the spectral filter layer are arranged in an alternate manner, and the first type area and the second type area in the polarization filter layer are also arranged in an alternate manner.

6. An object detecting apparatus comprising:
    the imaging device according to claim 1; and
    an object detection operation unit that, based on captured images that are captured by the imaging unit, detects a detection target object present in the imaging area.

7. The object detecting apparatus according to claim 6, wherein
    the imaging device captures images with a vehicle-travelling direction front area of own motor vehicle serving as the imaging area,
    the detection target object includes an oncoming motor vehicle travelling in the opposite direction to own motor vehicle and a proceeding vehicle travelling in the same direction as own motor vehicle,
    the specific wavelength band corresponding to light transmitted by the third type area of the spectral filter layer is a wavelength band containing the wavelength of the color of a tail lamp of a motor vehicle,
    the fourth type area of the spectral filter layer transmits light without selecting a wavelength, and
    the object detection operation unit detects a proceeding motor vehicle based on an output signal of a light receiving element of an image sensor which received the transmitted light from the third type area of the spectral filter layer, and detects an oncoming motor vehicle either based on an output signal of a light receiving element of the image sensor which received the transmitted light from the first type area of the polarization filter layer and from the fourth type area of the spectral filter layer or based on an output signal of low signal level from among output signals of a light receiving element of the image sensor which received the transmitted light from the second type area of the polarization filter layer and from the fourth type area of the spectral filter layer.

8. The object detecting apparatus according to claim 6, wherein
the imaging device captures images with a vehicle-travelling direction front area of own motor vehicle serving as an imaging area,
the detection target object includes a demarcation line drawn on a road surface, and
the object detection operation unit detects a demarcation line based on a predetermined index value that is calculated by referring to an output signal of a light receiving element of the image sensor which received the transmitted light from the first type area of the polarization filter layer and by referring to an output signal of a light receiving element of the image sensor which received the transmitted light from the second type area that is adjacent to the first type area of the polarization filter layer.

9. An optical filter disposed in an imaging device, which includes an image sensor configured with a pixel array having a two-dimensional arrangement of light receiving elements, between the image sensor and an imaging area, the optical filter comprising:
a polarization filter layer and a spectral filter layer laminated in light transmission direction, wherein
the polarization filter layer includes a first type area, which selectively transmits a polarization component in only a particular direction, and a second type area, which either transmits light without selecting a polarization component or selectively transmits a polarization component in a different direction than the particular direction, the first and second type areas being segmented into areas each corresponding to a unit area formed with one or more light receiving elements of the image sensor,
the spectral filter layer includes a third type area, which selectively transmits light of only a specific wavelength band included in used wavelength bands that can pass through the polarization filter layer, and a fourth type area, which either transmits light without selecting a wavelength or transmits light of a wavelength band that is different than the specific wavelength band and that is included in the used wavelength bands, the third and fourth type areas being segmented into areas each corresponding to a unit area formed with one or more light receiving elements of the image sensor,
of the spectral filter layer and the polarization filter layer, the layer on the lower side in lamination direction has an uneven top face in the lamination direction,
the optical filter is formed by filling the uneven top face with a predetermined filling material so as to even out the top face and then forming other layer,
the fourth type area of the spectral filter layer transmits light without selecting a wavelength, and
the spectral filter layer is formed by first uniformly forming a filter film serving as the third type area and then removing the filter film from the location corresponding to the fourth type area.

10. A manufacturing method for manufacturing an optical filter that is disposed in an imaging device, which includes an image sensor configured with a pixel array having a two-dimensional arrangement of light receiving elements, between the image sensor and an imaging area, the manufacturing method comprising:
forming one layer of a polarization filter layer and a spectral filter layer, which are to be laminated, so that the one layer has an uneven top face in lamination direction;
filling the uneven top face with a predetermined filling material so as to even out the top face; and
forming other layer, wherein
the polarization filter layer includes a first type area, which selectively transmits a polarization component in only a particular direction, and a second type area, which either transmits light without selecting a polarization component or selectively transmits a polarization component in a different direction than the particular direction, the first and second type areas being segmented into areas each corresponding to a unit area formed with one or more light receiving elements of the image sensor,
the spectral filter layer includes a third type area, which selectively transmits light of only a specific wavelength band included in used wavelength bands that can pass through the polarization filter layer, and a fourth type area, which either transmits light without selecting a wavelength or transmits light of a wavelength band that is different than the specific wavelength band and that is included in the used wavelength bands, the third and fourth type areas being segmented into areas each corresponding to a unit area formed with one or more light receiving elements of the image sensor,
the fourth type area of the spectral filter layer transmits light without selecting a wavelength, and
the spectral filter layer is formed by first uniformly forming a filter film serving as the third type area and then removing the filter film from the location corresponding to the fourth type area.

* * * * *